United States Patent
Nishimiya et al.

(10) Patent No.: US 11,845,786 B2
(45) Date of Patent: Dec. 19, 2023

(54) PEPTIDES INHIBITING KLK1, KLK4, OR KLK4 AND KLK8

(71) Applicant: Daiichi Sankyo Company, Limited, Tokyo (JP)

(72) Inventors: Daisuke Nishimiya, Sumida-ku (JP); Masakazu Tamura, Yokohama (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 12 days.

(21) Appl. No.: 17/533,038

(22) Filed: Nov. 22, 2021

(65) Prior Publication Data

US 2022/0106384 A1  Apr. 7, 2022

Related U.S. Application Data

(63) Continuation of application No. 16/642,885, filed as application No. PCT/JP2018/033037 on Sep. 6, 2018, now Pat. No. 11,208,467.

(30) Foreign Application Priority Data

Sep. 7, 2017 (JP) ................................ 2017-171776

(51) Int. Cl.
*C07K 14/81* (2006.01)
*A61K 47/62* (2017.01)
*A61K 47/68* (2017.01)
*A61K 38/00* (2006.01)
*C07K 14/00* (2006.01)

(52) U.S. Cl.
CPC .............. *C07K 14/81* (2013.01); *A61K 47/62* (2017.08); *A61K 47/68* (2017.08); *C07K 14/001* (2013.01); *A61K 38/00* (2013.01)

(58) Field of Classification Search
CPC .. C07K 14/81; C07K 14/001; C07K 14/8135; A61K 47/62; A61K 47/68; A61K 38/00
See application file for complete search history.

(56) References Cited

U.S. PATENT DOCUMENTS

| 10,550,154 | B2 | 2/2020 | Nishimiya et al. |
| 2015/0197546 | A1 | 7/2015 | Nishimaya et al. |
| 2020/0207837 | A1 | 7/2020 | Nishimiya et al. |
| 2020/0231654 | A1 | 7/2020 | Yano et al. |
| 2020/0377573 | A1 | 12/2020 | Nishimiya et al. |
| 2021/0032313 | A1 | 2/2021 | Nishimiya et al. |

FOREIGN PATENT DOCUMENTS

| EP | 2 883 954 A1 | 6/2015 |
| EP | 3680335 A1 | 7/2020 |
| JP | 2799178 B2 * | 9/1998 | ........... A23L 33/175 |
| WO | 2010/017587 A1 | 2/2010 |
| WO | 2014/024914 A1 | 2/2014 |
| WO | 2018/117244 A1 | 6/2018 |
| WO | 2019049933 A1 | 3/2019 |

OTHER PUBLICATIONS

Kee et al., "Organ clearance of tyrosyl-arginine and its effect on amino acid metabolism in young sheep," Metabolism, 1993, 42(8): 958-966. (Year: 1993).*
JP 2799178 Google Patent English translation, pp. 1-5. 1998. (Year: 1998).*
"Anti-SPINK2 (Product Datasheet)," Product No. HPA026813, Atlas Antibodies AB, 1 page, available at least as early as Dec. 2012.
Brattsand, M., et al., "SPINK9: A Selective, Skin-Specific Kazal-Type Serine Protease Inhibitor," Journal of Investigative Dermatology 129:1656-1665, 2009.
Canadian Office Action dated Feb. 23, 2021, issued in corresponding Application No. 3,075,251, filed on Sep. 6, 2018, 5 pages.
Diego Magno Assis, et al., "Novel Inhibitory Activity for Serine Protease Inhibitor Kazal Type-3 (Spink3) on Human Recombinant Kallikreins," Protein and Peptide Letters, Aug. 1, 2013, vol. 20, No. 10, pp. 1098-1107.
European Patent Office, Partial Supplemental European Search Report issued in European Application No. 18852892.1, Aug. 3, 2021, 20 pages.
Kherraf, Z.-E., et al., "SPINK2 Deficiency Causes Infertility by Inducing Sperm Defects in Heterozygotes and Azoospermia in Homozygotes," EMBO Molecular Medicine 9(8):1132-1149, May 2017.
International Search Report dated Dec. 4, 2018, issued in corresponding International Application No. PCT/JP2018/033037, filed Sep. 6, 2018, 3 pages.
"PrEST Antigen SPINK2" (Product Datasheet), Product No. APrEST70767, Atlas Antibodies AB, 1 page, available at least as early as Dec. 2012.
Sexton, D.J., et al., "Specific Inhibition of Tissue Kallikrein 1 With a Human Monoclonal Antibody Reveals a Potential Role in Airway Diseases," Biochemical Journal 422:383-392, 2009.
"SPINK2 (Anti-SPINK2 Antibody)," Jun. 28, 2018, <https://www.funakoshi.co.jp/contents/15654> [retrieved Nov. 21, 2018], in particular, "Antigen information," non-official translation (Funakoshi, AntiSPINK2 Antibody—Antibody for immunostaining human tissues [online], Web page No. 15654).
Yampolksy et al., "The Exchangeability of Amino Acids in Proteins," Genetics, 2005, 170: 1459-1472.

\* cited by examiner

*Primary Examiner* — Julie Ha
(74) *Attorney, Agent, or Firm* — Christensen O'Connor Johnson Kindness PLLC

(57) ABSTRACT

A novel peptide which comprises an amino acid sequence represented by SEQ ID NO: 23, and specifically inhibits the protease activity of a target molecule.

23 Claims, 19 Drawing Sheets

Specification includes a Sequence Listing.

```
hKLK1    1   ------------MFLVLCLALSLGGTGAAPPIQSRIVGGWECEQHSQPWQAALYHFSTFQC     50
hKLK4    1   ------MATAGNPWGWFLGYLILGVAGSLVSGSCSQIINGEDCSPHSQPWQALVMENELFC     56
hKLK8    1   MGRPRPRAAKTWMFLILLGGAWAGHSRAQ--EDKVLGGHECQPHSQPWQAAIFQGQQLLC    58 hKLK1    51  GGILVHRQWVLTAAHCISDNYQLWLGRHNLFDDENTA-QFVHVSESFPHPGFNMSLLENH   109
hKLK4    57  SVLVHPQWVLSAAHCFQNSYTIGLGLHSLEADQEPGSQMVEASLSVRHPEYNRPLLAN-   115
hKLK8    59  GVLVGGNWVLTAAHCKKPKYTVRLGDHSLQNKDGPE-QEIPVVQSIPHPCYNSSDVEDH   117 hKLK1    110 TRQADEDYSHDLMLLRLTEPADTITDAVKVVELPTEEPEVGSTCLASGWGSIEPENFSFP   169
hKLK4    116 -------DIMLIKLDESV-SESDTIRSISIASQCPTAGNSCLVSGWGLLANGR--MP    162
hKLK8    118 -------NDLMLLQLRDQA-SLGSKVKPISLADHCTQPPQKCTVSGWGTVTSPRENFP   168 hKLK1    170 DDLQCVDLKILPNDECKKAHVQKVTDFMLCVGHLEGGKDTCVGDSGGPLMCDGVLQGVTS   229
hKLK4    163 TVLQCVNISVVSEEVCSKLYDPLYHPSMFCAGGGHDQKDSCNGDSGGPLICNGYLQGLVS   222
hKLK8    169 DTLNCAEVKIFPQKKCEDAYPGQITDGMVCAGSSKGA-DTCQGDSGGPIVDGALQGITS   227 hKLK1    230 WGYVPCGTPNKPSVAVRVLSYVKWIEDTIAENS              SEQ. ID NO:2      262
hKLK4    223 FGKAPCGQVGVPGVYTNLCKFTEWIEKTVQAS-              SEQ. ID NO:3      254
hKLK8    228 WGSDPCGRSDKPGVYTNICRYLDWIKKIIGSKG              SEQ. ID NO:4      260
```

*FIG. 1*

| ID | IC50 (nM) | | |
|---|---|---|---|
| | KLK1 | KLK4 | KLK8 |
| K10061 | 13±2 | >1,000 | >1,000 |
| K10062 | 12±2 | >1,000 | >1,000 |
| K10066 | 12±2 | >1,000 | >1,000 |
| K10071 | 20±4 | >1,000 | >1,000 |
| K40001 | >1,000 | 1.8±1.0 | >1,000 |
| K40003 | >1,000 | 1.8±1.0 | >1,000 |
| K40004 | >1,000 | 2.1±1.4 | >1,000 |
| K40005 | >1,000 | 2.2±1.5 | >1,000 |
| K41021 | >1,000 | 53±11 | 7.5±2.2 |
| K41024 | >1,000 | 293±52 | 8.0±2.9 |
| K41025 | >1,000 | 86±11 | 17±13 |
| K41026 | >1,000 | 293±50 | 9.1±2.3 |
| K41041 | >1,000 | 2.7±0.3 | 11.4±0.1 |
| K41042 | >1,000 | 15.7±4.2 | 17.5±6.5 |
| K41043 | >1,000 | 1.9±0.1 | 5.3±0.1 |
| K41045 | >1,000 | 2.3±0.4 | 114±15 |
| K41046 | >1,000 | 2.0±0.8 | 283±77 |
| K41047 | >1,000 | 7.4±2.6 | 31.5±8.0 |

*FIG. 2*

| ID | Ki (nM) |
|---|---|
| K40001 | 0.16±0.03 |
| K40003 | 0.20±0.05 |
| K40004 | 0.38±0.18 |
| K40005 | 0.21±0.07 |
| K41021 | 10.7±0.2 |
| K41024 | 74.6±7.1 |
| K41025 | 16.3±1.6 |
| K41026 | 69.3±2.4 |
| K41041 | 0.40±0.06 |
| K41042 | 2.80±0.27 |
| K41043 | 0.21±0.02 |
| K41045 | 0.32±0.09 |
| K41046 | 0.31±0.05 |
| K41047 | 1.38±0.17 |

*FIG. 3*

| ID | $K_{on}$ (M$^{-1}$ s$^{-1}$) | $K_{off}$ (s$^{-1}$) | $K_D$ (M) |
|---|---|---|---|
| K40001 | $6.99 \times 10^6$ | $1.45 \times 10^{-5}$ | $2.08 \times 10^{-12}$ |
| K40003 | $4.40 \times 10^6$ | $1.02 \times 10^{-4}$ | $2.32 \times 10^{-11}$ |
| K41043 | $1.16 \times 10^7$ | $1.03 \times 10^{-4}$ | $8.91 \times 10^{-12}$ |

*FIG. 5*

Human SPINK2

DPQFGLFSKYRTPNCSQYRLPGCPRHFNPVCGSDMSTYAN
ECTLCMKIREGGHNIKIIRNGPC (SEQ ID NO: 1)

FIG. 7

Human KLK1

IVGGWECEQHSQPWQAALYHFSTFQCGGILVHRQWVLTAA
HCISDNYQLWLGRHNLFDDENTAQFVHVSESFPHPGFNMS
LLENHTRQADEDYSHDLMLLRLTEPADTITDAVKVVELPT
EEPEVGSTCLASGWGSIEPENFSFPDDLQCVDLKILPNDE
CKKAHVQKVTDFMLCVGHLEGGKDTCVGDSGGPLMCDGVL
QGVTSWGYVPCGTPNKPSVAVRVLSYVKWIEDTIAENS (SEQ ID NO: 2)

FIG. 8

Human KLK4

I I N G E D C S P H S Q P W Q A A L V M E N E L F C S G V L V H P Q W V L S A A
H C F Q N S Y T I G L G L H S L E A D Q E P G S Q M V E A S L S V R H P E Y N R
P L L A N D L M L I K L D E S V S E S D T I R S I S I A S Q C P T A G N S C L V
S G W G L L A N G R M P T V L Q C V N V S V V S E E V C S K L Y D P L Y H P S M
F C A G G G H D Q K D S C N G D S G G P L I C N G Y L Q G L V S F G K A P C G Q
V G V P G V Y T N L C K F T E W I E K T V Q A S (SEQ ID NO: 3)

FIG. 9

Human KLK8

V L G G H E C Q P H S Q P W Q A A L F Q G Q Q L L C G G V L V G G N W V L T A A
H C K K P K Y T V R L G D H S L Q N K D G P E Q E I P V V Q S I P H P C Y N S S
D V E D H N H D L M L L Q L R D Q A S L G S K V K P I S L A D H C T Q P G Q K C
T V S G W G T V T S P R E N F P D T L N C A E V K I F P Q K K C E D A Y P G Q I
T D G M V C A G S S K G A D T C Q G D S G G P L V C D G A L Q G I T S W G S D P
C G R S D K P G V Y T N I C R Y L D W I K K I I G S K G (SEQ ID NO: 4)

FIG. 10

KLK1 inhibitory peptide K10061

D P Q F G L F S K Y R T P N C A R N N I V D C F Y Y Y K P V C G S D M S T Y A N
E C T L C M K I R E G G H N I K I I R N G P C (SEQ ID NO: 5)

FIG. 11

KLK1 inhibitory peptide K10062

D P Q F G L F S K Y R T P N C D I Y Q V D R C W W A S Q P V C G S D M S T Y A N
E C T L C M K I R E G G H N I K I I R N G P C (SEQ ID NO: 6)

FIG. 12

KLK1 inhibitory peptide K10066

D P Q F G L F S K Y R T P N C S V A L R D I C W W T S E P V C G S D M S T Y A N
E C T L C M K I R E G G H N I K I I R N G P C (SEQ ID NO: 7)

FIG. 13

KLK1 inhibitory peptide K10071

DPQFGLFSKYRTPNCDQNKYRDCHYYYKPVCGSDMSTYAN
ECTLCMKIREGGHNIKIIRNGPC (SEQ ID NO: 8)

*FIG. 14*

KLK4 inhibitory peptide K40001

DPQFGLFSKYRTPNCRKYEYGVCQRTYLPVCGSDMSTYAN
ECTLCMKIREGGHNIKIIRNGPC (SEQ ID NO: 9)

*FIG. 15*

KLK4 inhibitory peptide K40003

DPQFGLFSKYRTPNCELYVEDVCQRIFKPVCGSDMSTYAN
ECTLCMKIREGGHNIKIIRNGPC (SEQ ID NO: 10)

*FIG. 16*

KLK4 inhibitory peptide K40004

DPQFGLFSKYRTPNCEHAQLGVCQKLYQPVCGSDMSTYAN
ECTLCMKIREGGHNIKIIRNGPC (SEQ ID NO: 11)

FIG. 17

KLK4 inhibitory peptide K40005

DPQFGLFSKYRTPNCSQQAMGACQRIYKPVCGSDMSTYAN
ECTLCMKIREGGHNIKIIRNGPC (SEQ ID NO: 12)

FIG. 18

KLK4/KLK8 inhibitory peptide K41021

DPQFGLFSKYRTPNCRKHTLDGCARIYDPVCGSDMSTYAN
ECTLCMKIREGGHNIKIIRNGPC (SEQ ID NO: 13)

FIG. 19

KLK4/KLK8 inhibitory peptide K41024

D P Q F G L F S K Y R T P N C T R Y V V N G C S R V Y D P V C G S D M S T Y A N
E C T L C M K I R E G G H N I K I I R N G P C (SEQ ID NO: 14)

FIG. 20

KLK4/KLK8 inhibitory peptide K41025

D P Q F G L F S K Y R T P N C S R Y K S G G C T R I F D P V C G S D M S T Y A N
E C T L C M K I R E G G H N I K I I R N G P C (SEQ ID NO: 15)

FIG. 21

KLK4/KLK8 inhibitory peptide K41026

D P Q F G L F S K Y R T P N C Q R Y K M R G C N R M Y D P V C G S D M S T Y A N
E C T L C M K I R E G G H N I K I I R N G P C (SEQ ID NO: 16)

FIG. 22

KLK4/KLK8 inhibitory peptide K41041

D P Q F G L F S K Y R T P N C Q R Y S Q W G C T R Q L D P V C G S D M S T Y A N E C T L C M K I R E G G H N I K I I R N G P C (SEQ ID NO: 17)

FIG. 23

KLK4/KLK8 inhibitory peptide K41042

D P Q F G L F S K Y R T P N C S R Y R R E G C N R M Y N P V C G S D M S T Y A N E C T L C M K I R E G G H N I K I I R N G P C (SEQ ID NO: 18)

FIG. 24

KLK4/KLK8 inhibitory peptide K41043

D P Q F G L F S K Y R T P N C R R Y S I H G C N R M Y A P V C G S D M S T Y A N E C T L C M K I R E G G H N I K I I R N G P C (SEQ ID NO: 19)

FIG. 25

KLK4/KLK8 inhibitory peptide K41045

DPQFGLFSKYRTPNCRKQYWVGCNRMYAPVCGSDMSTYAN
ECTLCMKIREGGHNIKIIRNGPC (SEQ ID NO: 20)

*FIG. 26*

KLK4/KLK8 inhibitory peptide K41046

DPQFGLFSKYRTPNCGRYYRGWCFKSLEPVCGSDMSTYAN
ECTLCMKIREGGHNIKIIRNGPC (SEQ ID NO: 21)

*FIG. 27*

KLK4/KLK8 inhibitory peptide K41047

DPQFGLFSKYRTPNCMRFHKDGCARIYDPVCGSDMSTYAN
ECTLCMKIREGGHNIKIIRNGPC (SEQ ID NO: 22)

*FIG. 28*

General formula $X_1$PQFGLFSKYRTPNC$X_2$$X_3$$X_4$$X_5$$X_6$$X_7$$X_8$C$X_9$$X_{10}$$X_{11}$$X_{12}$$X_{13}$PVCGSDMSTYANECTLCMKIREGGHNIKIRNGPC (SEQ ID NO: 23)

FIG. 29

Primer 1

AAAAGAATTCTGATCCGCAGTTTGGTCTGTTTAG (SEQ ID NO: 24)

FIG. 30

Primer 2

AAAACTCGAGTTATGCGGCCGCAGACGCCGCACGGACC (SEQ ID NO: 25)

FIG. 31

Stag + linker 1

GSGMKETAAAKFERQHMDSPDLGTDDDDKAMADIGSANS (SEQ ID NO: 26)

FIG. 32

C-terminal 6-mer

GASAAA (SEQ ID NO: 27)

FIG. 33

Human IgG1 Fc

DKTHTCPPCPAPELLGGPSVFLFPPKPKDTLMISRTPEVT
CVVVDVSHEPEVKFNWYVDGVEVHNAKTKPREEQYNSTYR
VVSVLTVLHQDWLNGKEYCKVSNKALPAPIEKTISKAKGQ
PREPQVYTLPPSREEMTKNQVSLTCLVGFYPSDIAVEWES
NGQPENNYKTTPPVLDSDGSFFLYSKLTVDKSRWQQNVFS
CSVMHEALHNHYTQKSLSLSPGK (SEQ ID NO: 28)

FIG. 34

SEQUENCE LISTING

```
<160> NUMBER OF SEQ ID NOS: 31

<210> SEQ ID NO 1
<211> LENGTH: 63
<212> TYPE: PRT
<213> ORGANISM: Homo sapiens

<400> SEQUENCE: 1

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Arg Asn Gly Pro Cys
    50                  55                  60

<210> SEQ ID NO 2
<211> LENGTH: 238
<212> TYPE: PRT
<213> ORGANISM: Homo sapiens

<400> SEQUENCE: 2

Ile Val Gly Gly Trp Glu Cys Glu Gln His Ser Gln Pro Trp Gln Ala
1               5                   10                  15

Ala Leu Tyr His Phe Ser Thr Phe Gln Cys Gly Gly Ile Leu Val His
            20                  25                  30

Arg Gln Trp Val Leu Thr Ala Ala His Cys Ile Ser Asp Asn Tyr Gln
        35                  40                  45

Leu Trp Leu Gly Arg His Asn Leu Phe Asp Asp Glu Asn Thr Ala Gln
    50                  55                  60

Phe Val His Val Ser Glu Ser Phe Pro His Pro Gly Phe Asn Met Ser
65                  70                  75                  80

Leu Leu Glu Asn His Thr Arg Gln Ala Asp Glu Asp Tyr Ser His Asp
                85                  90                  95

Leu Met Leu Leu Arg Leu Thr Glu Pro Ala Asp Thr Ile Thr Asp Ala
            100                 105                 110

Val Lys Val Val Glu Leu Pro Thr Glu Glu Pro Glu Val Gly Ser Thr
        115                 120                 125

Cys Leu Ala Ser Gly Trp Gly Ser Ile Glu Pro Glu Asn Phe Ser Phe
    130                 135                 140

Pro Asp Asp Leu Gln Cys Val Asp Leu Lys Ile Leu Pro Asn Asp Glu
145                 150                 155                 160

Cys Lys Lys Ala His Val Gln Lys Val Thr Asp Phe Met Leu Cys Val
                165                 170                 175

Gly His Leu Glu Gly Gly Lys Asp Thr Cys Val Gly Asp Ser Gly Gly
            180                 185                 190
```

```
Pro Leu Met Cys Asp Gly Val Leu Gln Gly Val Thr Ser Trp Gly Tyr
        195                 200                 205

Val Pro Cys Gly Thr Pro Asn Lys Pro Ser Val Ala Val Arg Val Leu
210                 215                 220

Ser Tyr Val Lys Trp Ile Glu Asp Thr Ile Ala Glu Asn Ser
225                 230                 235

<210> SEQ ID NO 3
<211> LENGTH: 224
<212> TYPE: PRT
<213> ORGANISM: Homo sapiens

<400> SEQUENCE: 3

Ile Ile Asn Gly Glu Asp Cys Ser Pro His Ser Gln Pro Trp Gln Ala
1               5                   10                  15

Ala Leu Val Met Glu Asn Glu Leu Phe Cys Ser Gly Val Leu Val His
                20                  25                  30

Pro Gln Trp Val Leu Ser Ala Ala His Cys Phe Gln Asn Ser Tyr Thr
            35                  40                  45

Ile Gly Leu Gly Leu His Ser Leu Glu Ala Asp Gln Glu Pro Gly Ser
        50                  55                  60

Gln Met Val Glu Ala Ser Leu Ser Val Arg His Pro Glu Tyr Asn Arg
65                  70                  75                  80

Pro Leu Leu Ala Asn Asp Leu Met Leu Ile Lys Leu Asp Glu Ser Val
                85                  90                  95

Ser Glu Ser Asp Thr Ile Arg Ser Ile Ser Ile Ala Ser Gln Cys Pro
            100                 105                 110

Thr Ala Gly Asn Ser Cys Leu Val Ser Gly Trp Gly Leu Leu Ala Asn
        115                 120                 125

Gly Arg Met Pro Thr Val Leu Gln Cys Val Asn Val Ser Val Val Ser
130                 135                 140

Glu Glu Val Cys Ser Lys Leu Tyr Asp Pro Leu Tyr His Pro Ser Met
145                 150                 155                 160

Phe Cys Ala Gly Gly Gly His Asp Gln Lys Asp Ser Cys Asn Gly Asp
                165                 170                 175

Ser Gly Gly Pro Leu Ile Cys Asn Gly Tyr Leu Gln Gly Leu Val Ser
            180                 185                 190

Phe Gly Lys Ala Pro Cys Gly Gln Val Gly Val Pro Gly Val Tyr Thr
        195                 200                 205

Asn Leu Cys Lys Phe Thr Glu Trp Ile Glu Lys Thr Val Gln Ala Ser
210                 215                 220

<210> SEQ ID NO 4
<211> LENGTH: 228
<212> TYPE: PRT
<213> ORGANISM: Homo sapiens

<400> SEQUENCE: 4

Val Leu Gly Gly His Glu Cys Gln Pro His Ser Gln Pro Trp Gln Ala
1               5                   10                  15

Ala Leu Phe Gln Gly Gln Gln Leu Leu Cys Gly Gly Val Leu Val Gly
                20                  25                  30

Gly Asn Trp Val Leu Thr Ala Ala His Cys Lys Lys Pro Lys Tyr Thr
            35                  40                  45

Val Arg Leu Gly Asp His Ser Leu Gln Asn Lys Asp Gly Pro Glu Gln
        50                  55                  60
```

```
Glu Ile Pro Val Val Gln Ser Ile Pro His Pro Cys Tyr Asn Ser Ser
 65                  70                  75                  80

Asp Val Glu Asp His Asn His Asp Leu Met Leu Leu Gln Leu Arg Asp
                 85                  90                  95

Gln Ala Ser Leu Gly Ser Lys Val Lys Pro Ile Ser Leu Ala Asp His
            100                 105                 110

Cys Thr Gln Pro Gly Gln Lys Cys Thr Val Ser Gly Trp Gly Thr Val
        115                 120                 125

Thr Ser Pro Arg Glu Asn Phe Pro Asp Thr Leu Asn Cys Ala Glu Val
    130                 135                 140

Lys Ile Phe Pro Gln Lys Lys Cys Glu Asp Ala Tyr Pro Gly Gln Ile
145                 150                 155                 160

Thr Asp Gly Met Val Cys Ala Gly Ser Ser Lys Gly Ala Asp Thr Cys
                165                 170                 175

Gln Gly Asp Ser Gly Gly Pro Leu Val Cys Asp Gly Ala Leu Gln Gly
            180                 185                 190

Ile Thr Ser Trp Gly Ser Asp Pro Cys Gly Arg Ser Asp Lys Pro Gly
        195                 200                 205

Val Tyr Thr Asn Ile Cys Arg Tyr Leu Asp Trp Ile Lys Lys Ile Ile
    210                 215                 220

Gly Ser Lys Gly
225

<210> SEQ ID NO 5
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 5

Asp Pro Gln Phe Gly Leu Phe Ser Lys Tyr Arg Thr Pro Asn Cys Ala
1               5                   10                  15

Arg Asn Asn Ile Val Asp Cys Phe Tyr Tyr Lys Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 6
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 6

Asp Pro Gln Phe Gly Leu Phe Ser Lys Tyr Arg Thr Pro Asn Cys Asp
1               5                   10                  15

Ile Tyr Gln Val Asp Arg Cys Trp Trp Ala Ser Gln Pro Val Cys Gly
            20                  25                  30
```

```
Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 7
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 7

Asp Pro Gln Phe Gly Leu Phe Ser Lys Tyr Arg Thr Pro Asn Cys Ser
1               5                   10                  15

Val Ala Leu Arg Asp Ile Cys Trp Trp Thr Ser Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 8
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 8

Asp Pro Gln Phe Gly Leu Phe Ser Lys Tyr Arg Thr Pro Asn Cys Asp
1               5                   10                  15

Gln Asn Lys Tyr Arg Asp Cys His Tyr Tyr Lys Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 9
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 9

Asp Pro Gln Phe Gly Leu Phe Ser Lys Tyr Arg Thr Pro Asn Cys Arg
1               5                   10                  15

Lys Tyr Glu Tyr Gly Val Cys Gln Arg Thr Tyr Leu Pro Val Cys Gly
            20                  25                  30
```

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
        50                  55                  60

<210> SEQ ID NO 10
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 10

Asp Pro Gln Phe Gly Leu Phe Ser Lys Tyr Arg Thr Pro Asn Cys Glu
1               5                   10                  15

Leu Tyr Val Glu Asp Val Cys Gln Arg Ile Phe Lys Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
        50                  55                  60

<210> SEQ ID NO 11
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 11

Asp Pro Gln Phe Gly Leu Phe Ser Lys Tyr Arg Thr Pro Asn Cys Glu
1               5                   10                  15

His Ala Gln Leu Gly Val Cys Gln Lys Leu Tyr Gln Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
        50                  55                  60

<210> SEQ ID NO 12
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 12

Asp Pro Gln Phe Gly Leu Phe Ser Lys Tyr Arg Thr Pro Asn Cys Ser
1               5                   10                  15

Gln Gln Ala Met Gly Ala Cys Gln Arg Ile Tyr Lys Pro Val Cys Gly
            20                  25                  30

Ser Asp Met Ser Thr Tyr Ala Asn Glu Cys Thr Leu Cys Met Lys Ile

```
                35                  40                  45
Arg Glu Gly Gly His Asn Ile Lys Ile Ile Arg Asn Gly Pro Cys
    50                  55                  60

<210> SEQ ID NO 13
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 13

Asp Pro Gln Phe Gly Leu Phe Ser Lys Tyr Arg Thr Pro Asn Cys Arg
1               5                   10                  15

Lys His Thr Leu Asp Gly Cys Ala Arg Ile Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 14
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 14

Asp Pro Gln Phe Gly Leu Phe Ser Lys Tyr Arg Thr Pro Asn Cys Thr
1               5                   10                  15

Arg Tyr Val Val Asn Gly Cys Ser Arg Val Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 15
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 15

Asp Pro Gln Phe Gly Leu Phe Ser Lys Tyr Arg Thr Pro Asn Cys Ser
1               5                   10                  15

Arg Tyr Lys Ser Gly Gly Cys Thr Arg Ile Phe Asp Pro Val Cys Gly
            20                  25                  30

Ser Asp Met Ser Thr Tyr Ala Asn Glu Cys Thr Leu Cys Met Lys Ile
        35                  40                  45
```

Arg Glu Gly Gly His Asn Ile Lys Ile Ile Arg Asn Gly Pro Cys
        50                  55                  60

<210> SEQ ID NO 16
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 16

Asp Pro Gln Phe Gly Leu Phe Ser Lys Tyr Arg Thr Pro Asn Cys Gln
1               5                   10                  15

Arg Tyr Lys Met Arg Gly Cys Asn Arg Met Tyr Asp Pro Val Cys Gly
                20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
        50                  55                  60

<210> SEQ ID NO 17
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 17

Asp Pro Gln Phe Gly Leu Phe Ser Lys Tyr Arg Thr Pro Asn Cys Gln
1               5                   10                  15

Arg Tyr Ser Gln Trp Gly Cys Thr Arg Gln Leu Asp Pro Val Cys Gly
                20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
        50                  55                  60

<210> SEQ ID NO 18
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 18

Asp Pro Gln Phe Gly Leu Phe Ser Lys Tyr Arg Thr Pro Asn Cys Ser
1               5                   10                  15

Arg Tyr Arg Arg Glu Gly Cys Asn Arg Met Tyr Asn Pro Val Cys Gly
                20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys
    50                  55                  60

<210> SEQ ID NO 19
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 19

Asp Pro Gln Phe Gly Leu Phe Ser Lys Tyr Arg Thr Pro Asn Cys Arg
1               5                   10                  15

Arg Tyr Ser Ile His Gly Cys Asn Arg Met Tyr Ala Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 20
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 20

Asp Pro Gln Phe Gly Leu Phe Ser Lys Tyr Arg Thr Pro Asn Cys Arg
1               5                   10                  15

Lys Gln Tyr Trp Val Gly Cys Asn Arg Met Tyr Ala Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 21
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 21

Asp Pro Gln Phe Gly Leu Phe Ser Lys Tyr Arg Thr Pro Asn Cys Gly
1               5                   10                  15

Arg Tyr Tyr Arg Gly Trp Cys Phe Lys Ser Leu Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys 50          55          60

<210> SEQ ID NO 22
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(63)
<223> OTHER INFORMATION: binder

<400> SEQUENCE: 22

Asp Pro Gln Phe Gly Leu Phe Ser Lys Tyr Arg Thr Pro Asn Cys Met
1               5                   10                  15

Arg Phe His Lys Asp Gly Cys Ala Arg Ile Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 23
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (1)..(63)
<223> OTHER INFORMATION: mutants
<220> FEATURE:
<221> NAME/KEY: MISC_FEATURE
<222> LOCATION: (16)..(22)
<223> OTHER INFORMATION: Xaa can be any naturally occurring amino acid
<220> FEATURE:
<221> NAME/KEY: MISC_FEATURE
<222> LOCATION: (24)..(28)
<223> OTHER INFORMATION: Xaa can be any naturally occurring amino acid

<400> SEQUENCE: 23

Xaa Pro Gln Phe Gly Leu Phe Ser Lys Tyr Arg Thr Pro Asn Cys Xaa
1               5                   10                  15

Xaa Xaa Xaa Xaa Xaa Xaa Cys Xaa Xaa Xaa Xaa Xaa Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 24
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: primer

<400> SEQUENCE: 24

```
aaaactcgag ttatgcggcc gcagacgcgc cgcacggacc                    40
```

<210> SEQ ID NO 25
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: primer

<400> SEQUENCE: 25

```
aaaagaattc tgatccgcag tttggtctgt ttag                          34
```

<210> SEQ ID NO 26
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(39)
<223> OTHER INFORMATION: oligo peptide

<400> SEQUENCE: 26

Gly Ser Gly Met Lys Glu Thr Ala Ala Ala Lys Phe Glu Arg Gln His
1               5                   10                  15

Met Asp Ser Pro Asp Leu Gly Thr Asp Asp Asp Asp Lys Ala Met Ala
            20                  25                  30

Asp Ile Gly Ser Ala Asn Ser
        35

<210> SEQ ID NO 27
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: oligo peptide

<400> SEQUENCE: 27

Gly Ala Ser Ala Ala Ala
1               5

<210> SEQ ID NO 28
<211> LENGTH: 223
<212> TYPE: PRT
<213> ORGANISM: Homo sapiens

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Pro Glu Val Lys Phe Asn Trp Tyr Val Asp Gly Val Glu Val His
    50                  55                  60

```
Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                 85                  90                  95

Glu Tyr Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

```
<210> SEQ ID NO 29
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      succinate of leucine (Leu)
<220> FEATURE:
<221> NAME/KEY: MISC_FEATURE
<222> LOCATION: (4)..(4)
<223> OTHER INFORMATION: Wherein X at position 4 is defined as
      7-methoxycoumarin acetic acid of tyrosine (Tyr)

<400> SEQUENCE: 29

Xaa Leu Val Xaa
1

<210> SEQ ID NO 30
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as methyl
      succinate of alanine (Ala)
<220> FEATURE:
<221> NAME/KEY: MISC_FEATURE
<222> LOCATION: (4)..(4)
<223> OTHER INFORMATION: Wherein X at position 4 is defined as
      7-methoxycoumarin acetic acid of valine (Val)

<400> SEQUENCE: 30

Xaa Ala Pro Xaa
1

<210> SEQ ID NO 31
<211> LENGTH: 4
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      butoxycarbamate of leucine (Leu)
<220> FEATURE:
<221> NAME/KEY: MISC_FEATURE
<222> LOCATION: (4)..(4)
<223> OTHER INFORMATION: Wherein X at position 4 is defined as
      7-methoxycoumarin acetic acid of arginine (Arg)

<400> SEQUENCE: 31

Xaa Ser Thr Xaa
1
```

PEPTIDES INHIBITING KLK1, KLK4, OR KLK4 AND KLK8

CROSS-REFERENCE TO RELATED APPLICATIONS

This application is a continuation of U.S. application Ser. No. 16/642,885, filed Feb. 27, 2020, which is a national stage application based on PCT/JP2018/033037, filed Sep. 6, 2018, which claims the priority from JP Application No. 2017-171776, filed Sep. 7, 2017, each expressly incorporated herein by reference in its entirety.

TECHNICAL FIELD

The present invention relates to peptides, polynucleotides, vectors, cells, methods for producing peptides, peptides obtained by such methods, conjugates containing the peptides and another moiety bound thereto, compositions containing the peptides or conjugates, pharmaceutical compositions containing the peptides or conjugates, the pharmaceutical compositions containing the peptides or conjugates for the treatment or prevention of various diseases, uses of the peptides or conjugates for treating or preventing various diseases, methods for treating various diseases including a step of administering the peptides or conjugates, compositions containing the peptides or conjugates for diagnosis or testing for various diseases, and the like.

BACKGROUND ART

It is known that KLK1 is composed of an N-terminal propeptide and a protease active domain and has three N-type sugar chain additions (Non Patent Literature 1). KLK1 exhibits trypsin-like and chymotrypsin-like protease activities and has a high kininogen degrading activity among the kallikrein families. After it is cleaved, KLK1 is involved in the regulation of blood pressure in blood, and affects various transporters such as $H^+$-ATPase and $K^+$-ATPase in kidney and heart disease systems (Non Patent Literature 2). In respiratory tracts, kinin produced by the degradation of kininogen by KLK1 activates the Bradykinin B2 receptor, and induces smooth muscle contraction of the trachea and excessive secretion of mucus. Furthermore, KLK1 has been suggested to be a therapeutic target for asthma, since an association between increased KLK1 activity, and elevation of IL-8 and free bradykinin has been reported. So far, the effects of low molecular weight KLK1 inhibitors have been verified in models such as acute pancreatitis and bronchitis, but the pharmaceutical efficacy or specificity of these drugs has not been sufficient. In recent years, KLK1-inhibiting drugs using human monoclonal antibodies have been reported, and it has become clear that such drugs exhibit pharmaceutical efficacy in a sheep asthma model (Non Patent Literature 3). However, other than antibodies or fragments thereof, low molecular weight proteins (for example, proteins not containing an immunoglobulin variable region) which show KLK1-specific inhibitory activity are not known.

It is known that KLK4 consists of an N-terminal propeptide and a trypsin-like domain having protease activity and has an N-type sugar chain addition. KLK4 is secreted during tooth enamel formation and becomes activated KLK4 through cleavage of the N-terminal propeptide by MMP20 (Matrix Metalloproteinase 20) (Non Patent Literature 1). Activated KLK4 is involved in promoting the maturation of an enamel layer mainly composed of hydroxyapatite crystals by decomposing enamel matrix components such as amelogenin and enamelin (Non Patent Literature 2). In addition, when siRNA against KLK4 was administered to prostate cancer transplanted mice, tumor growth suppression was observed, suggesting an association of KLK4 with prostate cancer. Modified peptides from Sunflower trypsin inhibitor (SFTI) and the like have been reported to date as KLK4 inhibitors, showing pharmaceutical efficacy in combination with Paclitaxel in cancer cell lines, although it is difficult to say whether their efficacy is sufficient (Patent Literatures 1 and 2, and Non Patent Literature 4). Also, in nature, human serine protease of Kazal-type 6 (SPINK6) has KLK4 inhibitory activity and exhibits a Ki of 27 nM for KLK4, while exhibiting a Ki of 1 nM for KLK12 and KLK13, so the specificity thereof is not high (Non Patent Literature 5). Thus, KLK4-specific inhibitory molecules such as low molecular weight proteins other than antibodies or fragments thereof (for example, proteins not containing an immunoglobulin variable region) are desired.

KLK8 is also called neuropsin, and it is known that KLK8 is composed of an N-terminal propeptide and a trypsin-like domain having protease activity and has an N-type sugar chain addition (Non Patent Literature 1). KLK8 is expressed in the hippocampus, amygdala, limbic system and the like as a pro-form having a propeptide, and becomes activated KLK8 when the propeptide is cleaved by a protease. The activated KLK8 has been reported to be involved in long-term memory enhancement, schizophrenia and the like by cleaving the cell adhesion molecule L1CAM (the presynaptic neural cell adhesion molecule L1), the susceptibility factor for schizophrenia NRG1 (Neuregulin 1) and the like present in the hippocampal presynapse (Non Patent Literature 2). Further, KLK8 has been suggested to be associated with colorectal cancer and ovarian cancer, in which high expression of KLK8 has been observed (Non Patent Literature 6). In nature, human serine protease of Kazal-type 9 (SPINK9) has been reported to have KLK8 inhibitory activity, but its activity is very weak (Non Patent Literature 7). Low molecular weight proteins other than antibodies or fragments thereof (for example, proteins not containing an immunoglobulin variable region) which show KLK8-specific inhibitory activity are not known.

In addition, low molecular weight proteins other than antibodies or fragments thereof (for example, proteins not containing an immunoglobulin variable region) which specifically show inhibitory activity against KLK4 and KLK8 for the purpose of treating KLK4-related disease and KLK8-related disease with a single agent are not known.

The SPINK2 (Serine Protease Inhibitor Kazal-type 2) is a 7 kDa protein composed of a Kazal-type domain having three disulfide bonds. It is expressed in the testis and seminal vesicle in the human body and functions as a trypsin/acrosin inhibitor (Non Patent Literature 8). There are no findings suggesting that SPINK2 itself can be a KLK1, KLK4, or KLK4 and KLK8 dual inhibitor.

CITATION LIST

Patent Literature

Patent Literature 1: WO2010/017587
Patent Literature 2: WO2015/144933

Non Patent Literature

Non Patent Literature 1: Guo S, Skala W, Magdolen V, Brandstetter H, Goettig P. (2014) Sweetened kallikrein-related peptidases (KLKs): glycan trees as potential regulators of activation and activity. Biol Chem. 395(9):959-76.

Non Patent Literature 2: Prassas I, Eissa A, Poda G, Diamandis E P. (2015) Unleashing the therapeutic potential of human kallikrein-related serine proteases. Nat Rev Drug Discov. 14(3):183-202.

Non Patent Literature 3: Sexton D J, Chen T, Martik D, Kuzmic P, Kuang G, Chen J, Nixon A E, Zuraw B L, Forteza R M, Abraham W M, Wood C R. (2009) Specific inhibition of tissue kallikrein 1 with a human monoclonal antibody reveals a potential role in airway diseases. Biochem J. 422(2):383-92.

Non Patent Literature 4: Dong Y, Stephens C, Walpole C, Swedberg J E, Boyle G M, Parsons P G, McGuckin M A, Harris J M, Clements J A. (2013) Paclitaxel resistance and multicellular spheroid formation are induced by kallikrein-related peptidase 4 in serous ovarian cancer cells in an ascites mimicking microenvironment. PLoS One. 8(2):e57056.

Non Patent Literature 5: Kantyka T1, Fischer J, Wu Z, Declercq W, Reiss K, Schroder J M, Meyer-Hoffert U. (2011) Inhibition of kallikrein-related peptidases by the serine protease inhibitor of Kazal-type 6. Peptides. 32(6): 1187-92.

Non Patent Literature 6: Borgono CA1, Diamandis E P. (2004) The emerging roles of human tissue kallikreins in cancer. Nat Rev Cancer. 4(11):876-90.

Non Patent Literature 7: Brattsand M1, Stefansson K, Hubiche T, Nilsson S K, Egelrud T. (2009) SPINK9: a selective, skin-specific Kazal-type serine protease inhibitor. J Invest Dermatol. 129(7):1656-65.

Non Patent Literature 8: Chen T, Lee T R, Liang W G, Chang W S, Lyu P C. (2009) Identification of trypsin-inhibitory site and structure determination of human SPINK2 serine proteinase inhibitor. Proteins. 77(1):209-1.

SUMMARY OF INVENTION

Technical Problem

An object of the present invention is to provide novel KLK1 inhibitory peptides, KLK4 inhibitory peptides, or KLK4 and KLK8 dual inhibitory (hereinafter simply referred to as "KLK4 and KLK8 inhibitory" or "KLK4/KLK8 inhibitory") peptides.

Solution to Problem

The present invention mainly relates to the following.

(1) A SPINK2 mutant peptide which comprises an amino acid sequence represented by SEQ ID NO: 23 (FIG. 29) and specifically inhibits the protease activity of KLK1.

(2) The peptide according to (1), wherein the $1^{st}$ to the $13^{th}$ Xaa ($X_1$ to $X_{13}$) are amino acids other than Cys and Pro.

(3) The peptide according to (1) or (2), wherein the $1^{st}$ Xaa ($X_1$) is Asp or Gly.

(4) The peptide of any one of (1) to (3), wherein the $2^{nd}$ Xaa ($X_2$) is Ala, Asp or Ser, the $3^{rd}$ Xaa ($X_3$) is Ile, Gln, Arg or Val, the $4^{th}$ Xaa ($X_4$) is Ala, Asn or Tyr, the $5^{th}$ Xaa ($X_5$) is Leu, Lys, Asn or Gln, the $6^{th}$ Xaa ($X_6$) is Ile, Arg, Tyr or Val, the $7^{th}$ Xaa ($X_7$) is Asp, Arg or Val, the $8^{th}$ Xaa ($X_8$) is Asp, Ile or Arg, the $9^{th}$ Xaa ($X_9$) is Phe, His or Trp, the $10^{th}$ Xaa ($X_{10}$) is Tyr or Trp, the $11^{th}$ Xaa ($X_{11}$) is Ala, Thr or Tyr, the $12^{th}$ Xaa ($X_{12}$) is Ser or Tyr, and the $13^{th}$ Xaa ($X_{13}$) is Glu, Lys or Gln.

(5) The peptide according to any one of (1) to (4), wherein the peptide comprises an amino acid sequence represented by any one of SEQ ID NOs: 5 to 8 (FIGS. 11 to 14).

(6) A SPINK2 mutant peptide which comprises an amino acid sequence represented by SEQ ID NO: 23 (FIG. 29), and specifically inhibits the protease activity of KLK4.

(7) The peptide according to (6), wherein the 1st to the $13^{th}$ Xaa ($X_1$ to $X_{13}$) are amino acids other than Cys and Pro.

(8) The peptide according to (6) or (7), wherein the $1^{st}$ Xaa ($X_1$) is Asp or Gly.

(9) The peptide of any one of (6) to (8), wherein the $2^{nd}$ Xaa ($X_2$) is Glu, Arg or Ser, the $3^{rd}$ Xaa ($X_3$) is His, Lys, Leu or Gln, the $4^{th}$ Xaa ($X_4$) is Ala, Gln or Tyr, the $5^{th}$ Xaa ($X_5$) is Ala, Glu, Gln or Val, the $6^{th}$ Xaa ($X_6$) is Glu, Leu, Met or Tyr, the $7^{th}$ Xaa ($X_7$) is Asp or Gly, the $8^{th}$ Xaa ($X_8$) is Ala or Val, the $9^{th}$ Xaa ($X_9$) is Gln, the $10^{th}$ Xaa ($X_{10}$) is Lys or Arg, the $11^{th}$ Xaa ($X_{11}$) is Ile, the $12^{th}$ Xaa ($X_{12}$) is Phe or Tyr, and $X_{13}$) is Lys, Leu or Gln.

(10) The peptide according to any one of (6) to (9), wherein the peptide comprises an amino acid sequence represented by any one of SEQ ID NOs: 9 to 12 (FIGS. 15 to 18).

(11) A SPINK2 mutant peptide which comprises an amino acid sequence represented by SEQ ID NO: 23 (FIG. 29), and specifically inhibits the protease activity of KLK4 and the protease activity of KLK8.

(12) The peptide according to (11), wherein the 1st to the $13^{th}$ Xaa ($X_1$ to $X_{13}$) are amino acids other than Cys and Pro.

(13) The peptide according to (11) or (12), wherein the $1^{st}$ Xaa ($X_1$) is Asp or Gly.

(14) The peptide according to any one of (11) to (13), wherein the $2^{nd}$ Xaa ($X_2$) is Gly, Met, Gln, Arg, Ser or Thr, the $3^{rd}$ Xaa ($X_3$) is Lys or Arg, the $4^{th}$ Xaa ($X_4$) is Phe, His, Gln or Tyr, the $5^{th}$ Xaa ($X_5$) is His, Lys, Arg, Ser, Thr, Val or Tyr, the $6^{th}$ Xaa ($X_6$) is Ile, Lys, Leu, Met, Gln, Arg, Ser, Val or Trp, the $7^{th}$ Xaa ($X_7$) is Asp, Glu, Gly, His, Asn, Arg, Val or Trp, the $8^{th}$ Xaa ($X_8$) is Gly or Trp, the $9^{th}$ Xaa ($X_9$) is Ala, Phe, Asn, Ser or Thr, the $10^{th}$ Xaa ($X_{10}$) is Lys or Arg, the $11^{th}$ Xaa ($X_{11}$) is Ile, Met, Gln, Ser or Val, the $12^{th}$ Xaa ($X_{12}$) is Phe, Leu or Tyr, and the $13^{th}$ Xaa ($X_{13}$) is Ala, Asp, Glu or Asn.

(15) The peptide according to any one of (11) to (14), wherein the peptide comprises an amino acid sequence represented by any one of SEQ ID NOs: 13 to 22 (FIGS. 19 to 28).

(16) The peptide according to any one of (1) to (15), wherein the peptide comprises an amino acid sequence comprising:

an amino acid sequence represented by SEQ ID NO: 23 (FIG. 29); and 1 to 3 amino acid residues or an amino acid sequence represented by SEQ ID NO: 26 (FIG. 32), which are added to the amino terminal side of the amino acid sequence represented by SEQ ID NO: 23 (FIG. 29).

(17) The peptide according to any one of (1) to (16), wherein the peptide comprises an amino acid sequence comprising:

an amino acid sequence represented by SEQ ID NO: 23 (FIG. 29); and an amino acid sequence consisting of 1 to 6 amino acids, which are added to the carboxyl terminal side of the amino acid sequence represented by SEQ ID NO: 23 (FIG. 29).

(18) The peptide according to any one of (1) to (17), wherein the peptide has a conformation characterized by comprising three disulfide bonds and further comprising a loop structure, an α-helix and a β-sheet.

(19) A polynucleotide comprising a nucleotide sequence encoding an amino acid sequence contained in the peptide according to any one of (1) to (18).

(20) A vector comprising the polynucleotide according to (19).

(21) A cell which comprises the polynucleotide according to (19) or the vector according to (20), or which produces the peptide according to any one of (1) to (18).

(22) A method for producing a SPINK2 mutant peptide, comprising the following steps (i) and (ii):
(i) culturing the cell according to (21); and
(ii) recovering the SPINK2 mutant peptide from the culture.

(23) A method for producing the peptide according to any one of (1) to (18), comprising a step of preparing the peptide by chemical synthesis or in vitro translation.

(24) A SPINK2 mutant peptide obtained by the method according to (22) or (23).

(25) A conjugate comprising the peptide according to any one of (1) to (18) and (24) and another moiety bound thereto.

(26) The conjugate according to (25), wherein the conjugate is a polypeptide.

(27) The conjugate according to (25) or (26), wherein the conjugate comprises an immunoglobulin Fc region or a functional fragment thereof.

(28) A method for producing the SPINK2 mutant peptide conjugate according to any one of (25) to (27), comprising the following steps (i) and (ii):
(i) culturing a cell containing a polynucleotide comprising a nucleotide sequence encoding an amino acid sequence contained in the conjugate or a vector into which the polynucleotide has been inserted; and
(ii) recovering the SPINK2 mutant peptide conjugate or a peptide moiety contained in the conjugate from the culture.

(29) A method for producing the SPINK2 mutant peptide conjugate according to any one of (25) to (27), comprising a step of preparing the conjugate or a peptide moiety contained in the conjugate by chemical synthesis or in vitro translation.

(30) A SPINK2 mutant peptide conjugate produced by the method according to (28) or (29).

(31) An antibody or a binding fragment thereof which binds to the peptide according to any one of (1) to (18) and (24).

(32) A composition comprising the peptide according to any one of (1) to (18) and (24), the polynucleotide according to (19), the vector according to (20), the cell according to (21), the conjugate according to any one of (25) to (27) and (30), and/or the antibody according to (31) or a binding fragment thereof.

(33) A pharmaceutical composition comprising the peptide according to any one of (1) to (18) and (24), the polynucleotide according to (19), the vector according to (20), the cell according to (21), and/or the conjugate according to any one of (25) to (27) and (30).

(34) The pharmaceutical composition according to (33) for the treatment or prevention of a KLK1-related disease, a KLK4-related disease and/or a KLK8-related disease.

(35) A composition for testing or diagnosis, comprising the peptide according to any one of (1) to (18) and (24), the polynucleotide according to (19), the vector according to (20), the cell according to (21), the conjugate according to any one of (25) to (27) and (30), and/or the antibody according to (31) or a binding fragment thereof.

(36) The method according to (22), (23), (28) or (29), comprising an affinity purification step using the antibody according to (31) or a binding fragment thereof.

Advantageous Effects of Invention

The peptide provided by the present invention or a pharmaceutical composition containing the same has KLK1 inhibitory activity, KLK4 inhibitory activity, or KLK4/KLK8 inhibitory activity, and is useful for the treatment or prevention of a KLK1-related disease, a KLK4-related disease or a KLK4/KLK8-related disease (all described later) and the like.

BRIEF DESCRIPTION OF THE DRAWINGS

FIGS. 4A-1, 4A-2, and 4A-3 are graphs showing an evaluation of cross-reactivity of each inhibitory peptide to each protease, using the degradation of the peptide substrate as an index. For α-chymotrypsin inhibitory activity (FIG. 4A-1), chymotrypsin at the final concentration of 10 nM (Worthington Biochemical Corporation; LS001434), and substrate peptide Suc-LLVT-MCA (SEQ ID NO. 29) at the final concentration of 100 μM (PEPTIDE INSTITUTE, INC.; 3120-v) were used. For human tryptase inhibitory activity (FIG. 4A-2), Tryptase at the final concentration of 1 nM (Sigma-Aldrich Co.; T7063), and substrate peptide Boc-Phe-Ser-Arg-MCA at the final concentration of 100 μM (PEPTIDE INSTITUTE, INC.; 3107-v) were used. For human chymase inhibitory activity (FIG. 4A-3), chymase at the final concentration of 100 nM (Sigma-Aldrich Co.; C8118), and substrate peptide Suc-Leu-Leu-Val-Tyr-MCA (SEQ ID NO. 29) at the final concentration of 100 μM (PEPTIDE INSTITUTE, INC.; 3120-v) were used.

FIGS. 4B-1, 4B-2, and 4B-3 are graphs showing an evaluation of cross-reactivity of each inhibitory peptide to each protease, using the degradation of the peptide substrate as an index. For human plasmin inhibitory activity (FIG. 4B-1), plasmin at the final concentration of 50 nM (Sigma-Aldrich Co.; P1867), and substrate peptide Boc-Val-Leu-Lys-MCA at the final concentration of 100 μM (PEPTIDE INSTITUTE, INC.; 3104-v) were used. For human thrombin inhibitory activity (FIG. 4B-2), thrombin at the final concentration of 1 nM (Sigma-Aldrich Co.; T6884), and substrate peptide Boc-VPR-AMC Fluorogenic Peptide Substrate at the final concentration of 100 μM (R&D Systems, Inc.; ES011) were used. For neutrophil elastase inhibitory activity (FIG. 4B-3), neutrophil elastase at the final concentration of 0.02 U/L (Enzo Life Sciences, Inc.), and substrate peptide Suc(OMe)-Ala-Ala-Pro-Val-MCA (SEQ ID NO. 30)

at the final concentration of 100 μM (PEPTIDE INSTITUTE, INC.; 3153-v) were used.

Figures 1, 4A:
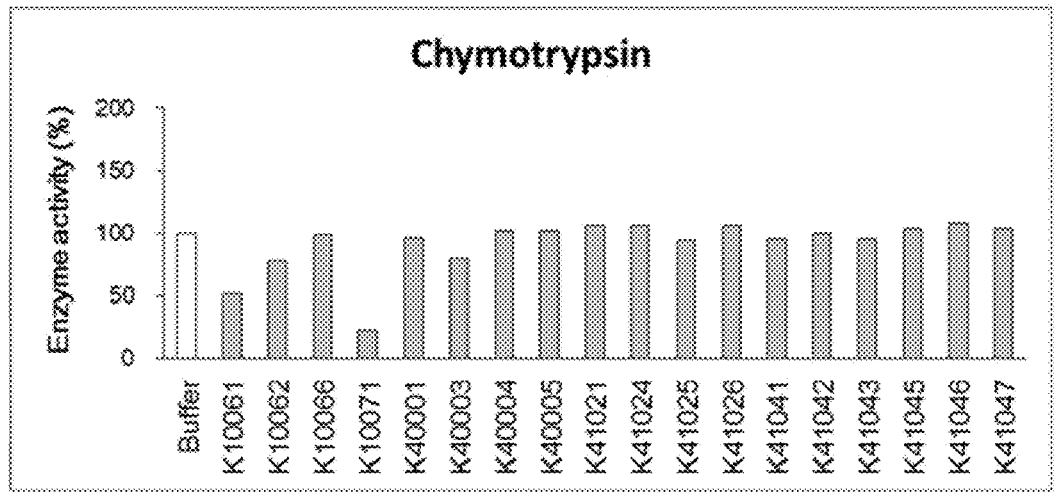
Figures 2, 4A:
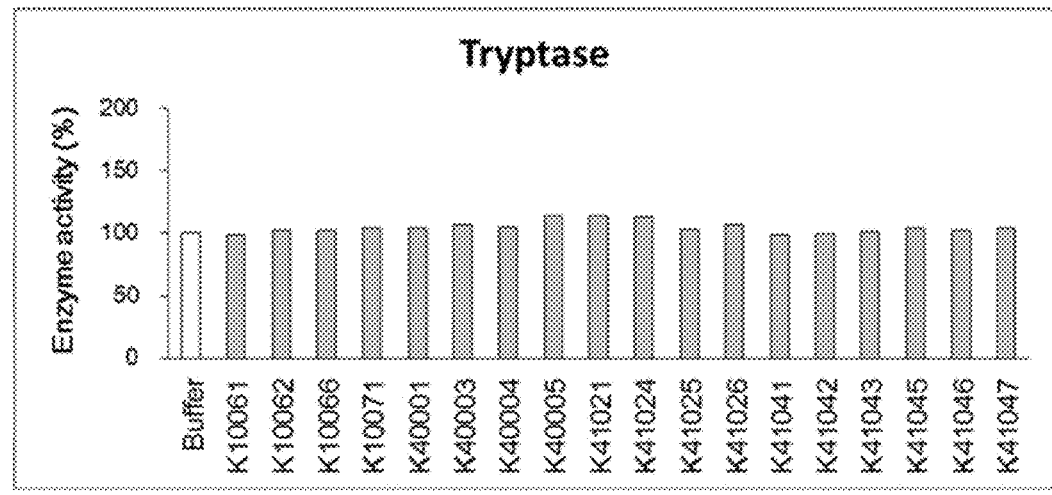
Figures 3, 4A:
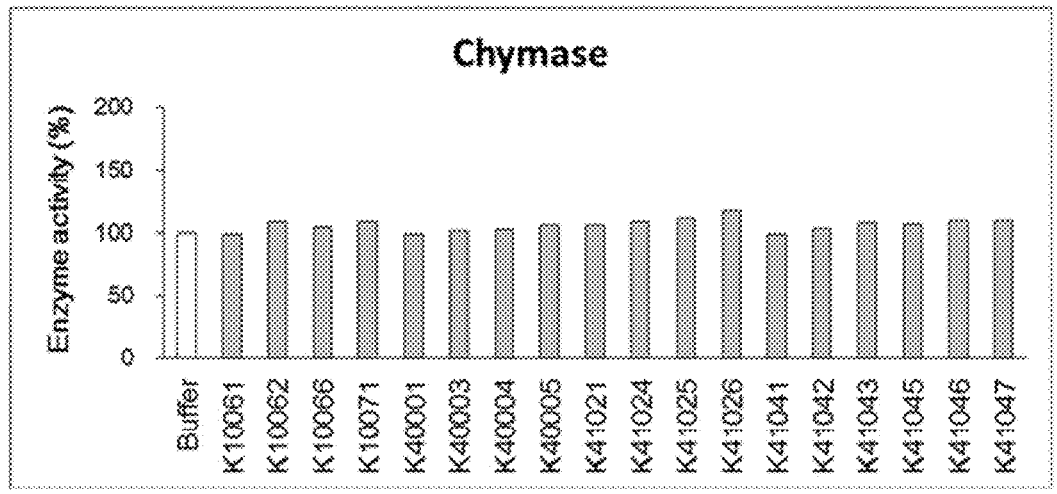
Figures 1, 4B:
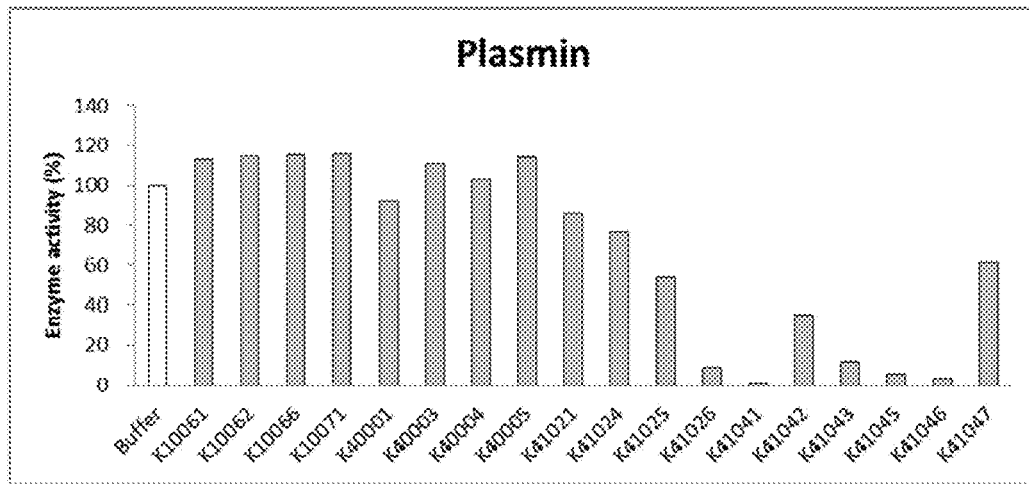
Figures 2, 4B:
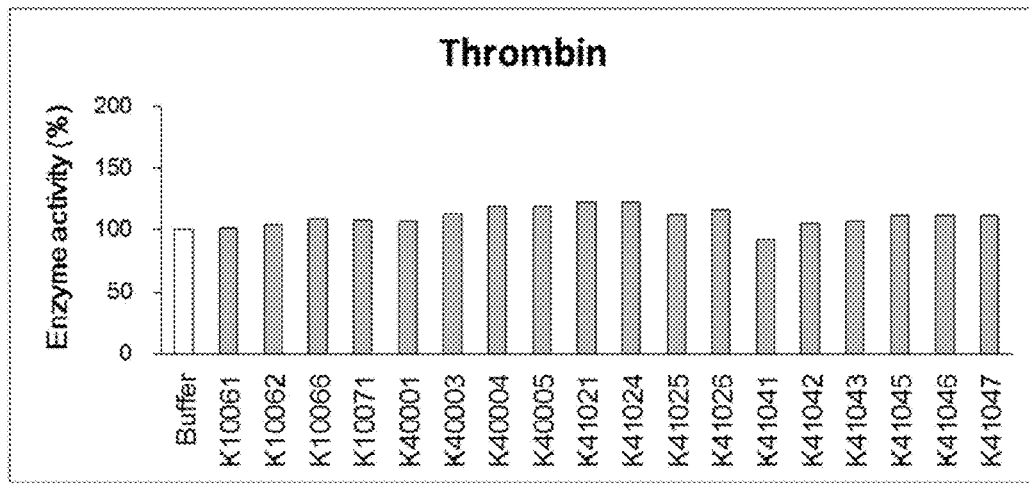
Figures 3, 4B:
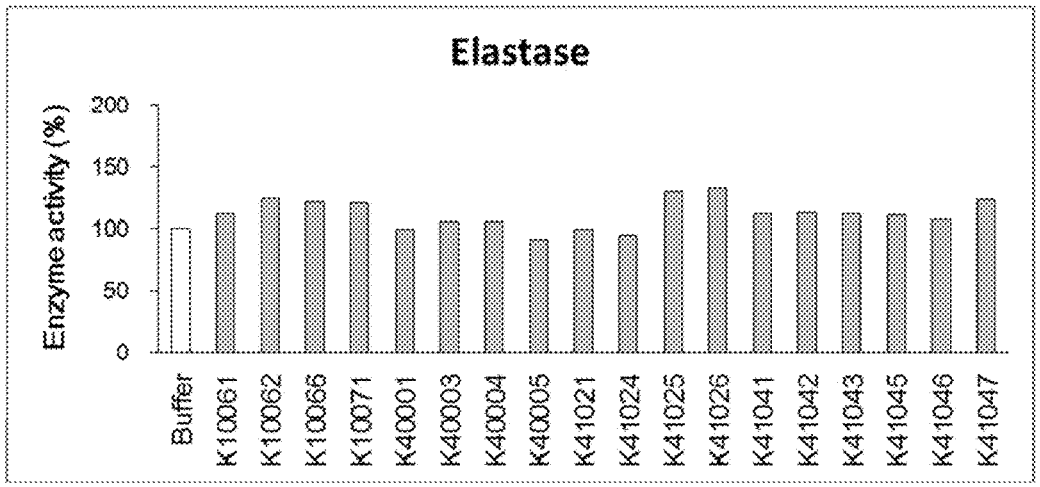
Figures 1, 4C:
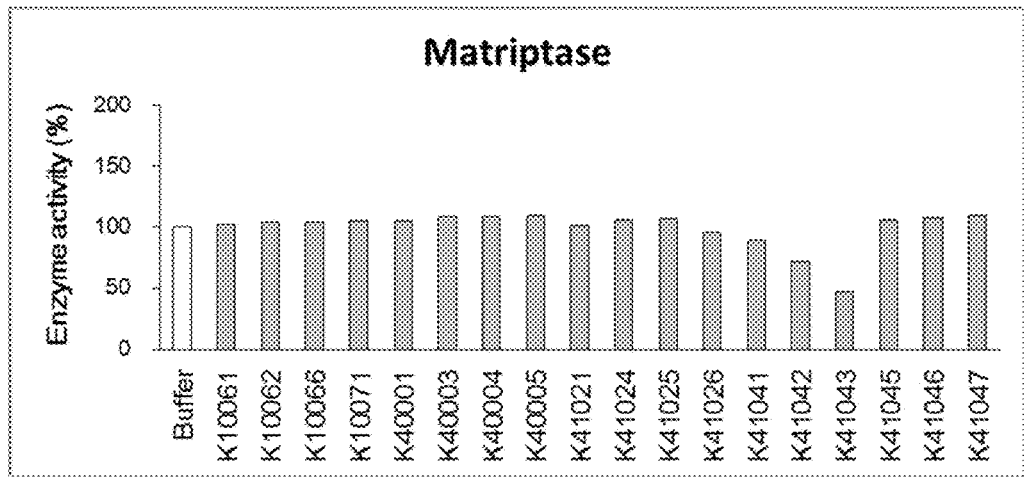
FIG. 1 is a view comparing amino acid sequence similarity of human KLK1, KLK4 and KLK8.
Figures 2, 4C:
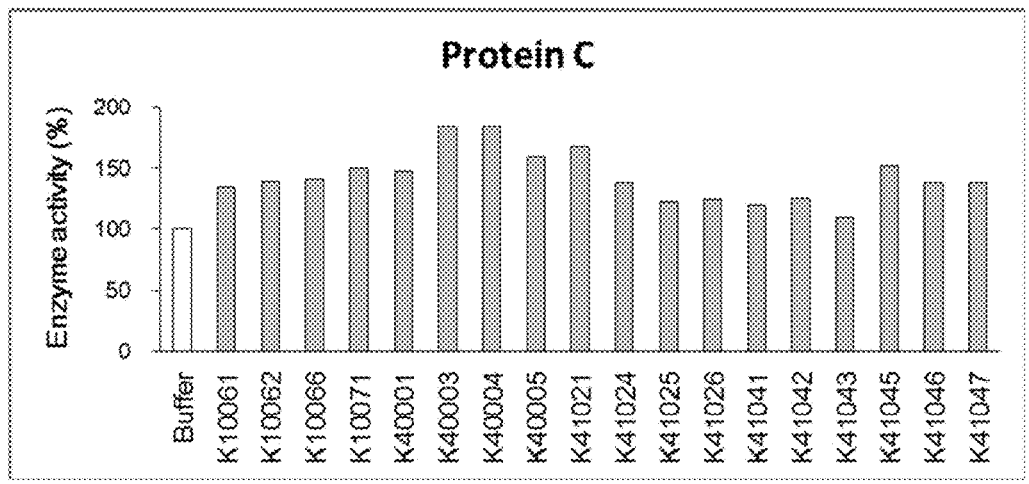
FIG. 2 is a figure showing an evaluation of the KLK1, KLK4 and KLK8 inhibitory activities of each inhibitory peptide, using the degradation rate of the peptide substrate as an index. KLK1 inhibitory activity was performed using KLK1 at the final concentration of 1 nM and PFR-AMC (Bachem Holding AG) at the final concentration of 100 μM. Evaluation of KLK4 inhibitory activity was performed using KLK4 at the final concentration of 10 nM and Boc-VPR-AMC (R&D Systems, Inc.) at the final concentration of 100 μM. Evaluation of KLK8 inhibitory activity was performed using KLK8 at the final concentration of 20 nM and Boc-VPR-AMC at the final concentration of 100 μM.
Figures 3, 4C:
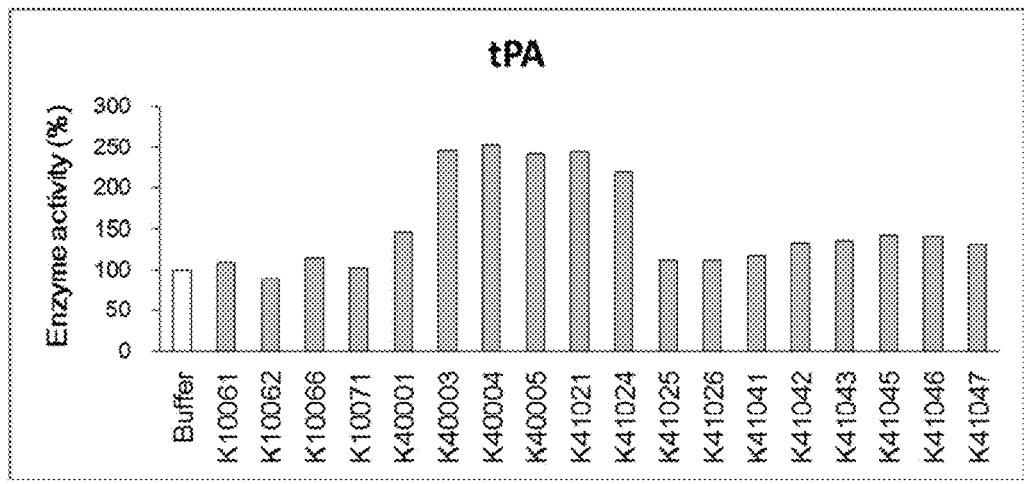
FIG. 3 is a figure showing KLK4 inhibitory activity (Ki) of KLK4 inhibitory peptides, using the degradation rate of the peptide substrate as an index. For evaluation of KLK4 inhibitory activity, KLK4 at the final concentration of 10 nM and Boc-VPR-AMC (R&D Systems, Inc.) at the final concentration of 100 μM were used.
Figures 1, 4D:
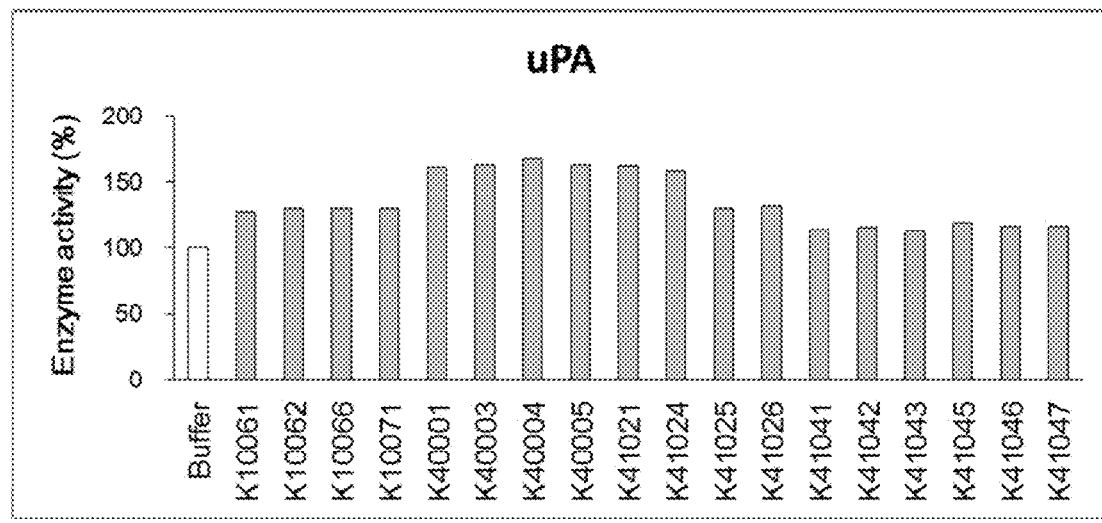
Figures 2, 4D:
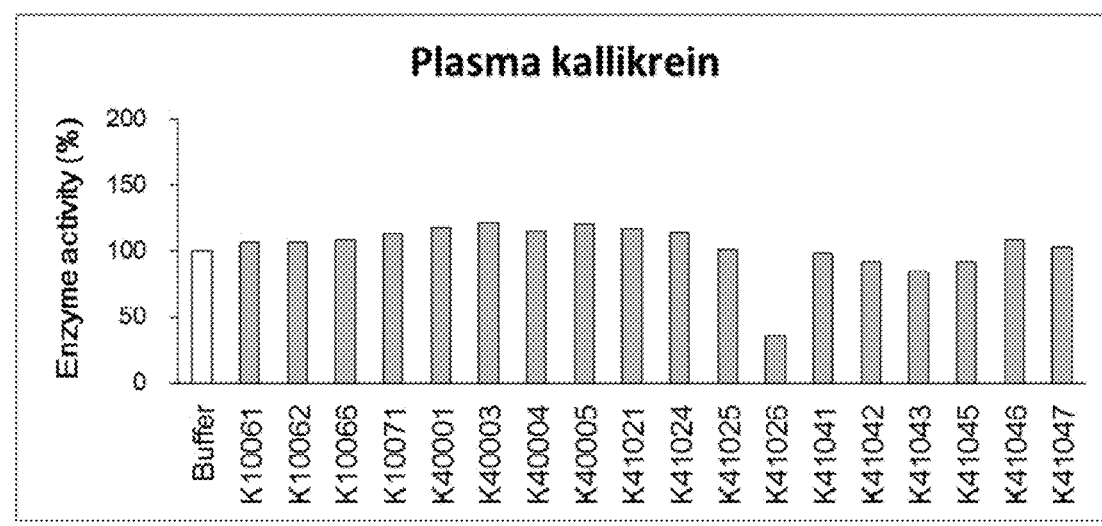

FIGS. 4C-1, 4C-2, and 4C-3 are graphs showing an evaluation of cross-reactivity of each inhibitory peptide to each protease, using the degradation of the peptide substrate as an index. For human matriptase inhibitory activity (FIG. 4C-1), matriptase at the final concentration of 1 nM (R&D Systems, Inc.; E3946-SE), and substrate peptide Boc-QAR-AMC Fluorogenic Peptide Substrate at the final concentration of 100 μM (ES014) were used. For human protein C inhibitory activity (FIG. 4C-2), protein C at the final concentration of 100 nM (Sigma-Aldrich Co.; P2200), and substrate peptide Boc-Leu-Ser-Thr-Arg-MCA (SEQ ID NO. 31) at the final concentration of 100 μM (PEPTIDE INSTITUTE, INC.; 3112-v) were used. For human tPA inhibitory activity (FIG. 4C-3), tPA at the final concentration of 10 nM (Sigma-Aldrich Co.; T0831), and substrate peptide Pyr-Gly-Arg-MCA at the final concentration of 100 μM (PEPTIDE INSTITUTE, INC.; 3145-v) were used. FIGS. 4D-1 and 4D-2 are graphs showing an evaluation of cross-reactivity of each inhibitory peptide to each protease, using the degradation of the peptide substrate as an index. For human uPA inhibitory activity (FIG. 4D-1), uPA at the final concentration of 10 nM (Sigma-Aldrich Co.; T0831), and substrate peptide Pyr-Gly-Arg-MCA at the final concentration of 100 μM (PEPTIDE INSTITUTE, INC.; 3145-v) were used. For human plasma kallikrein inhibitory activity (FIG. 4D-2), plasma kallikrein at the final concentration of 0.125 μg/ml (Sigma-Aldrich Co.; T0831), and substrate peptide Z-Phe-Arg-MCA at the final concentration of 100 μM (PEPTIDE INSTITUTE, INC.; 3095-v) were used.

FIG. 5 is a figure showing the binding affinity of KLK4 inhibitory peptides measured with Biacore T200 (GE healthcare) using biotinylated KLK4.

Figure 6:
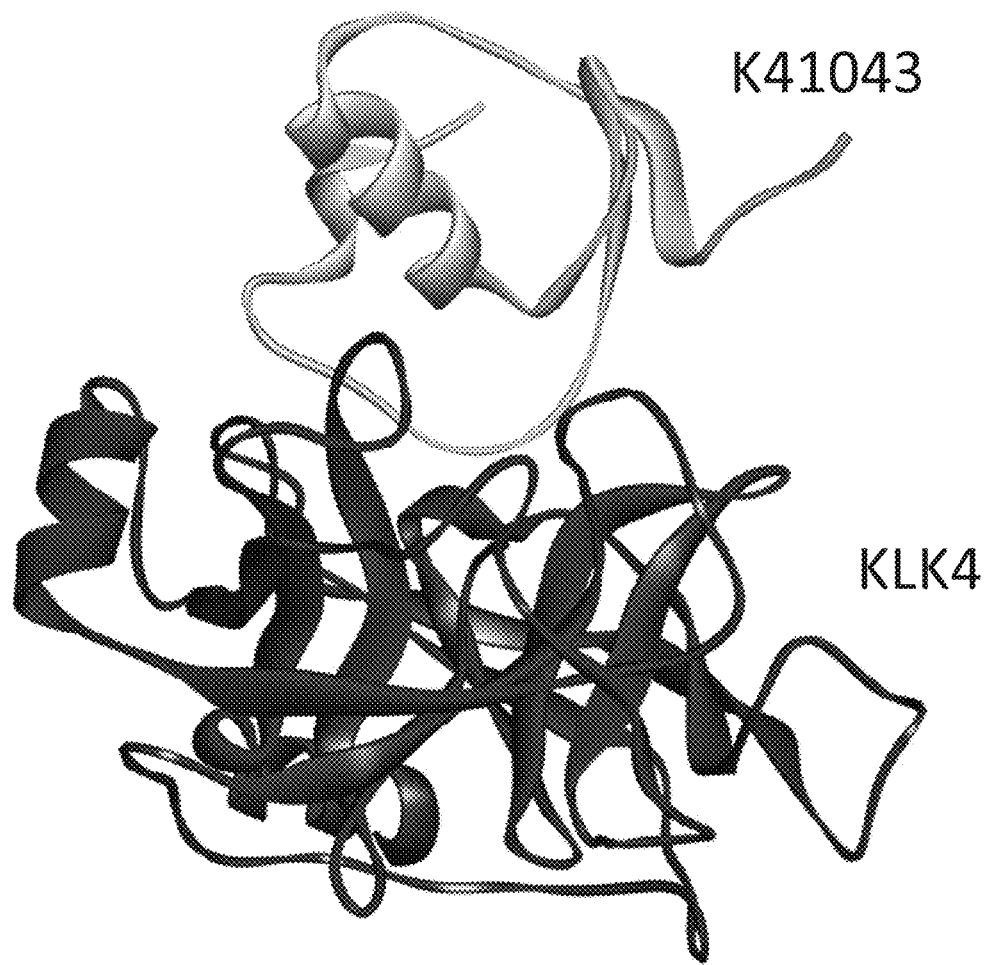

FIG. 6 is a view showing a KLK4/KLK4 inhibitory peptide complex obtained by X-ray crystal structure analysis. The inhibitory peptide was bound to a region containing the KLK4 active center.

FIG. 7 shows the amino acid sequence of human SPINK2 (SEQ ID NO: 1).

FIG. 8 shows the amino acid sequence of human KLK1 (SEQ ID NO: 2).

FIG. 9 shows the amino acid sequence of human KLK4 (SEQ ID NO: 3).

FIG. 10 shows the amino acid sequence of human KLK8 (SEQ ID NO: 4).

FIG. 11 shows the amino acid sequence of KLK1 inhibitory peptide K10061 (SEQ ID NO: 5).

FIG. 12 shows the amino acid sequence of KLK1 inhibitory peptide K10062 (SEQ ID NO: 6).

FIG. 13 shows the amino acid sequence of KLK1 inhibitory peptide K10066 (SEQ ID NO: 7).

FIG. 14 shows the amino acid sequence of KLK1 inhibitory peptide K10071 (SEQ ID NO: 8).

FIG. 15 shows the amino acid sequence of KLK4 inhibitory peptide K40001 (SEQ ID NO: 9).

FIG. 16 shows the amino acid sequence of KLK4 inhibitory peptide K40003 (SEQ ID NO: 10).

FIG. 17 shows the amino acid sequence of KLK4 inhibitory peptide K40004 (SEQ ID NO: 11).

FIG. 18 shows the amino acid sequence of KLK4 inhibitory peptide K40005 (SEQ ID NO: 12).

FIG. 19 shows the amino acid sequence of KLK4/KLK8 inhibitory peptide K41021 (SEQ ID NO: 13).

FIG. 20 shows the amino acid sequence of KLK4/KLK8 inhibitory peptide K41024 (SEQ ID NO: 14).

FIG. 21 shows the amino acid sequence of KLK4/KLK8 inhibitory peptide K41025 (SEQ ID NO: 15).

FIG. 22 shows the amino acid sequence of KLK4/KLK8 inhibitory peptide K41026 (SEQ ID NO: 16).

FIG. 23 shows the amino acid sequence of KLK4/KLK8 inhibitory peptide K41041 (SEQ ID NO: 17).

FIG. 24 shows the amino acid sequence of KLK4/KLK8 inhibitory peptide K41042 (SEQ ID NO: 18).

FIG. 25 shows the amino acid sequence of KLK4/KLK8 inhibitory peptide K41043 (SEQ ID NO: 19).

FIG. 26 shows the amino acid sequence of KLK4/KLK8 inhibitory peptide K41045 (SEQ ID NO: 20).

FIG. 27 shows the amino acid sequence of KLK4/KLK8 inhibitory peptide K41046 (SEQ ID NO: 21).

FIG. 28 shows the amino acid sequence of KLK4/KLK8 inhibitory peptide K41047 (SEQ ID NO: 22).

FIG. 29 shows a general formula (SEQ ID NO: 23) of a KLK1 inhibitory binding peptide, KLK4 inhibitory peptide, or KLK4/KLK8 inhibitory peptide.

FIG. 30 shows the nucleotide sequence of primer 1 (SEQ ID NO: 24).

FIG. 31 shows the nucleotide sequence of primer 2 (SEQ ID NO: 25).

FIG. 32 shows the amino acid sequence of Stag+linker 1 (SEQ ID NO: 26).

FIG. 33 shows the amino acid sequence of a C-terminal 6-mer (SEQ ID NO: 27).

FIG. 34 shows an amino acid sequence of human IgG1 Fc (SEQ ID NO: 28).

DESCRIPTION OF EMBODIMENTS

1. Definitions

In the present invention, the term "gene" means a nucleic acid molecule comprising a nucleotide sequence encoding an amino acid sequence comprised in a protein or a complementary strand thereof, and such a nucleic acid molecule can consist of a single strand, double strands, or triple or more strands, the term "gene" also includes a complex of a DNA strand and an RNA strand, a nucleic acid molecule in which ribonucleotide(s) and deoxyribonucleotide(s) co-exist on a single strand, and a nucleic acid molecule of double strands or triple or more strands comprising such a strand as described herein.

In the present invention, the terms "gene", "polynucleotide" and "nucleic acid molecule" have the same meaning, and the number of their elements, which are ribonucleotides, deoxyribonucleotides, nucleotides, nucleosides and the like, has no limitation. For example, DNA, RNA, mRNA, cDNA, cRNA, probes, oligonucleotides, primers and the like are included within the scope of the terms "gene", "polynucleotide" and "nucleic acid molecule". The term "nucleic acid molecule" is sometimes abbreviated as "nucleic acid".

In the present invention, the terms "polypeptide", "peptide" and "protein" have the same meanings.

In the present invention, a peptide that recognizes or binds to the target molecule X (hereinafter, such recognition or binding action is collectively referred to as "X binding activity") can be referred to as an "X binding peptide". Furthermore, a peptide that recognizes or binds to the target molecule X, and inhibits or suppresses one or two or more activities or functions of the target molecule X (hereinafter, the action of inhibition or suppression is collectively referred to as "X inhibitory activity") can be referred to as an "X inhibitory peptide".

In the present invention, the term "SPINK2" means Serine Protease Inhibitor Kazal-type 2, and is a 7 kDa protein composed of a Kazal-like domain having three disulfide bonds. Preferably, SPINK2 is derived from human. In the present invention, human SPINK2 is simply referred to as "SPINK2", unless otherwise specified.

In the present invention, "KLK1" is a protein that is composed of an N-terminal propeptide and a protease active domain, with three N-type sugar chain additions, and exhibits trypsin-like and chymotrypsin-like protease activities. Preferably, KLK1 is derived from human. In the present invention, human KLK1 is sometimes simply referred to as "KLK1", unless otherwise specified.

In the present invention, "KLK4" is a protein that is composed of an N-terminal propeptide and a trypsin-like domain having protease activity, with an N-type sugar chain addition. Preferably, KLK4 is derived from human. In the present invention, human KLK4 is sometimes simply referred to as "KLK4", unless otherwise specified.

In the present invention, "KLK8" is also called Neuropsin, and is a protein that is composed of an N-terminal propeptide and a trypsin-like domain having protease activity, with an N-type sugar chain addition. Preferably, KLK8 is derived from human. In the present invention, human KLK8 is sometimes simply referred to as "KLK8", unless otherwise specified.

In the present invention, "precursor KLK1" means pro-KLK1, and is composed of a propeptide and a domain having protease activity. "Active KLK1" means active KLK1 and is composed of a domain having protease activity. Preferably, active KLK1 is derived from human.

In the present invention, "precursor KLK4" means pro-KLK4, and is composed of a propeptide and a domain having protease activity. "Active KLK4" means active KLK4 and is composed of a domain having protease activity. Preferably, active KLK4 is derived from human.

In the present invention, "precursor KLK8" means pro-KLK8, and is composed of a propeptide and a domain having protease activity. "Active KLK8" means active KLK8 and is composed of a domain having protease activity. Preferably, active KLK8 is derived from human.

In the present invention, the terms "KLK1 inhibitory peptide", "KLK4 inhibitory peptide" or "KLK4/KLK8 inhibitory peptide" means a peptide that inhibits or suppresses one or two or more activities or functions of KLK1, KLK4, or KLK4 and KLK8, respectively.

When the fragments of the peptide, or, the conjugates of the peptide or the fragments to which another moiety is added or bound maintain the KLK1 inhibitory (binding) activity, KLK4 inhibitory (binding) activity, or KLK4/KLK8 inhibitory (binding) activity, they are included within the scope of the terms "KLK1 inhibitory peptide", "KLK4 inhibitory peptide", and "KLK4/KLK8 inhibitory peptide", respectively. That is, the fragments, adducts, and modified compounds (conjugates) of the peptide maintaining the KLK1 inhibitory (binding) activity, KLK4 inhibitory (binding) activity, or KLK4/KLK8 inhibitory (binding) activity are also included within the terms "KLK1 inhibitory peptide", "KLK4 inhibitory peptide", or "KLK4/KLK8 inhibitory peptide", respectively.

In the present invention, a "site" to which a peptide binds, i.e., a "site" recognized by the peptide, means a sequential or intermittent partial amino acid sequence or partial higher-order structure on a target molecule to which the peptide binds or recognizes. In the present invention, such a site can be referred to as an epitope or binding site on the target molecule.

In the present invention, the term "cell" includes various cells derived from an animal body, subcultured cells, primary cultured cells, cell lines, recombinant cells, yeasts, microorganisms, and the like.

In the present invention, the term "SPINK2 mutant" means a peptide containing an amino acid sequence having, as compared with the amino acid sequence of the wild type SPINK2, one or two or more amino acids substituted with an amino acid different from the wild type, one or two or more amino acids deleted from the wild type, one or two or more amino acids inserted which don't appear in the wild type, and/or amino acid(s) added to the amino-terminal end (N-terminal end) and/or carboxyl-terminal end (C-terminal end) which don't appear in the wild type (hereinafter, these alterations are collectively referred to as "mutation"). When the "SPINK2 mutant" has KLK1 inhibitory activity, KLK4 inhibitory activity, or KLK4 inhibitory activity and KLK8 inhibitory activity (KLK4/KLK8 inhibitory activity), they are encompassed within the KLK1 inhibitory peptide, KLK4 inhibitory peptide, or KLK4/KLK8 inhibitory peptide, respectively.

In addition, in the present invention, the term "insertion" can be included within the scope of the term "addition".

In the present invention, the term "several" in "one to several" refers to 3 to 10.

In the present invention, the phrase "hybridize under stringent conditions" means to hybridize under a condition in which hybridization is performed at 65° C. in a solution containing 5×SSC, and then washings are performed in an aqueous solution containing 2×SSC-0.1% SDS at 65° C. for 20 minutes, in an aqueous solution containing 0.5×SSC-0.1% SDS at 65° C. for 20 minutes, and in an aqueous solution containing 0.2×SSC-0.1% SDS at 65° C. for 20 minutes, respectively, or under equivalent conditions thereto. The SSC represents an aqueous solution of 150 mM NaCl-15 mM sodium citrate, and "n x SSC" means n-fold concentrations of SSC.

The terms "specific" and "specificity" in the present invention have the same meaning as "selective" and "selectivity", respectively, and they are interchangeable. For example, a KLK1-specific inhibitory peptide has the same meaning as a KLK1-selective inhibitory peptide.

2. Peptide 2-1. Amino Acid

The term "amino acid" means an organic compound containing an amino group and a carboxyl group, and it preferably means an α-amino acid included as an element in proteins, more preferably in naturally occurring proteins. In the present invention, more preferred amino acids are Ala, Arg, Asn, Asp, Cys, Gln, Glu, Gly, His, Ile, Leu, Lys, Met, Phe, Pro, Ser, Thr, Trp, Tyr, and Val. Unless otherwise specified, the term "amino acid" means these total 20 amino acids. The total 20 amino acids can be referred to as "natural amino acids". The KLK1 inhibitory peptide, KLK4 inhibitory peptide, or KLK4/KLK8 inhibitory peptide of the present invention preferably contains naturally occurring amino acids.

In the present invention, the term "amino acid residue" is sometimes abbreviated as "amino acid".

In the present invention, an amino acid is an L-amino acid, a D-amino acid, or a mixture thereof (DL-amino acid), but unless otherwise specified, it means an L-amino acid.

The natural amino acids can be divided into, for example, the following groups, based on the common characteristics of the side chains.

(1) Hydrophobic amino acid group: Met, Ala, Val, Leu, Ile
(2) Neutral hydrophilic amino acid group: Cys, Ser, Thr, Asn, Gln
(3) Acidic amino acid group: Asp, Glu
(4) Basic amino acid group: His, Lys, Arg
(5) A group of amino acids that influence the orientation of the backbone: Gly, Pro
(6) Aromatic amino acid group: Trp, Tyr, Phe However, the classification of natural amino acids is not limited to these.

In the present invention, natural amino acids may undergo conservative amino acid substitutions.

The term "conservative amino acid substitution" means a substitution with a functionally equivalent or similar amino acid. A conservative amino acid substitution in a peptide results in a static change in the amino acid sequence of the peptide. For example, one or two or more amino acids having similar polarity act functionally equivalently, thus a conservative amino acid substitution with such amino acids results in a static change in the amino acid sequence of the peptide. In general, a substitution with an amino acid in the same group can be considered conservative in its structure and function. However, as will be apparent to those skilled in the art, the role played by a particular amino acid residue may be determined by the three-dimensional structure of the molecule containing the amino acid. For example, cysteine residues may take the oxidized (disulfide) form, which has less polarity compared to the reduced (thiol) form. The long aliphatic moiety of arginine side chains may constitute structurally and functionally important features. The side chain containing an aromatic ring (tryptophan, tyrosine, phenylalanine) may also contribute to an ion-aromatic interaction or cation-pi interaction. In such a case, even if an amino acids having such a side chain is substituted with an amino acid belonging to the acidic or nonpolar groups, the substitution may be structurally and functionally conservative. The residues such as proline, glycine, and cysteine (disulfide form) have the possibility of directly affecting the backbone conformation, thus they often cannot be substituted without structural distortion.

The conservative amino acid substitutions include specific substitutions based on side chain similarity as shown below (L. Lehninger, Biochemistry, $2^{nd}$ edition, pp. 73-75, Worth Publisher, New York (1975)) and typical substitutions.

(1) Nonpolar amino acid group: alanine (hereinafter referred to as "Ala" or simply "A"), valine (hereinafter referred to as "Val" or simply "V"), leucine (hereinafter referred to as "Leu" or simply "L"), isoleucine (hereinafter referred to as "Ile" or simply "I"), proline (hereinafter referred to as "Pro" or simply "P"), phenylalanine (hereinafter referred to as "Phe" or simply "F"), tryptophan (hereinafter referred to as "Trp" or simply "W"), and methionine (hereinafter referred to as "Met" or simply "M");
(2) Uncharged polar amino acid group: glycine (hereinafter referred to as "Gly" or simply "G"), serine (hereinafter referred to as "Ser" or simply "S"), threonine (hereinafter referred to as "Thr" or simply "T"), cysteine (hereinafter referred to as "Cys" or simply "C"), tyrosine (hereinafter referred to as "Tyr" or simply "Y"), asparagine (hereinafter referred to as "Asn" or simply "N"), and glutamine (hereinafter referred to as "Gln" or simply "Q");
(3) Acidic amino acid group: aspartic acid (hereinafter referred to as "Asp" or simply "D"), and glutamic acid (hereinafter referred to as "Glu" or simply "E");
(4) Basic amino acid group: lysine (hereinafter referred to as "Lys" or simply "K"), arginine (hereinafter referred to as "Arg" or simply "R"), and histidine (hereinafter referred to as "His" or simply "H").

In the present invention, the amino acid may be an amino acid other than a natural amino acid. Examples of such amino acids include, for example, selenocysteine, N-formylmethionine, pyrrolidine, pyroglutamic acid, cystine, hydroxyproline, hydroxylysine, thyroxine, O-phosphoserine, desmosine, β-alanine, sarcosine, ornithine, creatine, γ-aminobutyric acid, opain, theanine, tricolominic acid, kainic acid, domoic acid, and achromeic acid found in naturally occurring peptides and proteins. Further examples of such amino acids include norleucine, N-terminal protected amino acids such as Ac-amino acid, Boc-amino acid, Fmoc-amino acid, Trt-amino acid, and Z-amino acid; C-terminal protected amino acids such as t-butyl ester, benzyl ester, cyclohexyl ester, and fluorenyl ester of amino acids; and other amino acids not found in nature including diamine, ω-amino acid, β-amino acid, γ-amino acid, a Tic derivative of an amino acid, and aminophosphonic acid. However, without limiting to these examples, amino acids other than the 20 "natural amino acids" described above are collectively referred to as "non-natural amino acids", for convenience, in the present invention.

2-2. KLK1 Inhibitory Peptide, KLK4 Inhibitory Peptide, and KLK4/KLK8 Inhibitory Peptide The peptide of the present invention has KLK1 inhibitory activity, KLK4 inhibitory activity, or KLK4/KLK8 inhibitory activity.

KLK1, KLK4 and KLK4/KLK8 which are the targets of the KLK1 inhibitory peptide, the KLK4 inhibitory peptide and the KLK4/KLK8 inhibitory peptide of the present invention, respectively, are preferably derived from vertebrate, more preferably from mammal, even more preferably from primate, and most preferably from human. KLK1, KLK4, and KLK8 can be purified from tissues or cells, or prepared by a method known to those skilled in the art for preparing proteins such as gene recombination, in vitro translation, or peptide synthesis. Furthermore, a signal sequence, immunoglobulin Fc region, tag, label, or the like may be linked to KLK1, KLK4, and KLK8. The KLK1 inhibitory activity, KLK4 inhibitory activity, and KLK4/KLK8 inhibitory activity can be evaluated using protease activities of KLK1, KLK4, and KLK4 and KLK8 as indexes. For example, in the case that KLK1, KLK4, or KLK4 and KLK8, or a functional fragment thereof, a substrate, and a KLK1 inhibitory peptide, KLK4 inhibitory peptide, or KLK4/KLK8 inhibitory peptide of the present invention or a candidate thereof or the like are present together, when the protease activity of KLK1, KLK4, or KLK4 and KLK8 is 70% or less, 50% or less, 30% or less, 20% or less, 10% or less, 5% or less, 1% or less, or 0% compared to the case that the control is present or the inhibitor or a candidate thereof is absent, the KLK1, KLK4, or KLK4/KLK8 is inhibited, and the inhibitory activity is 30% or more, 50% or more, 70% or more, 80% or more, 90% or more, 95% or more, or 99% or more, or 100%, respectively. The KLK1 inhibitory activity, KLK4 inhibitory activity, and KLK4/KLK8 inhibitory activity may vary depending on the reaction conditions, the type and concentration of the substrate, or the like. Examples of the reaction conditions include those described in Examples, but are not limited thereto. The enzyme activity can be evaluated by adding a substrate peptide or substrate protein to KLK1, KLK4, or KLK4 and KLK8 at a certain concentration, reacting it for a certain period of time, and detecting the fluorescence of the substrate peptide or detecting the substrate protein by SDS-PAGE, Western blot method, liquid chromatography, or the like. Examples of the buffer solution include phosphate buffer saline (hereinafter referred to as "PBS") and Tris buffer (50 mM Tris, pH 7 to 8.5, for example, pH 7.5). Furthermore, salts such as NaCl (0 to 200 mM, for example, 200 mM), $CaCl_2$) (0 to 10 mM, for example, 2 mM), $ZnCl_2$, and Brij-35 can be added to the buffer solution. However, the buffer solution is not limited to these.

The substrates of the KLK1, KLK4, or KLK4 and KLK8 proteases are not particularly limited, and examples of them include endogenous substrates, exogenous substrates, and synthetic substrates. Examples of human endogenous substrates of KLK1 include low molecular weight kininogen, callystatin, and collagen. Examples of human endogenous substrates of KLK4 include Pro-KLK3, fibronectin, and collagen. Examples of human endogenous substrates of KLK8 include tPA, fibronectin, and collagen. The gelatin obtained by heat denaturation of collagen can also be used as a substrate. The synthetic substrate is not particularly limited, and examples thereof include PFR-AMC and Boc-VPR-AMC. The KLK1 inhibitory activity ($IC_{50}$ or $K_i$) of the KLK1 inhibitory peptide, KLK4 inhibitory activity of the KLK4 inhibitory peptide, and KLK4/KLK8 inhibitory activity of the KLK4/KLK8 inhibitory peptide of the present invention are 1 µM or less, preferably 100 nM or less, more preferably 10 nM or less, even more preferably 1 nM or less, respectively. In addition, a KLK4/KLK8 inhibitory peptide can be classified based on the relative intensity (ratio) of KLK4 inhibitory activity and KLK8 inhibitory activity (both are either $IC_{50}$ or $K_i$). Preferably, KLK4/KLK8 inhibitory peptides are classified into three groups of (i) KLK4 inhibitory activity being less than 0.5-fold of KLK8 inhibitory activity, (ii) KLK4 inhibitory activity being greater than or equal to 0.5-fold and less than 2-fold of KLK8 inhibitory activity, and (iii) KLK4 inhibitory activity being greater than or equal to 2-fold of KLK8 inhibitory activity. Desired peptides can be selected from these groups depending on the application such as treatment type. For example, when a relatively strong therapeutic effect for a KLK8-related disease is desired compared to that for a KLK4-related disease, the peptide belonging to (iii) above can be suitably selected for the treatment.

Furthermore, it is also preferred that the KLK1 inhibitory peptide, KLK4 inhibitory peptide, or KLK4/KLK8 inhibitory peptide of the present invention does not inhibit or suppress proteases activities other than those of KLK1, KLK4, or KLK4 and KLK8, or the degree of inhibition or suppression of the protease activities other than those of KLK1, KLK4, or KLK4 and KLK8 is relatively weak. In other words, with regard to the protease inhibitory activity of the KLK1 inhibitory peptide, KLK4 inhibitory peptide, or KLK4/KLK8 inhibitory peptide of the present invention, they preferably have high KLK1 specificity, KLK4 specificity, or KLK4/KLK8 specificity, respectively. More preferred peptides of the present invention are those that do not inhibit or suppress the protease activities of KLK2, KLK3, KLK5, KLK6, KLK7, KLK9 to KLK15, chymotrypsin, tryptase, chymase, plasmin, thrombin, elastase, matriptase, protein C, tissue (tPA), urokinase plasminogen activator (uPA), plasma kallikrein or the like, or the degree of inhibition or suppression thereof is relatively weak. Such preferred peptides of the present invention have no side effects caused by the inhibition or suppression of the other protease activities, and can be suitably used as therapeutic or preventive agents for diseases related to KLK1, diseases related to KLK4, or diseases related to KLK4/KLK8 (all described later). Furthermore, the KLK1 inhibitory peptide of the present invention does not inhibit or suppress the protease activities of KLK4 and KLK8, or the degree of inhibition or suppression thereof against the protease activities of KLK4 and KLK8 is relatively weak; the KLK4 inhibitory peptide of the present invention does not inhibit or suppress the protease activities of KLK1 and KLK8, or the degree of inhibition or suppression thereof against the protease activities of KLK1 and KLK8 is relatively weak; or the KLK4/KLK8 inhibitory peptide of the present invention does not inhibit or suppress the protease activity of KLK1, or the degree of inhibition or suppression thereof against the protease activity of KLK1 is relatively weak.

The inhibitors having low specificity for KLK1, KLK4, or KLK4 and KLK8, and inhibiting protease activities of other KLKs in addition to KLK1, KLK4, or KLK4 and KLK8, that is, non-selective inhibitors cause serious side effects when administered to humans (Coussens, L M et al., Science, vol. 295 (No. 5564), pp. 2387-92 (2002): Bisseset, D et al., J. Clin. Oncol., vol. 23 (No. 4), pp. 842-9 (2005)). In contrast, inhibitors having high specificity for KLK1, KLK4, or KLK4/KLK8, i.e., a KLK1-specific inhibitory peptide, a KLK4-specific inhibitory peptide, or a KLK4/KLK8-specific inhibitory peptide can avoid such side effects as described above. Thus, the inhibitors having high specificity for KLK1, KLK4, or KLK4/KLK8 can be suitably used for the treatment or prevention of diseases related to KLK1, diseases related to KLK4, or diseases related to KLK4/KLK8, respectively.

The KLK1 inhibitory peptide, KLK4 inhibitory peptide, or KLK4/KLK8 inhibitory peptide of the present invention may competitively bind the protease substrate of KLK1, KLK4, or KLK4 and/or KLK8.

As noted above, KLK1, KLK4, and KLK8, which are the targets of the peptides of the present invention, are derived from vertebrate, preferably mammal, more preferably primate, and even more preferably human, but they may be derived from a non-human animal, for example, rodents such as rat and mouse, and primates such as cynomolgus monkey, common marmoset, and rhesus monkey. Such a peptide having inhibitory activity against KLK1, KLK4, or KLK4 and KLK8 derived from a non-human animal can be used to diagnose, test, treat or prevent diseases related to KLK1, KLK4, or KLK4 and KLK8 in such a non-human animal. Furthermore, when such a peptide also inhibits human KLK1, KLK4, or KLK4 and KLK8, pharmacological and pharmacokinetic tests in an animal pathological model using such a non-human animal, and safety tests and toxicity tests using a non-human animal as a healthy animal can be performed using the peptide in non-clinical research and development of the peptide as a therapeutic or prophylactic agent for diseases related to human KLK1, KLK4, or KLK4 and KLK8.

The KLK1 inhibitory peptide, KLK4 inhibitory peptide, and KLK4/KLK8 inhibitory peptide of the present invention have a smaller molecular weight than other biomacromolecules such as antibodies used in this field as pharmaceutical or diagnostic agents, and the production of the peptide (described later) is relatively easy. The peptide of the present invention is also excellent in terms of physicochemical properties such as storage stability and heat stability. Furthermore, the peptide has advantages in that it has wide alternatives for administration route, administration method, formulation, or the like when used in a pharmaceutical composition (described later). It is also possible to adjust the half-life of the peptide in blood so as to be longer by increasing the molecular weight of the peptides of the present invention using a known method such as addition of a biomacromolecule or a polymer when using the peptide as a pharmaceutical composition. The molecular weight of such a KLK1 inhibitory peptide, KLK4 inhibitory peptide, and KLK4/KLK8 inhibitory peptide of the present invention is less than 10,000, preferably less than 8,000, more preferably about 7,000 to 7,200. Out of a variable loop region consisting of Cys 15 to Cys 31 and a moiety consisting of Cys 15 to Cys 63 of SEQ ID NO: 23 (FIG. 29) (hereinafter referred to as a "moiety containing 6 Cys"), ones having KLK1 inhibitory activity, KLK4 inhibitory activity, or KLK4/KLK8 inhibitory activity are also included within the KLK1 inhibitory peptide, KLK4 inhibitory peptide, or KLK4/KLK8 inhibitory peptide of the present invention. The molecular weight of the variable loop region is less than 2,500, preferably about 1,800 to 2,000, and the molecular weight of the moiety containing 6 Cys is less than 6,000, preferably about 5,300 to 5,500.

The KLK1 inhibitory peptide, KLK4 inhibitory peptide, or KLK4/KLK8 inhibitory peptide of the present invention is a SPINK2 mutant in which the framework (scaffold) of SPINK2 is maintained at least partially (hereinafter, abbreviated as "SPINK2 mutant"). Preferably, the KLK1 inhibitory peptide, KLK4 inhibitory peptide, or KLK4/KLK8 inhibitory peptide of the present invention recognizes or binds to a partial peptide, a partial higher-order structures or the like of KLK1, KLK4, or KLK4/KLK8 (hereinafter, such recognition or binding action is collectively referred to as "target-binding activity").

The binding of the SPINK2 mutant of the present invention to KLK1, KLK4, or KLK8 can be measured or determined using a method known to those skilled in the art, such as ELISA method, Surface Plasmon Resonance (hereinafter referred to as "SPR") analysis method, Biolayer Interferometry (hereinafter referred to as "BLI") method, Isothermal Titration Calorimetry (hereinafter referred to as "ITC"), flow cytometry, immunoprecipitation method, and the like.

As regards the ELISA method, a method of detecting a KLK1 inhibitory peptide, KLK4 inhibitory peptide, or KLK4/KLK8 inhibitory peptide that recognizes and binds to KLK1, KLK4, or KLK4/KLK8 immobilized on a plate can be illustrated. For immobilizing KLK1, KLK4, or KLK4/KLK8 on a plate, in addition to biotin-streptavidin, an antibody for immobilization that recognizes KLK1, KLK4, or KLK4/KLK8, or a tag fused to KLK1, KLK4, or KLK4/KLK8 or the like can be used. For detection of a KLK1 inhibitory peptide, KLK4 inhibitory peptide, or KLK4/KLK8 inhibitory peptide, in addition to labeled streptavidin, a labeled detection antibody that recognizes a KLK1 inhibitory peptide, KLK4 inhibitory peptide, or KLK4/KLK8 inhibitory peptide or a tag fused to a KLK1 inhibitory peptide, KLK4 inhibitory peptide, or KLK4/KLK8 inhibitory peptide or the like can be used. For labeling, in addition to biotin, any other means applicable for biochemical analysis such as HRP, alkaline phosphatase, or FITC can be used. For detection using a labeled enzyme, chromogenic substrates such as TMB (3,3',5,5'-tetramethylbenzidine), BCIP (5-bromo-4-chloro-3-indolyl phosphate), p-NPP (p-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific); fluorogenic substrates such as QuantaBlu® Fluorogenic Peroxidase Substrate (Thermo Fisher Scientific); and chemiluminescent substrates can be used. For measuring detected signals, an absorbance plate reader, a fluorescence plate reader, a luminescence emission plate reader, an RI liquid scintillation counter, or the like can be used.

Examples of the devices used for SPR analysis include BIAcore® (GE Healthcare), ProteOn® (Bio-Rad Laboratories, Inc.), SPR-Navi® (BioNavis Oy), Spreeta® (Texas Instruments Incorporate), SPRi-PlexII® (HORIBA Scientific), and Autolab SPR® (Metrohm AG). Examples of the devices used for the BLI method include Octet® (Pall Corporation).

As regards the immunoprecipitation method, a method for detecting KLK1, KLK4, or KLK4/KLK8 which is recognized and bound by the KLK1 inhibitory peptide, KLK4 inhibitory peptide, or KLK4/KLK8 inhibitory peptide immobilized on beads can be illustrated. As the beads, magnetic beads or agarose beads can be used. For immobilizing the KLK1 inhibitory peptide, KLK4 inhibitory peptide, or KLK4/KLK8 inhibitory peptide, biotin-streptavidin as well as an antibody that recognizes the peptide or a tag fused to the peptide, protein A, protein G, or the like can be used. The beads are separated by magnets, centrifugation, or the like and KLK1, KLK4, or KLK4 and KLK8 precipitated with the beads is detected by SDS-PAGE or Western blot method. For detection of KLK1, KLK4, or KLK4 and KLK8, labeled streptavidin as well as a labeled detection antibody that recognizes KLK1, KLK4, or KLK8 or a tag fused to KLK1, KLK4, or KLK8 can be used. For labeling, biotin as well as any other means applicable for biochemical analysis, such as HRP, alkaline phosphatase or FITC can be used. For detection using a labeled enzyme, the same substrate as in the ELISA method can be used. For measuring detection signals, ChemiDoc® (Bio-Rad Laboratories, Inc.), Luminograph (ATTO Corporation) and the like can be used.

In the present invention, the term "specific recognition" or "specific binding" means a binding that is not non-specific adsorption. As a criterion to determine whether or not the binding is specific, the binding activity $EC_{50}$ in the ELISA method can be illustrated. As an example of another criterion for determination, the dissociation constant can be illustrated (hereinafter referred to as "$K_D$"). The $K_D$ value of the KLK1 inhibitory peptide of the present invention for KLK1, the $K_D$ value of the KLK4 inhibitory peptide of the present invention for KLK4, or the $K_D$ value of the KLK4/KLK8 inhibitory peptide of the present invention for KLK4 and KLK8 is $1\times10^{-5}$ M or less, $5\times10^{-6}$ M or less, $2\times10^{-6}$ M or less, or $1\times10^{-6}$ M or less, more preferably $5\times10^{-7}$ M or less, $2\times10^{-7}$ M or less, or $1\times10^{-7}$ M or less, even more preferably $5\times10^{-8}$ M or less, $2\times10^{-8}$ M or less, or $1\times10^{-8}$ M or less, and still even more preferably $5\times10^{-9}$ M or less, $2\times10^{-9}$ M or less, or $1\times10^{-9}$ M or less. As further examples of the other criteria for determination, an analysis result by an immunoprecipitation method can be illustrated. In the immunoprecipitation method, a signal of KLK1, KLK4, or KLK4 and KLK8 is detected, when immobilizing a preferred KLK1 inhibitory peptide, KLK4 inhibitory peptide, or KLK4/KLK8 inhibitory peptide in the present invention on beads; adding KLK1, KLK4, or KLK4 and KLK8, respectively; then separating the beads; and detecting KLK1, KLK4, or KLK4 and KLK8 precipitated together with the beads.

The SPINK2 mutant as the KLK1 inhibitory peptide, KLK4 inhibitory peptide, or KLK4/KLK8 inhibitory peptide of the present invention may have protease inhibitory activity, target binding activity, and other properties, functions, features or the like as described above, while the full-length amino acid sequence of the KLK1 inhibitory peptide, KLK4 inhibitory peptide, or KLK4/KLK8 inhibitory peptide has high sequence identity to the amino acid sequence of human wild type SPINK2. The amino acid sequence of the SPINK2 mutant of the present invention has a sequence identity of 60% or more, 70% or more, 75% or more, 80% or more, 85% or more, 90% or more, 95% or more, 98% or more, or 99% or more to the amino acid sequence of human SPINK2 (SEQ ID NO: 1, FIG. 7).

The term "identity" means a property that indicates the degree of similarity or relationship between two sequences. The amino acid sequence identity (%) is calculated by dividing the number of identical amino acids or amino acid residues by the total number of amino acids or amino acid residues, and by multiplying the obtained numerical value by 100.

The term "gap" means a gap in the alignment among two or more sequences resulting from a deletion and/or addition in at least one of the two or more sequences.

The identity between two amino acid sequences having completely identical amino acid sequences is 100%, while, if there is a substitution, deletion or addition of one or two or more amino acids or amino acid residues in one amino acid sequence compared to the other sequence, the identity of both is less than 100%. Examples of algorithms and programs for determining the identity between the two sequences while considering gaps include those known to one of ordinary skill in the art, such as BLAST (Altschul, et al. Nucleic Acids Res., Vol. 25, pp. 3389-3402, 1997), BLAST2 (Altschul, et al. J. Mol. Biol., Vol. 215, pp. 403-410, 1990), and Smith-Waterman (Smith, et al. J. Mol. Biol., Vol. 147, pp. 195-197, 1981) and the like, in which standard parameters are used.

In the present invention, the term "mutated" means that a substitution, a deletion or an insertion of one or two or more nucleotides or nucleotide residues or amino acids or amino acid residues has been made in a nucleotide sequence or amino acid sequence compared to a naturally occurring nucleic acid molecule or peptide. The amino acid sequence of the SPINK2 mutant of the present invention has one or two or more amino acids or amino acid residues mutated, compared to the amino acid sequence of human SPINK2.

In one embodiment of the present invention, the amino acid sequence of the SPINK2 mutant has, in the amino acid sequence of human SPINK2 (SEQ ID NO: 1, FIG. 7):

a substitution of one, two, three, four, five, six, or seven amino acids within the amino acid sequence from Ser16 to Gly22 with another amino acid or amino acid residue; and a substitution of one, two, three, four, or five amino acids within the amino acid sequence from Pro24 to Asn28 with another amino acid or amino acid residue.

It is preferred that the Cys15, Cys23, Cys31, Cys42, Cys45, and Cys63 are Cys as in the wild type, in order to maintain the naturally occurring disulfide bonds. However, one, two, three, four, five or six of them may be substituted with another amino acid so as to eliminate the naturally occurring disulfide bonds or to generate a non-naturally occurring disulfide bond. In some preferred KLK1 inhibitory peptides, KLK4 inhibitory peptides, or KLK4/KLK8 inhibitory peptides of the SPINK2 mutants of the present invention, Cys are maintained at the same 6 positions as those in the naturally occurring peptide, thus the disulfide bonds are maintained. In some more preferred embodiments of such peptides, Cys15-Cys45, Cys23-Cys42, and Cys31-Cys63 form disulfide bonds respectively.

When such an amino acid sequence of the SPINK2 mutant is comprised in the KLK1 inhibitory peptide, KLK4 inhibitory peptide, or KLK4/KLK8 inhibitory peptide, it is preferred that the conformation including a loop structure consisting of the amino acids from Ser 16 to Val 30, a β sheet composed of β strand (1) consisting of Cys 31 and Gly 32 and β strand (2) consisting of the amino acids from Ile 57 to Arg 59, and an α helix consisting of the amino acids from Glu 41 to Gly 51, each of which are comprised in the wild type SPINK2, or, a loop structure, a β sheet and an α helix similar thereto or at least partially corresponding thereto (or to the positions thereof) is maintained to the extent that the KLK1 inhibitory activity, KLK4 inhibitory activity, or KLK4/KLK8 inhibitory activity can be exerted.

Among the SPINK2 mutants of the present invention, the amino acid sequences of some KLK1 inhibitory peptides, KLK4 inhibitory peptides, or KLK4/KLK8 inhibitory peptides are described below. As described above, the term "amino acid residue" is sometimes simply expressed as "amino acid", in the present invention.

In the amino acid sequence (general formula) represented by SEQ ID NO: 23 (FIG. 29), each of $X_1$ to $X_{13}$ is not particularly limited as long as they are any amino acids to the extent that KLK1, KLK4, or KLK4 and KLK8 are inhibited. Hereinafter, preferred amino acids of $X_1$ to $X_{13}$ are described, but they may include natural amino acids, i.e., the same amino acids as in the amino acid sequence of the wild type human SPINK2.

In the amino acid sequence represented by SEQ ID NO: 23 (FIG. 29) contained in the KLK1 inhibitory peptide, preferably:

$1^{st}$ Xaa ($X_1$) is Asp or Gly;
$16^{th}$ Xaa ($X_2$) is Ala, Asp or Ser;
$17^{th}$ Xaa ($X_3$) is Ile, Gln, Arg or Val;
$18^{th}$ Xaa ($X_4$) is Ala, Asn or Tyr;
$19^{th}$ Xaa ($X_5$) is Leu, Lys, Asn or Gln;
$20^{th}$ Xaa ($X_6$) is Ile, Arg, Tyr or Val;
$21^{st}$ Xaa ($X_7$) is Asp, Arg or Val;
$22^{nd}$ Xaa ($X_8$) is Asp, Ile or Arg;
$24^{th}$ Xaa ($X_9$) is Phe, His or Trp;
$25^{th}$ Xaa ($X_{10}$) is Tyr or Trp;
$26^{th}$ Xaa ($X_{11}$) is Ala, Thr or Tyr;
$27^{th}$ Xaa ($X_{12}$) is Ser or Tyr; and
$28^{th}$ Xaa ($X_{13}$) is Glu, Lys or Gln.

In the amino acid sequence represented by SEQ ID NO: 23 (FIG. 29) contained in the KLK4 inhibitory peptide, preferably:

$1^{st}$ Xaa ($X_1$) is Asp or Gly;
$16^{th}$ Xaa ($X_2$) is Glu, Arg or Ser;
$17^{th}$ Xaa ($X_3$) is His, Lys, Leu or Gln;
$18^{th}$ Xaa ($X_4$) is Ala, Gln or Tyr;
$19^{th}$ Xaa ($X_5$) is Ala, Glu, Gln or Val;
$20^{th}$ Xaa ($X_6$) is Glu, Leu, Met or Tyr;
$21^{st}$ Xaa ($X_7$) is Asp or Gly;
$22^{nd}$ Xaa ($X_8$) is Ala or Val;
$24^{th}$ Xaa ($X_9$) is Gln;
$25^{th}$ Xaa ($X_{10}$) is Lys or Arg;
$26^{th}$ Xaa ($X_{11}$) is Ile;
$27^{th}$ Xaa ($X_{12}$) is Phe or Tyr; and
$28^{th}$ Xaa ($X_{13}$) is Lys, Leu or Gln.

In the amino acid sequence represented by SEQ ID NO: 23 (FIG. 29) contained in the KLK4/KLK8 inhibitory peptide, preferably:

$1^{st}$ Xaa ($X_1$) is Asp or Gly;
$16^{th}$ Xaa ($X_2$) is Gly, Met, Gln, Arg, Ser or Thr;
$17^{th}$ Xaa ($X_3$) is Lys or Arg, $X_4$ is Phe, His, Gln or Tyr;
$18^{th}$ Xaa ($X_4$) is Phe, His, Gln or Tyr;
$19^{th}$ Xaa ($X_5$) is His, Lys, Arg, Ser, Thr, Val or Tyr;
$20^{th}$ Xaa (X6) is Ile, Lys, Leu, Met, Gln, Arg, Ser, Val or Trp;

21$^{st}$ Xaa (X$_7$) is Asp, Glu, Gly, His, Asn, Arg, Val or Trp;
22$^{nd}$ Xaa (X$_8$) is Gly or Trp;
24$^{th}$ Xaa (X$_9$) is Ala, Phe, Asn, Ser or Thr;
25$^{th}$ Xaa (X$_{10}$) is Lys or Arg;
26$^{th}$ Xaa (X$_{11}$) is Ile, Met, Gln, Ser or Val;
27$^{th}$ Xaa (X$_{12}$) is Phe, Leu or Tyr; and
28$^{th}$ Xaa (X$_{13}$) is Ala, Asp, Glu or Asn.

In the wild type, the amino acids of the 1st, 16$^{th}$ to 22$^{nd}$ and 24$^{th}$ to 28$^{th}$ Xaa (X$_1$ to X$_{13}$) are Asp, Ser, Gln, Tyr, Arg, Leu, Pro, Gly, Pro, Arg, His, Phe and Asn, respectively.

In the present invention, one to several or more amino acids may be further added to the N-terminal side of the first amino acid. Examples of such amino acids to be added include an amino acid sequence consisting of Stag+linker (SEQ ID NO: 26, FIG. 32).

Furthermore, one to several amino acids may be added to Cys63 located at the C-terminus. For example, an amino acid sequence having Gly65 as the C-terminal amino acid by adding Gly-Glycan can be illustrated. Examples of such amino acids to be added include a C-terminal 6-mer (SEQ ID NO: 27, FIG. 33), Gly-Gly-Gly, and Gly-Gly.

In the present invention, the peptide with a substitution, addition, and/or deletion of one or two or more amino acids in a SPINK2 mutant peptide or a N-terminal and/or C-terminal adduct of a SPINK2 mutant peptide (hereinafter referred to as "parent peptide") are sometimes referred to as the "derivative of the parent peptide" or "parent peptide derivative". Such a "derivative" is also included within the scope of the "peptide" of the present invention.

In the amino acid sequence of the SPINK2 mutant included within the scope of the KLK1 inhibitory peptide, KLK4 inhibitory peptide, or KLK4/KLK8 inhibitory peptide of the present invention, the regions other than X$_1$ to X$_{13}$, i.e., positions between Pro 2 and Cys 15, Cys 23 and between Pro 29 to Cys 63 in the amino acid sequence of wild type human SPINK2 (SEQ ID NO: 1, FIG. 7) can include a naturally occurring (wild type) or mutated amino acid or amino acid sequence. For example, a SPINK2 mutant may be mutated at any one or two or more positions as long as the mutation does not completely hinder or interfere with the KLK1 inhibitory activity, KLK4 inhibitory activity, or KLK4/KLK8 inhibitory activity or folding. Such a mutation may be made by using a standard method known to those skilled in the art. Typical mutations in amino acid sequences can include substitutions, deletions, or additions of one or two or more amino acids. Examples of substitutions include conservative substitutions. By way of a conservative substitution, a certain amino acid residue can be substituted by another amino acid residue that has similar chemical characteristics in terms of not only bulkiness but also polarity. Examples of conservative substitutions are described elsewhere in this specification. However, in the regions other than X$_1$ to X$_{13}$, non-conservative substitutions of one or two or more amino acids may be allowed as long as the substitution does not completely hinder or interfere with the KLK1 inhibitory activity, KLK4 inhibitory activity, or KLK4/KLK8 inhibitory activity or folding.

In the amino acid sequence of the SPINK2 mutant as the KLK1 inhibitory peptide, KLK4 inhibitory peptide, or KLK4/KLK8 inhibitory peptide of the present invention, X$_1$ to X$_{13}$ are preferably respective amino acids of X$_1$ to X$_{13}$ in any one of SEQ ID NOs: 5 to 8 (FIGS. 11 to 14), SEQ ID NOs: 9 to 12 (FIGS. 15 to 18), or SEQ ID NOs: 13 to 22 (FIGS. 19 to 28), and the regions other than X$_1$ to X$_{13}$ can have an amino acid or amino acid sequence which does not completely hinder or interfere with the KLK1 inhibitory activity, KLK4 inhibitory activity, or KLK4/KLK8 inhibitory activity or folding.

Examples of the amino acid sequence of the SPINK2 mutant as the KLK1 inhibitory peptide, KLK4 inhibitory peptide, or KLK4/KLK8 inhibitory peptide of the present invention include the amino acid sequences described in any one of the following (a1) to (a3), (b1) to (b3), or (c1) to (c3), respectively:

(a1) an amino acid sequence represented by any one of SEQ ID NOs: 5 to 8 (FIGS. 11 to 14);
(a2) an amino acid sequence encoded by a nucleotide sequence that hybridizes with a nucleotide sequence complementary to a nucleotide sequence encoding the amino acid sequence described in (a1) under stringent conditions, and encoding an amino acid sequence contained in a peptide having KLK1 inhibitory activity;
(a3) an amino acid sequence having 1 to 20, 1 to 15, 1 to 10, 1 to 8, 1 to 6, 1 to 5, 1 to 4, 1 to 3, 1 to 2, or 1 amino acid substitution, deletion, addition and/or insertion in the amino acid sequence described in (a1), and contained in a peptide having KLK1 inhibitory activity; and
(a4) an amino acid sequence that is 60%, 70%, 80%, 85%, 90%, 92%, 94%, 96%, 97%, 98%, or 99% or more identical to the amino acid sequence described in (a1), and contained in a peptide having KLK1 inhibitory activity,
(b1) an amino acid sequence represented by any one of SEQ ID NOs: 9 to 12 (FIGS. 15 to 18);
(b2) an amino acid sequence encoded by a nucleotide sequence that hybridizes with a nucleotide sequence complementary to a nucleotide sequence encoding the amino acid sequence described in (b1) under stringent conditions, and encoding an amino acid sequence contained in a peptide having KLK4 inhibitory activity;
(b3) an amino acid sequence having 1 to 20, 1 to 15, 1 to 10, 1 to 8, 1 to 6, 1 to 5, 1 to 4, 1 to 3, 1 to 2, or 1 amino acid substitution, deletion, addition and/or insertion in the amino acid sequence described in (b1), and contained in a peptide having KLK4 inhibitory activity; and
(b4) an amino acid sequence that is 60%, 70%, 80%, 85%, 90%, 92%, 94%, 96%, 97%, 98%, or 99% or more identical to the amino acid sequence described in (b1), and contained in a peptide having KLK4 inhibitory activity, or
(c1) an amino acid sequence represented by any one of SEQ ID NOs: 13 to 22 (FIGS. 19 to 28);
(c2) an amino acid sequence encoded by a nucleotide sequence that hybridizes with a nucleotide sequence complementary to a nucleotide sequence encoding the amino acid sequence described in (c1) under stringent conditions, and encoding an amino acid sequence contained in a peptide having KLK4/KLK8 inhibitory activity;
(c3) an amino acid sequence having 1 to 20, 1 to 15, 1 to 10, 1 to 8, 1 to 6, 1 to 5, 1 to 4, 1 to 3, 1 to 2, or 1 amino acid substitution, deletion, addition and/or insertion in the amino acid sequence described in (c1), and contained in a peptide having KLK4/KLK8 inhibitory activity; and
(C4) an amino acid sequence that is 60%, 70%, 80%, 85%, 90%, 92%, 94%, 96%, 97%, 98%, or 99% or more identical to the amino acid sequence described in (c1), and contained in a peptide having KLK4/KLK8 inhibitory activity.

Mutations can be introduced into the KLK1 inhibitory peptide, the KLK4 inhibitory peptide, or the KLK4/KLK8 inhibitory peptide of the present invention, in order to improve the folding stability, heat stability, storage stability, blood half-life, water solubility, biological activity, pharmacological activity, secondary effects, or the like. For example, a new reactive group such as Cys can be introduced by mutation for conjugation to other substances such as polyethylene glycol (PEG), hydroxyethyl starch (HES), biotin, a peptide or a protein.

In the present invention, the KLK1 inhibitory peptide, KLK4 inhibitory peptide, or KLK4/KLK8 inhibitory peptide may be linked or added to other moieties, and such conjugates are collectively referred to as "conjugates of KLK1 inhibitory peptide", "conjugates of KLK4 inhibitory peptide" or "conjugates of KLK4/KLK8 inhibitory peptide", respectively. In the present invention, the term "conjugate" means a molecule obtained by binding another part to the peptide of the present invention or a fragment thereof. The "conjugate" or "conjugation" includes a form in which a certain moiety is linked or bound to the peptide of the present invention: via a chemical substance such as a cross-linking agent; or via an agent suitable for linking the certain moiety to the side chain of an amino acid; or by synthetic chemical or genetic engineering techniques to the N-terminal and/or C-terminal end of the peptide of the present invention. Examples of such a "moiety" for improving half-life in blood include polyalkylene glycol molecules such as polyethylene glycol (PEG); fatty acid molecules such as hydroxyethyl starch, palmitic acid, or the like; Fc regions of immunoglobulins (e.g., human immunoglobulin G1: an amino acid sequence thereof is represented by SEQ ID NO: 28, FIG. 34); CH3 domains of immunoglobulins; CH4 domains of immunoglobulins; albumin or fragments thereof; albumin-binding peptides; albumin-binding proteins such as streptococcal protein G; and transferrin. Other examples of the "moiety" include a "moiety" that can be linked to a peptide of the present invention via a linker, such as a peptide linker.

Furthermore, a drug may be conjugated to the KLK1 inhibitory peptide, KLK4 inhibitory peptide, or KLK4/KLK8 inhibitory peptide of the present invention in order to exert or enhance the pharmacological activity. Techniques and embodiments known to those skilled in the art as antibody-drug conjugates (ADCs) in the antibody field can become an embodiment of the present invention by replacing the antibody with the peptide of the present invention.

The KLK1 inhibitory peptide, KLK4 inhibitory peptide, or KLK4/KLK8 inhibitory peptide of the present invention may further comprise one or two or more moieties that exhibit binding affinity, inhibitory activity, antagonistic activity, agonistic activity and the like for target molecules other than KLK1, KLK4, or KLK4 and KLK8, or may be conjugated to such moieties. Examples of such a "moiety" include an antibody or a fragment thereof, and a protein having a framework (scaffold) other than an antibody such as a SPINK2 mutant or a fragment thereof. Techniques and embodiments known to those skilled in the art as multispecific antibodies and bispecific antibodies in the field of antibodies can become an embodiment of the conjugate embodiment of the present invention by substituting at least one of two or more "antibodies" contained in those with the peptide of the present invention.

The KLK1 inhibitory peptide, KLK4 inhibitory peptide, or KLK4/KLK8 inhibitory peptide of the present invention or a precursor thereof may contain a signal sequence. A signal sequence present at or added to the N-terminal end of a polypeptide or a precursor thereof is useful to deliver the polypeptide to a specific compartment of a cell, for example, the periplasm in the case of *E. coli* or the endoplasmic reticulum in the case of a eukaryotic cell. Many signal sequences are known to those of skill in the art and can be selected depending on the host cell. Examples of the signal sequence for secreting a desired peptide into the periplasm of *E. coli* include OmpA. The conjugates having a form containing such a signal sequence may also be included within the conjugate of the present invention as an embodiment thereof.

Furthermore, by adding a tag to the KLK1 inhibitory peptide, KLK4 inhibitory peptide, or KLK4/KLK8 inhibitory peptide of the present invention in advance, the peptide can be purified by affinity chromatography.

For example, the peptide of the present invention may have, at the C-terminal end, biotin, a Strep Tag®, a Strep tag II®, oligohistidine such as His6, polyhistidine, an immunoglobulin domain, a maltose binding protein, glutathione-S-transferase (GST), a calmodulin-binding peptide (CBP), a hapten such as digoxigenin or dinitrophenol, an epitope tag such as FLAG®, a myc tag, a HA tag, or the like (hereinafter collectively referred to as "affinity tags"). The peptide to which the tag is added may also be included within the conjugate of the present invention as an embodiment thereof. The conjugate of the present invention, as a whole, may be a peptide (polypeptide).

The KLK1 inhibitory peptide, KLK4 inhibitory peptide, or KLK4/KLK8 inhibitory peptide of the present invention can include a moiety for labeling. Specifically, a labeling moiety such as an enzymatic label, a radioactive label, a colored label, a fluorescent label, a chromogenic label, a luminescent label, hapten, digoxigenin, biotin, a metal complex, a metal, colloidal gold, or the like may be conjugated to the peptide. The peptide which contains the moiety for labeling may also be included within the conjugate of the present invention as an embodiment thereof.

The KLK1 inhibitory peptide, KLK4 inhibitory peptide, or KLK4/KLK8 inhibitory peptide (or an amino acid sequence thereof) of the present invention can contain both natural amino acids and non-natural amino acids, and the natural amino acids can contain both L-amino acids and D-amino acids.

The KLK1 inhibitory peptide, KLK4 inhibitory peptide, or KLK4/KLK8 inhibitory peptide of the present invention may exist as a monomer, a dimer, a trimer or a higher oligomer, or a multimer. The dimer, trimer or higher oligomer and multimer may be either a homomer composed of a single monomer, or a heteromer composed of two or more different monomers. Monomers may, for example, diffuse rapidly and have excellent penetration into tissues. The dimer, oligomer and multimer may have advantages in some aspects, for example, they may have high affinity or binding activity to the target molecule in a local part, may have a slow dissociation rate, or may exhibit high KLK1 inhibitory activity, KLK4 inhibitory activity, or KLK4/KLK8 inhibitory activity. In addition to spontaneous dimerization, oligomerization, and multimerization, the intended dimerization, oligomerization, and multimerization can also be achieved by introducing a jun-fos domain, a leucine zipper or the like into the peptide of the present invention.

The KLK1 inhibitory peptide, KLK4 inhibitory peptide, or KLK4/KLK8 inhibitory peptide of the present invention can bind to one or two or more target molecules or inhibit the activity of the target molecules as a monomer, dimer, trimer or higher oligomer, or a multimer.

The KLK1 inhibitory peptide, KLK4 inhibitory peptide, or KLK4/KLK8 inhibitory peptide of the present invention can be in an isolated form (a lyophilized product, solution, or the like), a conjugate form as described above, or a form bound to another molecule (an immobilized form, a form associated with a different molecule, a form bound to a target molecule, or the like), but is not limited to these, and can take any form suitable for expression, purification, use, storage, or the like.

3. Identification of KLK1 Inhibitory Peptide, KLK4 Inhibitory Peptide, and KLK4/KLK8 Inhibitory Peptide A KLK1 inhibitory peptide, KLK4 inhibitory peptide, or KLK4/KLK8 inhibitory peptide can be identified by a method well known to those skilled in the art, using the amino acid sequence of SPINK2 or the amino acid sequence of the KLK1 inhibitory peptide, KLK4 inhibitory peptide, or KLK4/KLK8 inhibitory peptide of the present invention (for example, the amino acid sequence selected from the group consisting of SEQ ID NOs: 5 to 8 or FIGS. 11 to 14, the group consisting of SEQ ID NOs: 9 to 12 or FIGS. 15 to 18, or the group consisting of SEQ ID NOs: 13 to 22 or FIGS. 19 to 28), a nucleotide sequence encoding the amino acid sequence, a nucleic acid molecule containing the nucleotide sequence and the like as a starting material. As a preferred example, the KLK1 inhibitory peptide, KLK4 inhibitory peptide, or KLK4/KLK8 inhibitory peptide can be identified from a human SPINK2 mutant library, using the KLK1 inhibitory activity, KLK4 inhibitory activity, or KLK4/KLK8 inhibitory activity as an index, respectively, in which binding activity to KLK1, KLK4, or KLK4/KLK8 may be combined as an index, respectively.

In an example, a nucleic acid molecule which is a starting material may be subjected to the induction of mutation therein, and introduced into a suitable bacterial or eukaryotic host using recombinant DNA technology. SPINK2 mutant libraries are known as a technique for identifying a binder to or an inhibitor of a target molecule. For example, a SPINK2 mutant library disclosed in WO2012/105616 is incorporated herein by reference in its entirety. After expressing the nucleotide sequence subjected to the induction of mutation therein in an appropriate host, a clone of a SPIN2 mutant having a desired property, activity, function or the like, whose genotype is linked thereto can be enriched and/or screened, and identified from the library described above. For enrichment and/or screening of the clone, a method known to those skilled in the art, such as a bacterial display method (Francisco, J. A., et al. (1993) Proc. Natl. Acad. Sci. U.S.A., Vol. 90, pp. 10444-10448), a yeast display method (Boder, E. T., et al. (1997) Nat. Biotechnol., Vol. 15, pp. 553-557), a mammalian cell display method (Ho M, et al. (2009) Methods Mol Biol., Vol. 525: pp. 337-52), a phage display method (Smith, G. P. (1985) Science., Vol. 228, pp. 1315-1317), a ribosomal display method (Mattheakis L C, et al. (1994) Proc. Natl. Acad. Sci. U.S.A., Vol. 91, No. 19, pp. 9022-9029), a nucleic acid display method such as an mRNA display method (Nemoto N, et al. (1997) FEBS Lett., Vol. 414, No. 2, pp. 405-408), a colony screening method (Pini, A. et al. (2002) Comb. Chem. High Throughput Screen. Vol. 5, pp. 503-510) or the like can be used. By sequencing the nucleotide sequence of the SPINK2 mutant contained in the screened and identified clone, the amino acid sequence encoded by the nucleotide sequence can be determined as the amino acid sequence of the SPINK2 mutant, i.e., the KLK1 inhibitory peptide, KLK4 inhibitory peptide, or KLK4/KLK8 inhibitory peptide, contained in the clone.

The SPINK2 mutant of the present invention can be obtained, for example, by inducing mutation in naturally occurring SPINK2. The term "inducing mutation" means causing one or two or more amino acids present at respective positions of an amino acid sequence to be substituted with another amino acid or to be deleted, or causing addition or insertion of an amino acid that is not present in the original amino acid sequence. Such deletion, addition or insertion may alter the sequence length. In the SPINK2 mutant of the present invention, the induction of a mutation may preferably occur at one or two or more positions of $X_1$ to $X_{13}$ in the amino acid sequence represented by SEQ ID NO: 23 (FIG. 29).

However, ones which maintain, after inducing such a suitable mutation, a natural amino acid, which is the same amino acid as the amino acid present in the naturally occurring amino acid sequence at a specific position, in one or two or more positions of $X_1$ to $X_{13}$, are also included within the scope of the mutant as long as they have at least one mutated amino acid overall. Likewise, in an embodiment of the present invention, ones which maintain, after inducing a mutation in one or more positions in the regions other than $X_1$ to $X_{13}$, a natural amino acid that is the same amino acid as the amino acid present in the naturally occurring amino acid sequence at a specific position, are also included within the scope of the mutants as long as they have at least one mutated amino acid overall.

The term "inducing random mutation" means that the induction of a mutation at a specific position on a sequence causes the introduction of one or two or more different amino acids each with a certain probability of being introduced at the specific position, and wherein each of the probabilities for at least two of the different amino acids to be introduced are not necessarily the same. Furthermore, in the present invention, said at least two different amino acids may include a naturally occurring (wild type) amino acid (one sort of amino acid), and this case is also included within the scope of the term "inducing random mutation".

As regards a method for inducing a random mutation at a specific position, a standard method known to those skilled in the art can be used. For example, a mutation can be induced at a specific position in the sequence by PCR (polymerase chain reaction) using a mixture of synthetic oligonucleotides containing a degenerate nucleotide composition. For example, the use of the codon NNK or NNS (N=adenine, guanine, cytosine or thymine; K=guanine or thymine; S=adenine or cytosine) induces mutations in which all 20 natural amino acids as well as stop codons can be introduced. Whereas, with the use of the codon VVS (V=adenine, guanine or cytosine) there is no possibility of causing introductions of Cys, Ile, Leu, Met, Phe, Trp, Tyr, and Val, but mutations introducing the remaining 12 natural amino acids can be induced. Furthermore, for example, with the use of the codon NMS (M=adenine or cytosine) there is no possibility of causing introductions of Arg, Cys, Gly, Ile, Leu, Met, Phe, Trp and Val, but mutations introducing the remaining 11 natural amino acids can be induced. Special codons, artificial codons, or the like can be used to induce a mutation that results in the introduction of non-natural amino acids.

Site-specific induction of mutation can also be performed using structural information of a target having a higher-order structure and/or a peptide against the target or a wild-type peptide from which the peptide is derived. In the present invention, a site-specific mutation can be introduced using structural information including higher-order information of the target KLK1, KLK4, or KLK8, and/or a SPINK2 mutant or wild-type SPINK2 against KLK1, KLK4, or KLK4 and KLK8, or a complex of the both. For example, structural information obtained by identifying a SPINK2 mutant having KLK1 inhibitory activity, KLK4 inhibitory activity, or KLK4/KLK8 inhibitory activity; performing X-ray crystal structure analysis after obtaining a crystal of a complex of KLK1, KLK4 or KLK8 and the SPINK2 mutant; and identifying, based on the analysis result, an epitope on the KLK1, KLK4, or KLK8 molecule to which the SPINK2 mutant binds and a paratope on the SPINK2 mutant corresponding to the epitope, can be found to have a correlation with the KLK1 inhibitory activity, KLK4 inhibitory activity, or KLK4/KLK8 inhibitory activity. Based on such a structure-activity relationship, it is possible to design a substitution with a specific amino acid at a specific position, an insertion or deletion of an amino acid at a specific position, or the like, and actually confirm the KLK1 inhibitory activity, KLK4 inhibitory activity, or KLK4/KLK8 inhibitory activity.

In addition, the induction of mutation can be performed, for example, with a nucleotide element having altered base-pair specificity, such as inosine.

Furthermore, inducing mutations at random positions is possible, for example, by error-prone PCR using a DNA polymerase that lacks a proofreading function and has a high error rate, such as Taq DNA polymerase, by chemical mutagenesis, or the like.

The KLK1 inhibitory peptide, KLK4 inhibitory peptide, or KLK4/KLK8 inhibitory peptide can be enriched and/or screened by using bacterial display, yeast display, mammalian cell display, phage display, ribosome display, nucleic acid display, colony screening or the like, from libraries known to those skilled in the art, such as a phage library and a colony library, suitable for each screening method. These libraries can be constructed with vectors and methods known to those skilled in the art, suitable for each library, such as phagemid for phage library, and cosmid for colony screening. Such vectors may be viruses or viral vectors that infect prokaryotic or eukaryotic cells. These recombinant vectors can be prepared by a method known to those skilled in the art, such as genetic engineering.

The bacterial display is a technique for presenting a desired protein on the surface of *E. coli*, for example, by fusing the desired protein to a part of the outer membrane lipoprotein (Lpp) of *E. coli* and the outer membrane protein OmpA. A library presenting a group of randomly mutated proteins on the surface of the transformed bacterial cells can be obtained by inducing random mutations in a nucleotide sequence encoding an amino acid sequence of a certain protein, introducing each sequence from the DNA group obtained by the induction of the random mutations into a vector suitable for bacterial display, and transforming bacterial cells with the vector (Francisco, J. A., et al. (1993), Proc. Natl. Acad. Sci. U.S.A. Vol. 90, pp. 10444-10448).

The yeast display is a technique for presenting a desired protein on the surface of yeast by fusing the desired protein to a protein such as α-agglutinin present on the outer shell of the cell surface of the yeast. The 06-agglutinin includes a C-terminal hydrophobic region that is presumed to be a glycosylphosphatidylinositol (GPI) anchor attachment signal, a signal sequence, an active domain, a cell wall domain, and the like. With manipulation of these elements, it is possible to display a desired protein on the cell surface of yeast. A library presenting a group of randomly mutated proteins on the surface of transformed yeast cells can be obtained by inducing random mutations in a nucleotide sequence encoding an amino acid sequence of a certain protein, introducing each sequence from the DNA group obtained by the induction of the random mutations into a vector suitable for yeast display, and transforming yeast cells with the vector (Ueda, M.& Tanaka, A., Biotechnol. Adv., Vol. 18, p. 121 (2000): Ueda, M.& Tanaka, A., J. Biosci. Bioeng., Vol. 90, p. 125 (2000), and other literatures).

The animal cell display is a technique for presenting a desired protein on the surface of mammalian cells such as HEK293 or Chinese hamster ovary (CHO) cells by, for example, fusing a desired protein to a transmembrane region of a membrane protein such as a platelet-derived growth factor receptor (PDGFR). A library presenting a group of randomly mutated proteins on the surface of transformed animal cells can be obtained by inducing random mutations in a nucleotide sequence encoding an amino acid sequence of a certain protein, introducing each sequence from the DNA group obtained by the induction of the random mutations into a vector suitable for animal cell display, and transforming animal cells with the vector (Ho M, et al. (2009) Methods Mol Biol. Vol. 525: pp. 337-52).

The desired library presented on cells such as yeast, bacteria, and animal cells can be incubated in the presence of the target molecule or contacted with the target molecule. For example, KLK1, KLK4 or KLK8 modified with biotin or the like and cells containing the library are incubated for a certain period of time, then a carrier such as magnetic beads is added, and the cells are separated from the carrier, and subsequently the carrier is washed to remove non-specific adsorbing substances or binding substances, thus the cell group presenting the peptide, the peptide mixtures or the concentrated peptide mixtures bound to the carrier (or KLK1, KLK4, or KLK8 bound to the carrier) can be recovered. Similarly, the cell group presenting the peptide, the peptide assembly or the concentrated peptide assembly bound to the carrier (or KLK1, KLK4 or KLK8 bound to the carrier) or KLK1, KLK4 or KLK8 can be recovered by performing magnetic cell separation (MACS) after adding magnetic beads, or by performing FACS after cell staining using anti-KLK1, anti-KLK4 or anti-KLK8 antibodies. Non-specific adsorption sites and/or binding sites can be subjected to, for example, blocking treatment, and a blocking step by an appropriate method may be incorporated. By recovering a vector expressing the peptide thus obtained, the peptide assembly or the concentrated peptide assembly, and then sequencing a nucleotide sequence of the polynucleotide inserted into the vector, the amino acid sequence encoded by the nucleotide sequence can be determined. In addition, the peptide assembly that binds to the target molecule can be highly concentrated by introducing the vector again into the host cell, and repeating the above procedures as a cycle once or several times.

In phage display, phagemid is a bacterial plasmid, for example, containing a second origin of replication derived from a single-stranded bacteriophage, in addition to the origin of plasmid replication. Cells containing a phagemid can replicate the phagemid through a single-stranded replication mode, when co-infected with M13 or a similar helper bacteriophage. That is, single-stranded phagemid DNA is packaged in infectious particles coated with a bacteriophage coat protein. In this manner, phagemid DNA can be formed as a clonal double-stranded DNA plasmid in infected bacteria, or phagemid can be formed as bacteriophage-like particles from the culture supernatant of co-infected cells, respectively. The bacteriophage-like particles themselves can be formed again as plasmids by injecting the particles into a bacterium having an F-pilus to infect the bacterium with such DNA.

By inserting a fusion gene containing a polynucleotide having a nucleotide sequence encoding an amino acid sequence of a test peptide and a bacteriophage coat protein gene into such a phagemid, and infecting the bacteria with the phagemid, and then culturing the cell, it is possible to cause such a peptide to be expressed or presented (in other words, displayed) on the bacteria or phage-like particles, or to be produced in phage particles or in the culture supernatant of the bacteria as a fusion protein with the coat protein.

For example, by inserting a fusion gene containing the polynucleotide and a bacteriophage coat protein gene gpIII into a phagemid, and then co-infecting phagemid into *E. coli* along with M13 or a similar helper phage, it is possible to cause such a peptide to be produced in the culture supernatant of *E. coli* as a fusion protein containing the peptide and the coat protein.

When various circular or non-circular vectors such as viral vectors are used instead of the phagemid, it is possible to cause a peptide having an amino acid sequence encoded by the nucleotide sequence of the polynucleotide inserted into such a vector, according to a method known to those skilled in the art, to be expressed or presented on the cell or virus-like particles into which the vector has been introduced, or to be produced in a culture supernatant of the cell.

The library expressing the peptide thus obtained can be incubated in the presence of the target molecule or contacted with the target molecule. For example, a carrier on which KLK1, KLK4, or KLK4 and/or KLK8 is immobilized is incubated with a mobile phase containing the library for a certain period of time, then the mobile phase is separated from the carrier, and then the carrier is washed to remove non-specific, adsorbing substances or binding substances, thus the peptide, the peptide mixtures or the concentrated peptide mixtures bound to the carrier (or KLK1, KLK4, or KLK4 and/or KLK8 bound to the carrier) can be recovered by elution. Elution can be performed non-selectively under relatively high ionic strength, low pH, moderate denaturing conditions, the presence of chaotropic salts, or the like, or performed selectively by adding a soluble target molecule such as KLK1, KLK4, or KLK8, an antibody bound to the target molecule, a natural ligand, a substrate and the like to compete with the immobilized target molecule. Non-specific, adsorption sites and/or binding sites can be subjected to, for example, blocking treatment, and a blocking step by an appropriate method may be incorporated.

By recovering a vector expressing the peptide thus obtained, or a peptide assembly or a concentrated peptide assembly, then sequencing the nucleotide sequences of the polynucleotide inserted into the vector, the amino acid sequence encoded by the nucleotide sequence can be determined. In addition, the peptide assembly that binds to the target molecule can be highly concentrated by introducing the vector again into the host cell, and repeating the above procedures as a cycle once or several times.

The ribosomal display is a technique for synthesizing in a test tube a molecule in which a desired protein is associated with an mRNA corresponding to it and a ribosome, for example, by using an mRNA encoding the desired protein without a termination codon, and a cell-free protein synthesis system. A library presenting a group of randomly mutated proteins on ribosomes can be obtained by using an mRNA group obtained by inducing random mutations in a nucleotide sequence encoding an amino acid sequence of a certain protein, and a cell-free protein synthesis system (Mattheakis L C, et al. (1994) Proc. Natl. Acad. Sci. U.S.A. Vol. 91, No. 19, pp. 9022-9029).

The nucleic acid display is also called mRNA display, and is a technique for synthesizing, for example, a molecule in which a desired protein is associated with an mRNA encoding it and a ribosome, by using a linker such as puromycin having a structure similar to the 3' end of tyrosyl t-RNA. Since this technique uses a cell-free protein synthesis system, not living cells, it is possible to perform the synthesis in vitro. A library presenting a group of randomly mutated proteins on ribosomes can be obtained by using an mRNA group obtained by inducing random mutations in a nucleotide sequence encoding an amino acid sequence of a certain protein, a linker such as puromycin, and a cell-free protein synthesis system (Nemoto N, et al. (1997) FEBS Lett. Vol. 414, No. 2, pp. 405-408).

A library expressing peptides obtained via a cell-free synthesis system such as ribosome display or nucleic acid display can be incubated in the presence of the target molecule or contacted with the target molecule. For example, a carrier on which KLK1, KLK4, or KLK4 and/or KLK8 is immobilized is incubated with a mobile phase containing the library for a certain period of time, then the mobile phase is separated from the carrier, and then the carrier is washed to remove non-specific, adsorbing substances or binding substances, thus the peptide, the peptide assembly or the concentrated peptide assembly bound to the carrier (or KLK1, KLK4, or KLK4 and/or KLK8 bound to the carrier) can be recovered by elution. Elution can be performed non-selectively under relatively high ionic strength, low pH, moderate denaturing conditions, the presence of chaotropic salts, or the like, or performed selectively by adding a soluble target molecule such as KLK1, KLK4, or KLK8, an antibody bound to the target molecule, a natural ligand, a substrate and the like to compete with the immobilized target molecule. Non-specific, adsorption sites and/or binding sites can be subjected to, for example, blocking treatment, and a blocking step by an appropriate method may be incorporated.

The nucleic acid expressing the peptide, the peptide assembly or the concentrated peptide assembly thus obtained is recovered, and, after a reverse transcription reaction to cDNA in the case of mRNA, the nucleotide sequence is sequenced, then the amino acid sequence encoded by the nucleotide sequence can be determined. In addition, the peptide assembly that binds to the target molecule can be highly concentrated by transcribing mRNA from the recovered nucleic acid, and repeating the procedures described above as a cycle once to several times.

When an affinity tag is in advance conjugated to the peptide, the peptide assembly or the concentrated peptide assembly, the peptide or the peptide assembly can be efficiently purified. For example, when a protease substrate is in advance conjugated to a peptide assembly as a tag, the peptide can be eluted by cleaving with protease activity.

By inducing further mutation in the obtained clone or library based on the obtained sequence information and the function of the peptide, it is also possible to obtain a peptide with improved function (for example, KLK1 inhibitory activity, KLK4 inhibitory activity, or KLK4/KLK8 inhibitory activity), physicochemical properties (thermal stability, storage stability, or the like), pharmacokinetics (distribution, half-life in blood) and the like from the library to which the mutation has been introduced.

A KLK1 inhibitory peptide, KLK4 inhibitory peptide, or KLK4/KLK8 inhibitory peptide can be identified by determining whether or not the obtained peptide has KLK1 inhibitory activity, KLK4 inhibitory activity, or KLK4/KLK8 inhibitory activity, respectively.

The KLK1 inhibitory peptide, KLK4 inhibitory peptide, or KLK4/KLK8 inhibitory peptide may preferably maintain a conformation including a loop structure consisting of the amino acids from Ser 16 to Val 30, a β sheet composed of β strand (1) consisting of Cys 31 and Gly 32 and β strand (2) consisting of the amino acids from Ile 57 to Arg 59, and an α helix consisting of Glu 41 to Gly 51 which are comprised in the amino acid sequence of the wild-type SPINK2, or a loop structure, a β sheet and an α helix similar thereto or at least partially corresponding thereto (or to the positions thereof) to the extent that KLK1 inhibitory activity, KLK4 inhibitory activity, or KLK4/KLK8 inhibitory activity can be exerted, respectively. It is also possible to identify a more preferred KLK1 inhibitory peptide, KLK4 inhibitory peptide, or KLK4/KLK8 inhibitory peptide, using the conformation (the entire structure or a partial structure) as a part of an index.

4. Nucleic Acid Molecule Encoding KLK1 Inhibitory Peptide, KLK4 Inhibitory Peptide, or KLK4/KLK8 Inhibitory Peptide, Vector Comprising the Same, Cell Comprising the Same, and Method for Producing Recombinant KLK1 Inhibitory Peptide, KLK4 Inhibitory Peptide, or KLK4/KLK8 Inhibitory Peptide The present invention also provides a polynucleotide containing a nucleotide sequence encoding an amino acid sequence contained in a KLK1 inhibitory peptide, KLK4 inhibitory peptide, or KLK4/KLK8 inhibitory peptide (hereinafter referred to as "nucleic acid molecule encoding a KLK1 inhibitory peptide", "nucleic acid molecule encoding a KLK4 inhibitory peptide", or "nucleic acid molecule encoding a KLK4/KLK8 inhibitory peptide", respectively), a recombinant vector into which the gene has been inserted, a cell into which the gene or vector has been introduced (hereinafter referred to as a "cell containing a nucleic acid molecule encoding a KLK1 inhibitory peptide", "cell containing a nucleic acid molecule encoding a KLK4 inhibitory peptide", or "cell containing a nucleic acid molecule encoding a KLK4/KLK8 inhibitory peptide"), and a cell producing a KLK1 inhibitory peptide, KLK4 inhibitory peptide, or KLK4/KLK8 inhibitory peptide (hereinafter referred to as "KLK1 inhibitory peptide-producing cell", "KLK4 inhibitory peptide-producing cell", or "KLK4/KLK8 inhibitory peptide-producing cell", respectively).

Preferred examples of the nucleic acid molecules encoding the KLK1 inhibitory peptide, KLK4 inhibitory peptide, or KLK4/KLK8 inhibitory peptide of the present invention include ones having the nucleotide sequence described in any one of the following (a1) to (a4), (b1) to (b4), or (c1) to (c4), respectively (hereinafter referred to as "nucleotide sequence of a KLK1 inhibitory peptide", "nucleotide sequence of a KLK4 inhibitory peptide" or "nucleotide sequence of a KLK4/KLK8 inhibitory peptide", respectively); one consisting of a nucleotide sequence containing a nucleotide sequence of a KLK1 inhibitory peptide, a nucleotide sequence of a KLK4 inhibitory peptide or a nucleotide sequence of a KLK4/KLK8 inhibitory peptide; or one consisting of a nucleotide sequence of a KLK1 inhibitory peptide, a nucleotide sequence of a KLK4 inhibitory peptide or a nucleotide sequence of a KLK4/KLK8 inhibitory peptide:

(a1) a nucleotide sequence encoding the amino acid sequence represented by any one of SEQ ID NOs: 5 to 8 (FIGS. 11 to 14);

(a2) a nucleotide sequence that hybridizes with a nucleotide sequence complementary to the nucleotide sequence described in (a1) under stringent conditions, and encodes an amino acid sequence contained in a peptide having KLK1 inhibitory activity;

(a3) a nucleotide sequence having 1 to 20, 1 to 15, 1 to 10, 1 to 8, 1 to 6, 1 to 5, 1 to 4, 1 to 3, 1 to 2, or 1 nucleotide or nucleotide residue substitution, deletion, addition and/or insertion in the nucleotide sequence described in (a1), and encoding an amino acid sequence contained in a peptide having KLK1 inhibitory activity; and (a4) a nucleotide sequence that is 60%, 70%, 80%, 85%, 90%, 92%, 94%, 96%, 97%, 98%, or 99% or more identical to the nucleotide sequence described in (a1), and encoding an amino acid sequence contained in a peptide having KLK1 inhibitory activity, (b1) a nucleotide sequence encoding the amino acid sequence represented by any one of SEQ ID NOs: 9 to 12 (FIGS. 15 to 18);

(b2) a nucleotide sequence that hybridizes with a nucleotide sequence complementary to the nucleotide sequence described in (b1) under stringent conditions, and encodes an amino acid sequence contained in a peptide having KLK4 inhibitory activity;

(b3) a nucleotide sequence having 1 to 20, 1 to 15, 1 to 10, 1 to 8, 1 to 6, 1 to 5, 1 to 4, 1 to 3, 1 to 2, or 1 nucleotide or nucleotide residue substitution, deletion, addition and/or insertion in the nucleotide sequence described in (b1), and encoding an amino acid sequence contained in a peptide having KLK4 inhibitory activity; and (b4) a nucleotide sequence that is 60%, 70%, 80%, 85%, 90%, 92%, 94%, 96%, 97%, 98%, or 99% or more identical to the nucleotide sequence described in (b1), and encoding an amino acid sequence contained in a peptide having KLK4 inhibitory activity, (c1) a nucleotide sequence encoding the amino acid sequence represented by any one of SEQ ID NOs: 13 to 22 (FIGS. 19 to 28);

(c2) a nucleotide sequence that hybridizes with a nucleotide sequence complementary to the nucleotide sequence described in (c1) under stringent conditions, and encodes an amino acid sequence contained in a peptide having KLK4/KLK8 inhibitory activity;

(c3) a nucleotide sequence having 1 to 20, 1 to 15, 1 to 10, 1 to 8, 1 to 6, 1 to 5, 1 to 4, 1 to 3, 1 to 2, or 1 nucleotide or nucleotide residue substitution, deletion, addition and/or insertion in the nucleotide sequence described in (c1), and encoding an amino acid sequence contained in a peptide having KLK4/KLK8 inhibitory activity; and (c4) a nucleotide sequence that is 60%, 70%, 80%, 85%, 90%, 92%, 94%, 96%, 97%, 98%, or 99% or more identical to the nucleotide sequence described in (c1), and encoding an amino acid sequence contained in a peptide having KLK4/KLK8 inhibitory activity.

The SPINK2 mutant peptide consisting of or containing the amino acid sequence encoded by the nucleotide sequence described in any one of (a1) to (a4), (b1) to (b4), or (c1) to (c4) above inhibits the protease activity of KLK1, KLK4, or KLK4 and KLK8, and preferably, specifically inhibits the protease activity.

However, the nucleic acid molecule encoding the KLK1 inhibitory peptide, KLK4 inhibitory peptide, or KLK4/KLK8 inhibitory peptide is not limited to (a1) to (a4), (b1) to (b4), or (c1) to (c4), and the nucleic acid molecule containing the nucleotide sequence encoding the amino acid sequence contained in the SPINK2 mutant having KLK1 inhibitory activity, KLK4 inhibitory activity, or KLK4/KLK8 inhibitory activity, preferably the amino acid sequence represented by SEQ ID NO: 23 (FIG. 29) is fully encompassed within the scope of the nucleic acid molecule encoding the KLK1 inhibitory peptide, KLK4 inhibitory peptide, or KLK4/KLK8 inhibitory peptide.

To design a nucleotide sequence encoding an amino acid sequence, one or two or more codons corresponding to each amino acid may be used. Thus, the nucleotide sequence encoding a single amino acid sequence contained in a certain peptide can have a plurality of variations.

In selecting such codons, the codon can be appropriately selected according to the codon usage of the host cell for expression to which a polynucleotide having the nucleotide sequence or a vector containing the same can be introduced, and the frequency or ratio of use of multiple codons can be adjusted appropriately. For example, when *E. coli* is used as a host cell, a nucleotide sequence may be designed using codons that are frequently used in *E. coli*.

A nucleic acid molecule encoding the KLK1 inhibitory peptide, KLK4 inhibitory peptide, or KLK4/KLK8 inhibitory peptide may be operably linked to one or two or more regulatory sequences. The term "operably linked" means that it can express the linked nucleic acid molecule or allows the expression of the nucleotide sequence contained in the molecule. Regulatory sequences include sequence elements that include information about transcriptional and/or translational regulation. Regulatory sequences vary from species to species, but generally include a promoter, and 5' non-coding sequences involved in transcription and translation initiation, exemplified by the −35/−10 box and Shine Dalgarno sequence in prokaryotes, and the TATA box, CAAT sequence, and 5' capping sequence in eukaryotes. Such sequences may include an enhancer element and/or a repressor element, as well as a signal sequence, a leader sequence, and the like, which may be translated, to deliver native or mature peptides to specific compartments inside or outside of the host cell. Furthermore, regulatory sequences may contain 3' non-coding sequence, and such a sequence may include elements involved in transcriptional termination, polyadenylation, or the like. Here, if the sequence for transcriptional termination does not function sufficiently in a particular host cell, it can be replaced with a sequence suitable for that cell.

Examples of the promoter sequence include a tet promoter, a lacUV5 promoter, a T7 promoter or the like in prokaryotes, and an SV40 promoter, a CMV promoter or the like in eukaryotic cells.

The nucleic acid molecule encoding the KLK1 inhibitory peptide, nucleic acid molecule encoding the KLK4 inhibitory peptide, or nucleic acid molecule encoding the KLK4/KLK8 inhibitory peptide may be, but are not limited to, in an isolated form or in a form contained in a vector or other cloning vehicle (hereinafter, simply referred to as a "vector": such as a plasmid, phagemid, phage, baculovirus, or cosmid) or a form in a chromosome. The vector may include, in addition to the above regulatory sequences, a replication sequence and a control sequence suitable for the host cell used for expression, as well as a selection marker that provides a cell to which a nucleic acid molecule has been introduced by transformation or the like with a selectable phenotype.

A nucleic acid molecule encoding the KLK1 inhibitory peptide, nucleic acid molecule encoding the KLK4 inhibitory peptide, or nucleic acid molecule encoding the KLK4/KLK8 inhibitory peptide and a vector containing a nucleotide sequence of the KLK1 inhibitory peptide, vector containing a nucleotide sequence of the KLK4 inhibitory peptide, or vector containing a nucleotide sequence of the KLK4/KLK8 inhibitory peptide can be introduced into a host cell capable of expressing the peptide or nucleotide sequence by a method known to those skilled in the art such as transformation. The host cell to which the nucleic acid molecule or vector has been introduced may be cultured under conditions suitable for expression of the peptide or nucleotide sequence. The host cell may be either a prokaryotic cell or a eukaryotic cell. Examples of the prokaryotic cells include *Escherichia coli* and *Bacillus subtilis*. Examples of the eukaryotic cells include yeasts such as *Saccharomyces cerevisiae* and *Pichia pastoris*, insect cells such as SF9 and High5, and animal cells such as HeLa cell, CHO cell, COS cell and NS0. By using the eukaryotic cell or the like as a host cell, the expressed peptide of the present invention can be subjected to desired post-translational modification. Examples of the post-translational modifications include addition of functional groups such as a sugar chain, addition of a peptide or a protein, and conversion of amino acid chemical properties. It is also possible to artificially apply desired modifications to the peptide of the present invention. Such modified peptides are also encompassed within the scope of the "peptide" of the present invention.

The present invention also provides a method for producing the KLK1 inhibitory peptide, KLK4 inhibitory peptide, or KLK4/KLK8 inhibitory peptide. The method includes step 1 of culturing a cell containing a nucleic acid molecule encoding the KLK1 inhibitory peptide or a cell producing the KLK1 inhibitory peptide, a cell containing a nucleic acid molecule encoding the KLK4 inhibitory peptide or a cell producing the KLK4 inhibitory peptide, or a cell containing a nucleic acid molecule encoding the KLK4/KLK8 inhibitory peptide or a cell producing the KLK4/KLK8 inhibitory peptide, and/or step 2 of recovering the SPINK2 mutant from the culture obtained in step 1. For step 2, a procedure known to those skilled in the art such as fractionation, chromatography, purification or the like can be applied. For example, a purification by affinity chromatography using the antibody of the present invention as described later can be applied.

In some embodiments of the present invention, the KLK1 inhibitory peptide, KLK4 inhibitory peptide, or KLK4/KLK8 inhibitory peptide has an intramolecular disulfide bond. It is sometimes preferred to deliver a peptide having an intramolecular disulfide bond to a cell compartment having an oxidative redox environment by using a signal sequence or the like. The oxidative environment can be provided by the periplasm of gram-negative bacteria such as *E. coli*, the extracellular environment of gram-positive bacteria, the endoplasmic reticulum lumen of eukaryotic cells, and the like. Under such circumstances, structural disulfide bond formation can be promoted. It is also possible to produce a peptide having an intramolecular disulfide bond in the cytoplasm of a host cell such as *E. coli*. In that case, the peptide may be obtained directly in a soluble folded state, or may be recovered in an encapsulated form, and then refolded in vitro. Furthermore, it is also possible to select a host cell having an oxidative intracellular environment, and produce a peptide having an intramolecular disulfide bond in the cytoplasm of the host cell. When the KLK1 inhibitory peptide, KLK4 inhibitory peptide, or KLK4/KLK8 inhibitory peptide does not have an intramolecular disulfide bond, the peptide can be produced in a cell compartment having a reductive redox environment, for example, in the cytoplasm of gram-negative bacteria.

The KLK1 inhibitory peptide, KLK4 inhibitory peptide, or KLK4/KLK8 inhibitory peptide of the present invention can also be produced by other methods known to those skilled in the art, such as solid phase peptide synthesis methods, for example, the Merrifield method; chemical synthesis methods represented by organic synthetic chemical peptide synthesis methods using t-butoxycarbonyl (Boc), 9-fluorenylmethoxycarbonyl (Fmoc) or the like; and in vitro translation.

The present invention provides, in some embodiments thereof, an antibody that binds to a SPINK2 mutant peptide having KLK1 inhibitory activity, KLK4 inhibitory activity, or KLK4/KLK8 inhibitory activity, and a binding fragment thereof. The antibody may be either a polyclonal antibody or a monoclonal antibody, and the monoclonal antibody is not particularly limited as long as it is an immunoglobulin or a derivative thereof. The functional fragment of the antibody is not limited as long as it has antigen-binding activity, i.e., binding activity to the SPINK2 mutant peptide. Examples thereof include both or one of the heavy and light chains, fragments thereof, ones lacking a constant region and/or Fc region, and a conjugate with another protein or a labeling substance. Such antibodies and functional fragments thereof can be prepared by a method known to those skilled in the art, and they are useful for: purification of the SPINK2 mutant peptide by affinity chromatography, clinical tests related to a pharmaceutical composition containing the peptide or a use thereof, detection of the peptide in diagnosis or the like, immunoassay, and the like. The antibody of the present invention can be purified by affinity chromatography using the peptide of the present invention to which the antibody binds.

5. Pharmaceutical Composition

The present invention also provides a pharmaceutical composition comprising a KLK1 inhibitory peptide, KLK4 inhibitory peptide, or KLK4/KLK8 inhibitory peptide or a conjugate thereof.

The pharmaceutical composition of the present invention comprising a KLK1 inhibitory peptide or a conjugate thereof is useful for the treatment and/or prevention of various diseases which are elicited or exacerbated by KLK1 and in which the inhibition or suppression of the expression or function of KLK1 can suppress the elicitation or exacerbation, bring a cure, maintain or improve symptoms, avoid secondary diseases, or the like (hereinafter, the diseases are referred to as "diseases related to KLK1" or "KLK1-related diseases"). Examples of diseases related to KLK1 include cardiovascular diseases such as hypotension, kidney diseases, acute pancreatitis, bronchitis, and asthma.

The pharmaceutical composition of the present invention comprising a KLK4 inhibitory peptide or a conjugate thereof is useful for the treatment and/or prevention of various diseases which are elicited or exacerbated by KLK4 and in which the inhibition or suppression of the expression or function of KLK4 can suppress the elicitation or exacerbation, bring a cure, maintain or improve symptoms, avoid secondary diseases, or the like (hereinafter, the diseases are referred to as "diseases related to KLK4" or "KLK4-related disease"). Examples of diseases related to KLK4 include hereditary enamel hypoplasia, and prostate cancer.

The pharmaceutical composition of the present invention comprising a KLK4/KLK8 inhibitory peptide or a conjugate thereof is useful for the treatment and/or prevention of various diseases which are elicited or exacerbated by KLK4 and KLK8 and in which the inhibition or suppression of the expression or function of KLK4 and KLK8 can suppress the elicitation or exacerbation, bring a cure, maintain or improve symptoms, avoid secondary diseases, or the like (hereinafter, the diseases are referred to as "diseases related to KLK4/KLK8" or "KLK4/KLK8-related disease"). Examples of diseases related to KLK4/KLK8 include hereditary enamel hypoplasia, prostate cancer, long-term memory inhibition, schizophrenia, colon cancer, and ovarian cancer.

In the present invention, KLK8-related disease (sometime referred to as "diseases related to KLK8") means various diseases which are elicited or exacerbated by KLK8 and in which the inhibition or suppression of the expression or function of KLK4 and KLK8 can suppress the elicitation or exacerbation, bring a cure, maintain or improve symptoms, avoid secondary diseases, or the like. Examples of KLK8-related disease include long-term memory inhibition, schizophrenia, colon cancer, and ovarian cancer.

However, the diseases related to KLK1, diseases related to KLK4, and diseases related to KLK4/KLK8 are not limited to the diseases exemplified herein.

The pharmaceutical composition of the present invention can contain a therapeutically or prophylactically effective amount of the KLK1 inhibitory peptide, KLK4 inhibitory peptide, or KLK4/KLK8 inhibitory peptide, and a pharmaceutically acceptable diluent, a carrier, a solubilizer, an emulsifier, a preservative and/or an adjuvant.

The term "therapeutically or prophylactically effective amount" means an amount that exerts an effect of treatment or prevention on a particular disease, in an administration form and through an administration route. The term "therapeutically or prophylactically effective amount" has the same meaning as the term "pharmacologically effective amount".

The pharmaceutical composition of the present invention can contain a substance for altering, maintaining or retaining pH, osmotic pressure, viscosity, transparency, color, isotonicity, sterility, stability of the composition or peptides, conjugates or the like contained therein, solubility, sustained release, absorptivity, osmotic properties, dosage forms, strengths, properties, shapes, and the like (hereinafter referred to as "substance for formulation"). The substance for formulation is not particularly limited as long as they are pharmacologically acceptable. For example, non-toxicity or low toxicity is a property which the substance for formulation preferably has.

Examples of the substance for formulation include, but are not limited to, amino acids such as glycine, alanine, glutamine, asparagine, histidine, arginine, or lysine; antibacterial agents; antioxidants such as ascorbic acid, sodium sulfate, or sodium bisulfite; buffering agents such as phosphoric acid, citric acid, boric acid buffer, sodium hydrogen carbonate, and Tris-HCl solution; fillers such as mannitol and glycine; chelating agents such as ethylenediaminetetraacetic acid (EDTA); complexing agents such as caffeine, polyvinylpyrrolidine (polyvinylpyrrolidone), β-cyclodextrin and hydroxypropyl-β-cyclodextrin; bulking agents such as glucose, mannose, or dextrin; monosaccharides, disaccharides, and other carbohydrates such as glucose, mannose and dextrin; coloring agents: flavoring agents: diluents: emulsifiers; hydrophilic polymers such as polyvinylpyrrolidine: low molecular weight polypeptides; salt-forming counterions: benzalkonium chloride; preservatives such as benzoic acid, salicylic acid, thimerosal, phenethyl alcohol, methylparaben, propylparaben, chlorexidine, sorbic acid, or hydrogen peroxide; solvents such as glycerin, propylene glycol, or polyethylene glycol; sugar alcohols such as mannitol or sorbitol; suspending agents; PEG; sorbitan esters;

polysorbates such as polysorbate 20 or polysorbate 80; surfactants such as triton, tromethamine, lecithin or cholesterol; stabilization enhancers such as sucrose or sorbitol; elastic enhancers such as sodium chloride, potassium chloride, mannitol or sorbitol; transport agents; diluents; excipients; and/or pharmaceutical adjuvants.

The amount of these substances for formulation is added at 0.001 to 1000 times, preferably 0.01 to 100 times, more preferably 0.1 to 10 times the weight of the KLK1 inhibitory peptide, KLK4 inhibitory peptide, or KLK4/KLK8 inhibitory peptide.

A pharmaceutical composition containing the KLK1 inhibitory peptide, KLK4 inhibitory peptide, or KLK4/KLK8 inhibitory peptide in a liposome or a pharmaceutical composition containing a modified product of the peptide linked to a liposome is also included within the pharmaceutical composition of the present invention.

The excipient and carrier are usually liquid or solid, and are not particularly limited as long as they are substances used for oral or parenteral administration such as water for injection, physiological saline, artificial cerebrospinal fluid and similar others. Examples of the physiological saline include ones which are neutral and ones containing serum albumin.

Examples of the buffer include a Tris buffer prepared so that the final pH of the pharmaceutical composition is set to be 7.0 to 8.5, an acetate buffer prepared similarly to be 4.0 to 5.5, a citrate buffer prepared similarly to be 5.0 to 8.0, and a histidine buffer prepared similarly to be 5.0 to 8.0.

The pharmaceutical composition of the present invention is a solid, a liquid, a suspension, or the like. Other examples of the pharmaceutical composition of the present invention include a lyophilized formulation. An excipient such as sucrose can be used to form the lyophilized preparation.

The administration route of the pharmaceutical compositions of the present invention may be any of eye drops, enteral administration, topical administration, and parenteral administration, and specific examples thereof include eye drops applied to the conjunctiva, intravitreal administration, intravenous administration, intraarterial administration, intramuscular administration, intradermal administration, subcutaneous administration, intraperitoneal administration, transdermal administration, intraosseous administration, and intraarticular administration.

The composition of such a pharmaceutical composition should be determined according to the administration method, inhibitory activity or binding affinity of the KLK1 inhibitory peptide, KLK4 inhibitory peptide, or KLK4/KLK8 inhibitory peptide against KLK1, KLK4, or KLK4 and KLK8, and the like. The stronger the inhibitory activity (the smaller $IC_{50}$ value) or the higher the affinity (the smaller $K_D$ value) of the inhibitory peptide of the present invention against the target, the lower the dose required to exert its drug effect.

The dose of the KLK1 inhibitory peptide, KLK4 inhibitory peptide, or KLK4/KLK8 inhibitory peptide of the present invention is not limited as long as it is a pharmacologically effective amount, and it can be appropriately determined according to factors such as the species of the individual, the type of disease, symptoms, sex, age, chronic disease, inhibitory activity or binding affinity to the target of the peptide, and the like. However, usually, 0.01 to 1000 mg/kg, preferably 0.1 to 100 mg/kg of the KLK1 inhibitory peptide, KLK4 inhibitory peptide, or KLK4/KLK8 inhibitory peptide may be administered once for 1 to 180 days, or twice or three or more times a day.

Examples of the form of the pharmaceutical compositions include injectables (including lyophilized formulations and drops), suppositories, transnasal absorption formulations, transdermal absorption formulations, sublingual agents, capsules, tablets, ointments, granules, aerosols, pills, powders, suspensions, emulsions, eye drops, and bio embedded formulations.

A pharmaceutical composition containing the KLK1 inhibitory peptide, KLK4 inhibitory peptide, or KLK4/KLK8 inhibitory peptide as an active ingredient can be administered simultaneously with or separately from an additional pharmaceutical. For example, a pharmaceutical composition containing the KLK1 inhibitory peptide, KLK4 inhibitory peptide, or KLK4/KLK8 inhibitory peptide as an active ingredient is administered after administering the additional pharmaceutical, or before administering the additional pharmaceutical, or the pharmaceutical composition and the additional pharmaceutical may be administered simultaneously with such pharmaceutical composition. When administered simultaneously, the KLK1 inhibitory peptide, KLK4 inhibitory peptide, or KLK4/KLK8 inhibitory peptide and the additional pharmaceutical may be contained in either a single preparation or separate preparations (multiple preparations).

One or two or three or more additional pharmaceuticals may be administered or received. These are collectively referred to as the "combinational use with an additional pharmaceutical" or "combination with an additional pharmaceutical" of the pharmaceutical composition of the present invention. The pharmaceutical composition of the present invention containing an additional pharmaceutical or used in combination with an additional pharmaceutical in addition to the peptide of the present invention or a conjugate thereof is also included within the present invention as an embodiment of the "combinational use with an additional pharmaceutical" or "combination with an additional pharmaceutical".

The present invention provides a method for treating or preventing diseases related to KLK1, diseases related to KLK4, or diseases related to KLK4/KLK8 including a step of administering the KLK1 inhibitory peptide, KLK4 inhibitory peptide, or KLK4/KLK8 inhibitory peptide; a use of the KLK1 inhibitory peptide, KLK4 inhibitory peptide, or KLK4/KLK8 inhibitory peptide of the present invention for preparing a pharmaceutical composition for treating or preventing the disease; and a use of the KLK1 inhibitory peptide, KLK4 inhibitory peptide, or KLK4/KLK8 inhibitory peptide for the treatment or prevention of the disease. A kit for treatment or prevention, containing the peptide of the present invention is also included within the present invention.

Furthermore, the present invention provides a polynucleotide containing a nucleotide sequence encoding an amino acid sequence contained in the KLK1 inhibitory peptide, KLK4 inhibitory peptide, or KLK4/KLK8 inhibitory peptide of the present invention or a conjugate thereof; a vector containing the polynucleotide; a pharmaceutical composition containing a cell containing the polynucleotide or the vector or expressing the KLK1 inhibitory peptide, KLK4 inhibitory peptide, or KLK4/KLK8 inhibitory peptide of the present invention or a conjugate thereof. For example, such a polynucleotide and vector can be applied to a gene therapy for diseases related to KLK1, diseases related to KLK4, or diseases related to KLK4/KLK8, and such a cell can be applied to a cell therapy for diseases related to KLK1, diseases related to KLK4, or diseases related to KLK4/KLK8, respectively using known techniques. Furthermore,

6. Diagnostic Composition

The present invention also provides a composition for testing or diagnosis (hereinafter, collectively referred to as the "diagnostic composition") containing the KLK1 inhibitory peptide, KLK4 inhibitory peptide, or KLK4/KLK8 inhibitory peptide of the present invention or a conjugate thereof.

The diagnostic composition of the present invention is useful for testing or diagnosis of diseases related to KLK1, diseases related to KLK4, diseases related to KLK4/KLK8, KLK1 expression, KLK4 expression, KLK8 expression, or the like. Examples of testing or diagnosis within the present invention include determination or measurement of morbidity risk, determination of the presence or absence of morbidity, measurement of the degree of progression or deterioration, measurement or determination of the effect of drug treatment with a pharmaceutical composition containing the KLK1 inhibitory peptide, KLK4 inhibitory peptide, or KLK4/KLK8 inhibitory peptide, measurement or determination of the effect of treatment other than drug treatment, measurement of recurrence risk, and determination of whether the recurrence has occurred or not. However, the testing and diagnosis within the present invention are not limited to these examples as long as they constitute testing or diagnosis.

The diagnostic composition of the present invention is useful for identifying an individual to whom the peptide of the present invention or a conjugate thereof, a composition containing them, or a pharmaceutical composition containing them is to be administered.

Such a diagnostic composition can contain a pH buffer, an osmotic adjustment agent, salts, a stabilizer, a preservative, a colorant, a sensitizer, an anti-aggregation agent, and the like.

The present invention also provides a method for testing or diagnosing diseases related to KLK1, diseases related to KLK4, or diseases related to KLK4/KLK8, a use of the peptide of the present invention for preparing a diagnostic composition for the diseases, and a use of the peptide of the present invention for testing or diagnosing the diseases. A kit for testing or diagnosis containing the peptide of the present invention is also included within the present invention.

The testing or diagnostic method using the peptide of the present invention is preferably performed with detection methods such as a sandwich ELISA, but can also be performed with a normal ELISA method, a RIA method, an Enzyme-Linked ImmunoSpot (ELISPOT) method, a dot blot method, an ouchterlony method, a counterimmunoelectrophoresis (CIE) method, a chemiluminescent immuno assay (CLIA), or flow cytometry (FCM). For detection, an antibody, or ones obtained by labeling the peptide of the present invention or a conjugate thereof can be used. As regards to the labeling means, biotin, as well as other labeling means that can be used for biochemical analysis, such as HRP, alkaline phosphatase, FITC, and other fluorophores, radioisotope labeling or the like can be used. For detection using an enzyme label, chromogenic substrates such as TMB (3,3',5,5'-tetramethylbenzidine), BCIP (5-bromo-4-chloro-3-indolyl phosphate), p-NPP (p-nitrophenyl phosphate), OPD (o-phenylenediamine), ABTS (3-ethylbenzothiazoline-6-sulfonic acid), and SuperSignal ELISA Pico Chemiluminescent Substrate (Thermo Fisher Scientific); fluorogenic substrates such as QuantaBlu® Fluorogenic Peroxidase Substrate (Thermo Fisher Scientific); as well as other chemiluminescent substrates can be used. Samples derived from human or non-human animals as well as artificially processed samples, such as recombinant protein, can be subjected to the measurement. Examples of test samples derived from bodies of living organisms include, but are not limited to, blood, joint fluid, ascites, lymph fluid, cerebrospinal fluid, alveolar lavage fluid, saliva, sputum, tissue homogenate supernatant, and tissue sections.

A sandwich ELISA kit for testing or diagnosis containing the peptide of the present invention may contain a standard protein solution of the KLK1 inhibitory peptide, KLK4 inhibitory peptide or KLK4/KLK8 inhibitory peptide, a coloring reagent, a dilution buffer, a protein for immobilization, a protein for detection, and a washing solution. As a method for measuring the amount of protein bound to an antigen, an absorbance method, a fluorescence method, a luminescence method, a radioisotope (RI) method and the like can be suitably used. For measurements, an absorbance plate reader, a fluorescence plate reader, a luminescence plate reader, an RI liquid scintillation counter and the like can be suitably used.

The testing or diagnosis can also be performed with a method that uses immunoprecipitation methods.

The present invention also provides a method for detecting or measuring KLK1, KLK4, or KLK4 and KLK8 in a test sample. The diagnostic composition of the present invention can be used for a method for detecting or measuring these. The KLK1, KLK4, or KLK4 and KLK8 in a sample can be detected by step 1 of contacting the KLK1 inhibitory peptide, KLK4 inhibitory peptide, or KLK4/KLK8 inhibitory peptide or a conjugate thereof with a test sample, and subsequently, step 2 of measuring the amount of, or detecting, KLK1, KLK4, or KLK4 and KLK8 bound to the peptide. Step 1 may include, for example, immobilizing the KLK1 inhibitory peptide, KLK4 inhibitory peptide, or KLK4/KLK8 inhibitory peptide conjugated with an Fc region of an immunoglobulin to magnetic beads via Protein G, and adding a test sample thereto. Step 2 may include, for example, separating the magnetic beads, analyzing the soluble protein precipitated together with the beads by SDS-PAGE or Western blot method, and detecting KLK1, KLK4, or KLK4 and KLK8. Samples derived from human or non-human animals as well as artificially processed samples, such as recombinant protein, can be subjected to the measurement. Examples of test samples derived from bodies of living organisms include, but are not limited to, blood, joint fluid, ascites, lymph fluid, cerebrospinal fluid, alveolar lavage fluid, saliva, sputum, tissue homogenate supernatant, and tissue sections.

The KLK1, KLK4, or KLK4 and KLK8 detection can be performed not only in vitro but also in vivo. When image diagnosis is used, a KLK1 inhibitory peptide, KLK4 inhibitory peptide, or KLK4/KLK8 inhibitory peptide or a conjugate thereof labeled with a pharmaceutically acceptable radionuclide or illuminant can be used. Step 1 may include, for example, administering to a subject the peptide with a label or a conjugate thereof. Furthermore, step 2 may include, for example, taking an image using an image diagnostic technique such as PET/CT, and determining or examining the presence of active KLK1, KLK4, or KLK4 and KLK8.

The peptide or a conjugate thereof contained in the diagnostic composition of the present invention binds to KLK1, KLK4, or KLK4 and KLK8, and preferably has KLK1, KLK4, or KLK4 and KLK8-specific binding activity.

A method of identifying an individual to whom a pharmaceutical composition of the present invention is to be administered is also encompassed by the present invention. In the identification method, KLK1, KLK4, or KLK4 and KLK8 in a sample derived from the individual is measured, and when KLK1, KLK4, or KLK4 and KLK8 is detected in the sample, or the amount of KLK1, KLK4, or KLK4 and KLK8 detected in the sample is more than that in a sample derived from a healthy individual, the individual can be determined to be positive. The diagnostic composition of the present invention can be used in the identification method.

In a preferred embodiment of the identification method, the individual suffers from or is at risk of a KLK1-related disease, a KLK4-related disease and/or a KLK4/KLK8-related disease.

Furthermore, in one embodiment thereof, the pharmaceutical composition of the present invention can be administered to an individual who has been determined to be positive in the identification method.

7. Separation Method of KLK1, KLK4, or KLK4 and KLK8

The KLK1 inhibitory peptide, KLK4 inhibitory peptide, or KLK4/KLK8 inhibitory peptide of the present invention has a specific binding activity to KLK1, KLK4, or KLK4 and KLK8. Thus, with the preferred KLK1 inhibitory peptide, KLK4 inhibitory peptide, or KLK4/KLK8 inhibitory peptide of the present invention or a conjugate thereof, it is possible to specifically separate KLK1, KLK4, or KLK4 and KLK8 from a sample in which KLK1, KLK4 or KLK4 and KLK8 and other KLKs are co-existent. The release of KLK1, KLK4 or KLK4 and KLK8 from the peptide can be carried out non-selectively under conditions such as relatively high ionic strength, low pH, moderate denaturation, the presence of chaotropic salts, or the like, but it is preferred that the release is carried out within the range that the protease activity of KLK1, KLK4 or KLK4 and KLK8 is not attenuated.

EXAMPLES

Example 1

Preparation of KLK1, KLK4 and KLK8

(1-1) Construction of KLK1, KLK4, KLK8 Expression Vectors

Using a nucleotide sequence encoding pro-KLK1 (SEQ ID NO: 2, FIG. 8, UniProt; P06870), a nucleotide sequence encoding pro-KLK4 (SEQ ID NO: 3, FIG. 9, UniProt; Q9Y5K2), and a nucleotide sequence encoding pro-KLK8 (SEQ ID NO: 4, FIG. 10, UniProt; O60259) as templates, each fragment was amplified by the overlap PCR method (94° C., 15 seconds; 60° C., 30 seconds; 68° C., 30 seconds)×30 cycles) using KOD-plus- (Toyobo Co., Ltd.), and mammalian cell expression vectors pCMA_pro-KLK1, pCMA_pro-KLK4, and pCMA_pro-KLK8, in which a His tag was added to the C-terminal end of each gene were constructed.

(1-2) Expression and Purification of Pro-KLK1, Pro-KLK4, Pro-KLK8

The expression vectors constructed in (1-1) were transfected to Expi 293F cells (Thermo Fisher Scientific) using PEI MAX 40000 (Polysciences, Inc.), and the transfected cells were cultured for three days, then the culture supernatant was recovered. The desired His tag fusion proteins were recovered from the culture supernatant using HisTrap excel (GE healthcare), and the buffer was exchanged to PBS using Amicon Ultra NMWL 10,000 (Merck Millipore) to purify pro-KLK1, pro-KLK4, and pro-KLK8, respectively.

(1-3) Preparation of KLK1, KLK4, KLK8

To 200 μg/mL of pro-KLK1 prepared with a KLK activation buffer (50 mM Tris-HCl, 150 mM NaCl, 10 mM $CaCl_2$), pH 7.5), an equal amount of 2 μg/mL of thermolysin was added. The mixture was reacted at 37° C. for a certain period of time, then mixed with an equal amount of 20 mM 1,10-phenanthroline to prepare activated KLK1. Similarly, an equal amount of 8 μg/mL Thermolysin was added to 200 μg/mL of pro-KLK4 or pro-KLK8 prepared with a KLK activation buffer. The mixture was reacted at 37° C. for a certain period of time, then mixed with an equal amount of 20 mM 1,10-phenanthroline to prepare activated KLK4 or KLK8.

Example 2

Preparation of KLK1 Inhibitory Peptide, KLK4 Inhibitory Peptide, KLK4/KLK8 Inhibitory Peptide (2-1) Construction of Expression Vectors for KLK1 Inhibitory Peptide, KLK4 Inhibitory Peptide, KLK4/KLK8 Inhibitory Peptide Expression vectors for the KLK1 inhibitory peptide, KLK4 inhibitory peptide and KLK4/KLK8 inhibitory peptide having a backbone of the SPINK2 scaffold were constructed. Using the nucleotide sequences encoding the amino acid sequences of each inhibitory peptide (SEQ ID NOs: 5 to 22, FIGS. 11 to 28) and the nucleotide sequence encoding human SPINK2 (SEQ ID NO: 1, FIG. 7) as templates, the fragments of each inhibitory peptide were amplified by PCR method ((94° C., 15 seconds; 60° C., 30 seconds; 68° C., 30 seconds)×30 cycles) using the following primers and KOD-plus-(Toyobo Co., Ltd.).

```
Primer 1:
                               (SEQ ID NO: 24; FIG. 30)
5'-AAAAGAATTCTGATCCGCAGTTTGGTCTGTTTAG-3'

Primer 2:
                               (SEQ ID NO: 25; FIG. 31)
5'-AAAACTCGAGTTATGCGGCCGCAGACGCGCCGCACGGACC-3'
```

The amplified fragments were subjected to agarose gel electrophoresis, then the desired DNA fragment was excised, and the DNA was prepared by QIAquick Gel Extraction Kit (QIAGEN). The prepared DNA fragments and pET 32a (modified) were treated with restriction enzymes EcoRI (New England Biolabs, Inc.) and XhoI (New England Biolabs, Inc.) at 37° C. for 1 hour or more. After the agarose gel electrophoresis, the desired DNA fragments were excised, and purified by QIAquick PCR Purification Kit (QIAGEN). The purified fragments were reacted with T4 DNA Ligase (New England Biolabs, Inc.) at 16° C. overnight to carry out a ligation reaction. The ligation solution was added to *E. coli* JM109 (Toyobo Co., Ltd.) and allowed to stand on ice for 30 minutes. The resulting solution was then subjected to heat treatment of 42° C. for 45 seconds, and allowed to stand on ice for 5 minutes, then seeded on a 2YT plate containing 0.1 mg/mL ampicillin, and then subjected to static culture at 37° C. overnight to transform E. coli. The next day, the transformed E. coli were inoculated into Terrific broth medium (Invitrogen) containing 0.1 mg/mL ampicillin, and cultured at 37° C. overnight. Then, plasmid DNA was recovered using QIAprep 96 Turbo Miniprep Kit (Qiagen), and sequence analysis was performed to construct "pET 32a (modified)_KLK1 inhibitory peptide", "pET 32a(modified)_KLK4 inhibitory peptide", and "pET 32a(modified)_KLK4/KLK8 inhibitory peptide".

(2-2) Expression and Purification of KLK1 Inhibitory Peptide, KLK4 Inhibitory Peptide, KLK8 Inhibitory Peptide E. coli Origami B (DE3) (Novagen) was transformed with the vectors constructed in (2-1) respectively, and the transformed E. coli were cultured at 37° C. using 2YT medium containing 0.1 mg/mL ampicillin. IPTG (final concentration of 1 mM) was then added, and the mixture was cultured at 16° C. overnight. The next day, the cells were recovered by centrifugation (3,000 g, 20 minutes, 4° C.), then the lysate was prepared using BugBuster Master Mix (Novagen), and the target protein fused with a His tag was purified using TALON Metal Affinity Resin (Clontech Laboratories, Inc.). Next, the thioredoxin tag was cleaved off from the target protein using Thrombin Cleavage Capture Kit (Novagen), then subjected to purification with TALON. Furthermore, by subjecting the resultant mixture to gel filtration chromatography (Superdex 75 10/300 GL), the KLK1 inhibitory peptide, KLK4 inhibitory peptide, and KLK4/KLK8 inhibitory peptide, each containing an S tag and a linker (SEQ ID NO: 26, FIG. 32) at the N-terminal end and 6 residues (SEQ ID NO: 27, FIG. 33) at the C-terminal end were purified.

Example 3

Evaluation of Each Inhibitory Peptide (3-1) Evaluation of KLK1, KLK4, and KLK4/KLK8 Inhibitory Activity of Each Inhibitory Peptide Using Peptide Substrate The substrate peptide was dissolved in DMSO to 10 mM, then diluted with an assay buffer (50 mM Tris-HCl, 150 mM NaCl, pH 8.0) and used at the final concentration of 100 μM. 25 μL each of the KLK1, KLK4, or KLK8 diluted with the assay buffer and the inhibitory peptide were mixed, and reacted at 37° C. for 20 minutes. Then, 50 μL of the substrate diluted with the assay buffer was added, and fluorescence signals (excitation 380 nm/emission 460 nm) were measured with Enspire (PerkinElmer, Inc.). The combinations of each enzyme and substrate were used as follows. For KLK1 inhibitory activity evaluation, 1 nM final concentration of KLK1 and 100 μM final concentration of PFR-AMC (Bachem Holding AG) were used. For KLK4 inhibitory activity evaluation, 10 nM final concentration of KLK4 and 100 μM final concentration of Boc-VPR-AMC (R&D Systems, Inc.) were used. For KLK8 inhibitory activity evaluation, 20 nM final concentration of KLK8 and 100 μM final concentration of Boc-VPR-AMC (R&D Systems, Inc.) were used. Each inhibitory peptide was used at the final concentration of 1.875 to 1,000 nM. For reactions and measurements, a ProteoSave® SS96F black plate (Sumitomo Bakelite Co., Ltd.) was used.

The 50% inhibitory concentration ($IC_{50}$) of each inhibitory peptide was calculated using GraphPad Prism (version 5.0; GraphPad Software Inc.) by calculating the substrate peptide degradation rate of each inhibitory peptide at each concentration, and taking the degradation rate at an inhibitor concentration of 0 nM as 100%. As regards the results, it was revealed that each of the inhibitory peptides inhibit KLK1, KLK4, or KLK8 enzyme activity at low concentrations (FIG. 2). Furthermore, for the KLK4 inhibitory peptide, the measurement result was subjected to nonlinear curve fitting, and the $K_i$ value was calculated according to Morrison's formula (FIG. 3). As the result, it was shown that many KLK4 inhibitory peptides and KLK4/KLK8 inhibitory peptides have a $K_i$ value of less than 1 nM and that they are potent inhibitors. It should be noted that the average value of three independent experiments was used for the calculation of the $IC_{50}$ and $K_i$ values.

(3-2) Specificity Evaluation of Each Inhibitory Peptide

The specificities for other proteases were evaluated using the substrate peptide cleavage as an index. In the same way as in the method described in (3-1), 25 μL each of the proteases diluted with the assay buffer and a sample (final concentration of 1 μM) were mixed, and the mixtures were reacted at 37° C. for 20 minutes. Then, 50 μL of the substrate diluted with the assay buffer was added, and fluorescence signals (excitation 380 nm/emission 460 nm) were measured with Enspire (PerkinElmer, Inc.). For the protease activity evaluation, an assay buffer (50 mM Tris, 150 mM NaCl, pH 8.0) was used. For reactions and measurements, a ProteoSave® SS96F black plate (Sumitomo Bakelite Co., Ltd.) was used. The combinations of proteases and substrates used for the specificity evaluation were as follows.

Bovine α-chymotrypsin inhibitory activity evaluation; 10 nM final concentration of chymotrypsin (Worthington Biochemical Corporation; LS001434) and 100 μM final concentration of substrate peptide Suc-LLVY-MCA (SEQ ID NO: 29) (PEPTIDE INSTITUTE, INC.; 3120-v)

Human tryptase inhibitory activity evaluation; 1 nM final concentration of tryptase (Sigma-Aldrich Co.; T7063), and 100 μM final concentration of substrate peptide Boc-Phe-Ser-Arg-MCA (PEPTIDE INSTITUTE, INC.; 3107-v)

Human chymase inhibitory activity evaluation; 100 nM final concentration of chymase (Sigma-Aldrich Co.; C8118), and 100 μM final concentration of substrate peptide Suc-Leu-Leu-Val-Tyr-MCA (SEQ ID NO: 29) (PEPTIDE INSTITUTE, INC.; 3114-v)

Human plasmin inhibitory activity evaluation; 50 nM final concentration plasmin (Sigma-Aldrich Co.; P1867), and 100 μM final concentration of substrate peptide Boc-Val-Leu-Lys-MCA (PEPTIDE INSTITUTE, INC.; 3104-v)

Human thrombin inhibitory activity evaluation; 1 nM final concentration of thrombin (Sigma-Aldrich Co.; T6884), and 100 μM final concentration of substrate peptide Boc-VPR-AMC Fluorogenic Peptide Substrate (R&D Systems, Inc.; ES011)

Neutrophil elastase inhibitory activity; 0.02 U/μL final concentration of Neutrophil elastase (Enzo Life Sciences, Inc.), and 100 μM final concentration of substrate peptide Suc(OMe)-Ala-Ala-Pro-Val-MCA (SEQ ID NO: 30) (PEPTIDE INSTITUTE, INC.; 3153-v)

Human matriptase inhibitory activity evaluation: 1 nM final concentration of matriptase (R&D Systems, Inc.; E3946-SE), and 100 μM final concentration of substrate peptide Boc-QAR-AMC Fluorogenic Peptide Substrate (ES014)

Human protein C inhibitory activity evaluation; 100 nM final concentration of protein C (Sigma-Aldrich Co.; P2200), and 100 μM final concentration of substrate peptide Boc-Leu-Ser-Thr-Arg-MCA (SEQ ID NO: 31) (PEPTIDE INSTITUTE, INC.; 3112-v)

Human tPA inhibitory activity evaluation; 10 nM final concentration of tPA (Sigma-Aldrich Co.; T0831), and 100 μM final concentration of substrate peptide Pyr-Gly-Arg-MCA (PEPTIDE INSTITUTE, INC.; 3145-v)

Human uPA inhibitory activity evaluation; 10 nM final concentration of uPA (Sigma-Aldrich Co.; T0831), and 100 μM final concentration of substrate peptide Pyr-Gly-Arg-MCA (PEPTIDE INSTITUTE, INC.; 3145-v)

Human plasma kallikrein inhibitory activity evaluation; 0.125 μg/ml final concentration of plasma kallikrein (Sigma-Aldrich; T0831), and 100 μM final concentration of substrate peptide Z-Phe-Arg-MCA (PEPTIDE INSTITUTE, INC.; 3095-v).

Human HTRA2 inhibitory activity evaluation; 200 nM final concentration of HTRA2 (R&D Systems, Inc.; 1458-HT), and 50 μM final concentration of substrate peptide H2-Opt (PEPTIDE INSTITUTE, INC.)

In the same way as in (3-1), the cross-reactivity to proteases other than KLK1, KLK4, or KLK8 was evaluated using degradation of the peptide substrate as an index. While some inhibitors showed weak cross-reactivity to chymotrypsin, plasmin or the like at the inhibitor final concentration of 1 uM, many inhibitors did not suppress protease activities of any of the proteases, thus it was shown that they have specific inhibitory activity for KLK1, KLK4, or KLK4 and KLK8 (FIGS. 4A-1 through FIGS. 4D-2).

Example 4

Binding Affinity of KLK4 Inhibitory Peptide

Surface plasmon resonance analysis was performed using BIAcore T200 (GE healthcare) to measure the binding affinity of KLK4 inhibitory peptides by single cycle kinetics. The complementary strand of DNA of the streptavidin conjugate was captured by hybridization to Sensor Chip CAP (GE healthcare) on which the single-stranded DNA was immobilized. Next, approximately 5 RU of KLK4 biotinylated with EZ-Link NHS-PEG4-Biotin (Thermo Fisher Science) was captured at a flow rate of 10 μL/min and immobilized. Thereafter, three-fold serially diluted KLK4 inhibitory peptide (0.08 to 20 nM) with HBS-EP was added as an analyte at a flow rate of 10 μL/min. Analysis was performed using BIAcore T 200 Evaluation software (version 2.0), and $k_{on}$ and $k_{off}$ were calculated using simple one-to-one Langmuir binding model. The equilibrium constant $K_D$ was calculated as a $k_{off}/k_{on}$ ratio. By regenerating Sensor Chip CAP using a regeneration buffer attached to Biotin CAPture Kit (GE healthcare) and repeatedly having biotinylated KLK4 captured, multiple KLK4 inhibitory peptides were measured. All of the three measured KLK4 inhibitory peptides showed a $K_D$ value of less than 1 nM, showing that their binding is very strong (FIG. 5).

Example 5

X-Ray Crystal Structure Analysis of KLK4/KLK4 Inhibitory Peptide Complex (5-1) Preparation of KLK4/KLK4 Inhibitory Peptide complex According to the methods described in (1-3) and (2-2), KLK4 and a KLK4 inhibitory peptide having the amino acid sequence represented by K41043 (SEQ ID NO: 19: FIG. 25) were prepared, respectively. After mixing them under the condition of 50 mM Tris-HCl, 150 mM NaCl, pH 8.0, the complex was isolated and purified by gel filtration chromatography (Superdex 200 10/300 GL).

(5-2) X-Ray Crystal Structure Analysis

The complex solution prepared in (5-1) was concentrated to 30 mg/mL, and EKMax (Invitrogen) was added to a final concentration of 16.7 U/uL, then the resultant solution was mixed with a reservoir solution (LiCl 0.2 M, 20% PEG3350) at 1:1, and the mixture was crystallized by a vapor diffusion method. The obtained single crystal was immersed in a cryo solution (20% glycerol, PBS, reservoir solution) and then frozen in liquid nitrogen. The frozen crystal was irradiated with X-rays under a cryostream, and diffraction images were obtained (photon factory NE3A: High Energy Accelerator Research Organization). Analysis was performed using imosflm, and a scaling data for a maximum resolution of 1.9 Å (angstrom) was obtained. The phase was determined by a molecular replacement method using the KLK4 monomer (PDB ID: 4K1E) and the SPINK2 monomer (PDB ID: 2JXD) as templates. After the structure refinement, the complex crystal of KLK4/the peptide was determined with a resolution of 2.0 A. It was confirmed that the KLK4 inhibitory peptide was bound to a region containing the KLK4 enzyme active center (FIG. 6).

INDUSTRIAL APPLICABILITY

The peptide provided by the present invention and the pharmaceutical and diagnostic compositions containing the peptide are useful for the treatment, prevention, testing, diagnosis or the like of diseases related to KLK1, diseases related to KLK4, or diseases related to KLK4/KLK8.

FREE TEXT OF SEQUENCE LISTING

SEQ ID NO: 1: Amino acid sequence of human SPINK2 (FIG. 7)
SEQ ID NO: 2: Amino acid sequence of human KLK1 (FIG. 8)
SEQ ID NO: 3: Amino acid sequence of human KLK4 (FIG. 9)
SEQ ID NO: 4: Amino acid sequence of human KLK8 (FIG. 10)
SEQ ID NO: 5: Amino acid sequence of KLK1 inhibitory peptide K10061 (FIG. 11)
SEQ ID NO: 6: Amino acid sequence of KLK1 inhibitory peptide K10062 (FIG. 12)
SEQ ID NO: 7: Amino acid sequence of KLK1 inhibitory peptide K10066 (FIG. 13)
SEQ ID NO: 8: Amino acid sequence of KLK1 inhibitory peptide K10071 (FIG. 14)
SEQ ID NO: 9: Amino acid sequence of KLK4 inhibitory peptide K40001 (FIG. 15)
SEQ ID NO: 10: Amino acid sequence of KLK4 inhibitory peptide K40003 (FIG. 16)
SEQ ID NO: 11: Amino acid sequence of KLK4 inhibitory peptide K40004 (FIG. 17)
SEQ ID NO: 12: Amino acid sequence of KLK4 inhibitory peptide K40005 (FIG. 18)
SEQ ID NO: 13: Amino acid sequence of KLK4/KLK8 inhibitory peptide K41021 (FIG. 19)
SEQ ID NO: 14: Amino acid sequence of KLK4/KLK8 inhibitory peptide K41024 (FIG. 20)
SEQ ID NO: 15: Amino acid sequence of KLK4/KLK8 inhibitory peptide K41025 (FIG. 21)
SEQ ID NO: 16: Amino acid sequence of KLK4/KLK8 inhibitory peptide K41026 (FIG. 22)
SEQ ID NO: 17: Amino acid sequence of KLK4/KLK8 inhibitory peptide K41041 (FIG. 23)
SEQ ID NO: 18: Amino acid sequence of KLK4/KLK8 inhibitory peptide K41042 (FIG. 24)

SEQ ID NO: 19: Amino acid sequence of KLK4/KLK8 inhibitory peptide K41043 (FIG. 25)
SEQ ID NO: 20: Amino acid sequence of KLK4/KLK8 inhibitory peptide K41045 (FIG. 26)
SEQ ID NO: 21: Amino acid sequence of KLK4/KLK8 inhibitory peptide K41046 (FIG. 27)
SEQ ID NO: 22: Amino acid sequence of KLK4/KLK8 inhibitory peptide K41047 (FIG. 28)
SEQ ID NO: 23: A general formula of KLK1 inhibitory binding peptide, KLK4 inhibitory peptide, or KLK4/KLK8 inhibitory peptide (FIG. 29)
SEQ ID NO: 24: Nucleotide sequence of primer 1 (FIG. 30)
SEQ ID NO: 25: Nucleotide sequence of primer 2 (FIG. 31)
SEQ ID NO: 26: Amino acid sequence of Stag+linker 1 (FIG. 32)
SEQ ID NO: 27: Amino acid sequence of C-terminal 6-mer (FIG. 33)
SEQ ID NO: 28: Amino acid sequence of human IgG1 Fc (FIG. 34)

The invention claimed is:

1. A serine protease inhibitor kazal-type 2 (SPINK2) mutant peptide which comprises the amino acid sequence represented by SEQ ID NO: 9, SEQ ID NO: 10, SEQ ID NO: 11, or SEQ ID NO: 12.

2. The peptide according to claim 1, wherein the peptide has a conformation characterized by having three disulfide bonds, a loop structure, an α-helix, and a β-sheet.

3. A conjugate comprising the peptide according to claim 1 and another moiety bound thereto.

4. The conjugate according to claim 3, wherein the another moiety bound thereto is a peptide.

5. The conjugate according to claim 3, wherein the another moiety bound thereto comprises an immunoglobulin Fc region or a functional fragment thereof.

6. A composition comprising the peptide according to claim 1.

7. A pharmaceutical composition comprising the peptide according to claim 1.

8. A pharmaceutical composition comprising the conjugate according to claim 3.

9. A composition for test or diagnosis, comprising the peptide according to claim 1.

10. A serine protease inhibitor kazal-type 2 (SPINK2) mutant peptide which comprises the amino acid sequence represented by SEQ ID NO: 9, SEQ ID NO: 10, SEQ ID NO: 11, or SEQ ID NO: 12, and specifically inhibits protease activity of Kallikrein-related peptidase 4 (KLK4).

11. The peptide according to claim 10, wherein the peptide has a conformation characterized by having three disulfide bonds, a loop structure, an α-helix, and a β-sheet.

12. A conjugate comprising the peptide according to claim 10 and another moiety bound thereto.

13. The conjugate according to claim 12, wherein the another moiety bound thereto is a peptide.

14. The conjugate according to claim 12, wherein the another moiety bound thereto comprises an immunoglobulin Fc region or a functional fragment thereof.

15. A composition comprising the peptide according to claim 10.

16. A pharmaceutical composition comprising the peptide according to claim 10.

17. A composition for test or diagnosis, comprising the peptide according to claim 10.

18. A polynucleotide comprising a nucleotide sequence encoding the peptide sequence of SEQ ID NOs: 9-12.

19. A pharmaceutical composition comprising the polynucleotide according to claim 1.

20. A method for producing the peptide according to claim 1, comprising a step of preparing the peptide by chemical synthesis or by recombinant technology.

21. A method for producing the conjugate according to claim 6, comprising a step of preparing the conjugate by chemical synthesis or by recombinant technology, wherein the another moiety bound thereto is a peptide.

22. A method for producing the peptide according to claim 10, comprising a step of preparing the peptide by chemical synthesis or by recombinant technology.

23. A method for producing the conjugate according to claim 12, comprising a step of preparing the conjugate by chemical synthesis or by recombinant technology, wherein the another moiety bound thereto is a peptide.

* * * * *